(12) United States Patent
Frey et al.

(10) Patent No.: US 9,186,097 B2
(45) Date of Patent: Nov. 17, 2015

(54) BODY FLUID LANCING, ACQUIRING, AND TESTING CARTRIDGE DESIGN

(75) Inventors: Stephan-Michael Frey, Griesheim (DE); Hans List, Hesseneck-Kailbach (DE); Hansjoerg Braendle, Niederuzwil (CH); Christian Hoerauf, Oftersheim (DE); Steven N. Roe, San Mateo, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 741 days.

(21) Appl. No.: 12/695,374

(22) Filed: Jan. 28, 2010

(65) Prior Publication Data

US 2010/0174211 A1      Jul. 8, 2010

Related U.S. Application Data

(63) Continuation-in-part of application No. 12/568,009, filed on Sep. 28, 2009, now Pat. No. 8,961,431, and a continuation-in-part of application No. PCT/EP2008/062130, filed on Sep. 12, 2008.

(60) Provisional application No. 60/972,996, filed on Sep. 17, 2007.

(51) Int. Cl.
*A61B 5/15*       (2006.01)
*A61B 5/151*      (2006.01)
*A61B 5/157*      (2006.01)

(52) U.S. Cl.
CPC ........... *A61B 5/1411* (2013.01); *A61B 5/15146* (2013.01); *A61B 5/157* (2013.01)

(58) Field of Classification Search
CPC ............... A61B 5/1405; A61B 5/1411; A61B 5/150022; A61B 5/151–5/15198; A61B 5/157
USPC .................. 600/573, 583–584; 606/181–182
See application file for complete search history.

(56) References Cited

U.S. PATENT DOCUMENTS

| | | | |
|---|---|---|---|
| 4,794,926 A | 1/1989 | Munsch et al. | |
| 5,829,589 A | 11/1998 | Nguyen et al. | |

(Continued)

FOREIGN PATENT DOCUMENTS

| | | |
|---|---|---|
| CN | 1456887 A | 11/2003 |
| EP | 1 203 563 A2 | 5/2002 |

(Continued)

OTHER PUBLICATIONS

Machine translation from German to English for EP 1491143 A1.*

(Continued)

*Primary Examiner* — Adam J Eiseman
(74) *Attorney, Agent, or Firm* — Woodard, Emhardt, Moriarty, McNett & Henry LLP

(57) ABSTRACT

A disposable device for analyzing body fluid especially for blood sugar tests includes a container which can be inserted into a measuring apparatus, a sampling member provided in the container to pierce skin of a body part and sample body fluid, and a test member for receiving body fluid obtained by the skin-piercing. In one form, the test member is fixed in a retaining chamber of the container, and the sampling member is configured in the same retaining chamber such that it is separated at a distance from the test member in an initial state and is in contact with the test member to transfer body fluid in a transfer state after the skin-piercing.

49 Claims, 51 Drawing Sheets

(56) References Cited

U.S. PATENT DOCUMENTS

| | | |
|---|---|---|
| 5,851,215 A | 12/1998 | Mawhirt et al. |
| 6,228,100 B1 | 5/2001 | Schraga |
| 7,004,928 B2 | 2/2006 | Aceti et al. |
| 7,150,755 B2 | 12/2006 | Levaughn et al. |
| 7,192,405 B2 | 3/2007 | DeNuzzio et al. |
| 7,223,248 B2 | 5/2007 | Erickson et al. |
| 7,343,188 B2 | 3/2008 | Sohrab |
| 7,771,367 B2 | 8/2010 | Haar et al. |
| 2002/0052618 A1 | 5/2002 | Haar et al. |
| 2002/0120216 A1 | 8/2002 | Fritz et al. |
| 2002/0130042 A1 | 9/2002 | Moerman et al. |
| 2003/0211619 A1 | 11/2003 | Olson et al. |
| 2003/0212347 A1 | 11/2003 | Sohrab |
| 2004/0039303 A1 | 2/2004 | Wurster et al. |
| 2004/0064068 A1 | 4/2004 | DeNuzzio et al. |
| 2004/0102803 A1 | 5/2004 | Boecker et al. |
| 2004/0138688 A1 | 7/2004 | Giraud |
| 2004/0193202 A1 | 9/2004 | Allen |
| 2005/0011759 A1* | 1/2005 | Moerman et al. ........ 204/403.03 |
| 2005/0015020 A1 | 1/2005 | LeVaughn et al. |
| 2005/0036909 A1 | 2/2005 | Erickson et al. |
| 2005/0149088 A1 | 7/2005 | Fukuda et al. |
| 2006/0064035 A1 | 3/2006 | Wang et al. |
| 2006/0094985 A1 | 5/2006 | Aceti et al. |
| 2006/0178600 A1 | 8/2006 | Kennedy et al. |
| 2006/0200044 A1 | 9/2006 | Freeman et al. |
| 2006/0204399 A1 | 9/2006 | Freeman et al. |
| 2007/0016103 A1* | 1/2007 | Calasso et al. ................ 600/583 |
| 2007/0142748 A1 | 6/2007 | Deshmukh et al. |
| 2007/0149897 A1* | 6/2007 | Ghesquiere et al. .......... 600/583 |
| 2007/0173741 A1 | 7/2007 | Deshmukh et al. |
| 2007/0179406 A1 | 8/2007 | DeNuzzio et al. |
| 2008/0009768 A1 | 1/2008 | Sohrab |
| 2008/0021346 A1 | 1/2008 | Haar et al. |
| 2008/0200887 A1* | 8/2008 | Haar et al. .................... 604/322 |
| 2008/0269791 A1 | 10/2008 | Hoenes et al. |
| 2009/0099477 A1 | 4/2009 | Hoenes et al. |
| 2009/0259146 A1 | 10/2009 | Freeman et al. |
| 2010/0174211 A1 | 7/2010 | Frey et al. |
| 2010/0234869 A1 | 9/2010 | Sacherer |

FOREIGN PATENT DOCUMENTS

| | | | |
|---|---|---|---|
| EP | 1 360 934 A1 | 11/2003 | |
| EP | 1 360 935 A1 | 11/2003 | |
| EP | 1 402 812 A1 | 3/2004 | |
| EP | 1491143 A1 * | 12/2004 | ............... A61B 5/15 |
| EP | 1 508 304 A1 | 2/2005 | |
| EP | 1 880 671 A1 | 1/2008 | |
| EP | 2 042 098 A1 | 4/2009 | |
| JP | 2005185378 A | 7/2005 | |
| WO | WO 03/070099 A1 | 8/2003 | |
| WO | WO 2005/006939 A2 | 1/2005 | |
| WO | WO 2005/016125 A2 | 2/2005 | |
| WO | WO 2005/033659 A2 | 4/2005 | |
| WO | WO 2005/065415 A2 | 7/2005 | |
| WO | WO 2005/121759 A2 | 12/2005 | |
| WO | WO 2007/060004 A1 | 5/2007 | |
| WO | WO 2007/084367 A2 | 7/2007 | |
| WO | WO 2008/145625 A2 | 12/2008 | |
| WO | WO 2009/037192 A1 | 3/2009 | |

OTHER PUBLICATIONS

U.S. Appl. No. 12/235,891 to Hoenes et al., Final Office Action mailed Aug. 16, 2010.
U.S. Appl. No. 12/235,891 to Hoenes et al., Office Action mailed Mar. 15, 2010.
International Application No. PCT/EP2010/005668 International Search Report and Written Opinion mailed Mar. 16, 2011.
U.S. Appl. No. 12/568,009 to Roe et al., Office Action mailed Apr. 24, 2012.

* cited by examiner

PC50 Morphological (Tip Dose) Blood Transfer Techniques

BODY FLUID LANCING, ACQUIRING, AND TESTING CARTRIDGE DESIGN

CROSS-REFERENCE TO RELATED APPLICATIONS

This application is a continuation-in-part of U.S. application Ser. No. 12/568,009, filed Sep. 28, 2009, which is hereby incorporated by reference. This application is a continuation-in-part of International Patent Application No. PCT/EP2008/062130, filed Sep. 12, 2008, which claims the benefit of U.S. Provisional Application No. 60/972,996, filed Sep. 17, 2007, which are hereby incorporated by reference.

BACKGROUND

The present invention generally relates to an integrated disposable cartridge and more specifically, but not exclusively, concerns a cartridge manufactured in a cost-effective manner. Moreover, the integrated disposable includes a unique technique of transferring a fluid sample from a lancet to a test section.

The present invention also generally concerns a disposable device for analyzing body fluid especially for blood sugar tests comprising a container which can be inserted into a measuring apparatus, a sampling member provided in the container to pierce skin of a body part and sample body fluid, and a test member for receiving body fluid obtained by the skin-piercing. The invention further concerns an according analyzing process.

The acquisition and testing of body fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various body fluids and, for certain applications, is particularly related to the testing of blood and/or interstitial fluid. Performing home-based testing can be difficult for many patients, especially for patients with limited hand dexterity, such as the elderly or diabetics. For example, diabetics can sometimes experience numbness or tingling in their extremities, such as their hands, which can make self-testing difficult because they are unable to accurately position a test strip to collect the blood sample. In addition, wounds for diabetics tend to heal more slowly, and as a result, there is a desire to make incisions less invasive.

Various methods and withdrawal devices for small amounts of body fluids are used above all by diabetics for the self-monitoring of blood sugar which should be carried out several times daily. Recent concepts envisage a microneedle including a test element as a disposable in a hand-held device to generate a skin puncture, to remove a small amount of blood therefrom utilizing capillary forces and to analyse this blood sample. Generally, in such devices the lancing member and the test element are monolithically integrated and must be handled as combined units, where the lancing and blood transfer require separate actuation.

Recently, lancet integrated test strips or elements have been developed in which a test strip is integrated with a lancet or other piercing means so as to form a single disposable unit. While these integrated units have somewhat simplified the collection and testing of fluid samples, there are still a number of issues that need to be resolved before a commercial unit can be implemented. A few concerns for a multiple disposable unit include manufacturing the unit simply and inexpensively and positioning individual lancets and test strips in the commercial unit without damage to either the test strip or the lancet. Typically, a plurality of lancets and a plurality of test strips are each individually positioned in sealed compartments in a commercial unit. This process can be time consuming, expensive, and difficult to manufacture. Moreover, there is a possibility some of the lancets and/or test strips can be damaged while being positioned in the commercial unit.

Another concern of multiple disposable units disposed in a commercial unit is sterility of the lancets both initially and to maintain the sterility of the lancets until lancing the skin or tissue. As should be appreciated, sterilizing the lancets separately from the test sections eases the manufacturing process of a commercial unit. For example, the chemistry on the test sections is not disturbed by the separate sterilization of the lancets. After the lancets and test sections are assembled together, it is important to maintain the sterility of the lancets until lancing the skin or tissue to ensure an accurate testing event.

Yet another concern of multiple disposable units disposed in a commercial unit is the alignment of the lancet and test strip. Properly aligning the lancet and test strip ensures an accurate transfer of a body fluid sample from the lancet to the test strip. Moreover the proper alignment of the lancet and test strip reduces waste of the body fluid sample by accurately transferring the sample from the lancet to the test strip.

Another concern of users of multiple disposable units is the preference for smaller body fluid sample sizes that are used for testing, preferably a volume less than 1 microliter. Typically, a small body fluid sample requires a small penetration depth by the lancet which reduces the amount of pain for the user during lancing. Further, it is desirable that there is minimal or very little waste of body fluid from the lancet that is transferred to the test strip. Unnecessary waste of body fluid during the transfer of the body fluid from the lancet to the test strip can result in inaccurate test results or the need for larger body fluid samples to yield an accurate test result. There is a need for a multiple disposable unit that reduces the amount of pain for the user during lancing by using a lancet having a small penetration depth. Moreover there is a need for a multiple disposable unit that also efficiently transfers the small body fluid sample from the lancet to the test strip to eliminate any waste of body fluid.

A precise lancing profile for a lancet in an integrated disposable cartridge ensures an appropriate amount of a body fluid sample is collected during lancing the skin or tissue. A precise lancing profile for a lancet also ensures that an appropriate number of capillaries are cut during lancing the skin or tissue. For example, if too few capillaries are cut then the body fluid sample may not be large enough to yield accurate test results. If too many capillaries are cut then an overly large body fluid sample is collected and the user may experience a greater amount of pain than was necessary to obtain an adequate body fluid sample. Various configurations of the lancet and lancet entry have been used to attempt to solve these concerns. One configuration is a substantially straight lancet with a straight entry. One concern with a straight lancet having a straight entry is the deep penetration depth of the lancet which results in many capillaries being cut and a greater amount of pain for the user. Another configuration is a curved lancet with a rotational entry which can also result in an overly large wound and fluid sample and unnecessary pain for the user.

Thus, there is a need for improvement in this field.

SUMMARY

One aspect concerns an integrated cartridge assembled by dropping or placing the components into a frame. The integrated cartridge includes a test ring having a continuous strip of chemistry such that the test ring is sectionable into a plurality of test sections when the test ring is positioned in the frame. The integrated cartridge also includes a lancet wheel having a lancet rim with a plurality of lancets extending radially inward from the lancet rim. Each of the lancets has a leg portion, a contact portion to contact the test section and to deposit a body fluid sample on the test section, and a lancet tip extending substantially transverse to the leg portion. The integrated cartridge includes a frame having an egg crate shape with a plurality of chambers to facilitate drop-in assembly of the lancet wheel and the test ring onto the frame and to section the test ring into the plurality of test sections such that each of the lancets is positioned next to one test section in the frame.

Another aspect concerns a method of assembling an integrated disposable cartridge. The method includes assembling an integrated disposable cartridge by dropping a lancet wheel onto a frame. The lancet wheel has a rim with a plurality of radially inwardly extending lancets and the frame has a plurality of spokes defining a plurality of chambers. Each of the lancets is positioned in one of the chambers.

Another aspect concerns a method of automatically collecting a body fluid sample with a lancet and transferring the body fluid sample to a test strip. An integrated disposable cartridge includes a frame, a lancet wheel having a plurality of lancets extending radially inward from a rim, and a test ring having a plurality of test sections, wherein the plurality of lancets contact the plurality of test sections. Next, an incision in tissue is formed with one of the lancets by rotating the lancet away from the plurality of test sections. A body fluid sample is collected with a capillary groove on the lancet, and the lancet is withdrawn from the incision in tissue by rotating the lancet towards the plurality of test sections. The body fluid sample in the capillary groove on the lancet is transferred to one of the test sections by contacting the test section with the lancet to release the body fluid sample.

Yet another aspect concerns a microsampler wheel. The microsampler wheel includes a base, a plurality of lancets, and a plurality of ribs. The plurality of ribs and the plurality of lancets extend radially outward from the base, and the plurality of ribs and the plurality of lancets alternate with each other. Each of the lancets includes a curved lancet tip configured to form an incision in skin. Each of the lancets is also configured to rotate about the base such that the curvature of the rotation of the lancet is similar to the curvature of the lancet tip. Each of the plurality of ribs is positioned as a reference plane for determination of the penetration depth of the lancet tip.

Further forms, objects, features, aspects, benefits, advantages, and embodiments will become apparent from a detailed description and drawings provided herewith.

DESCRIPTION OF SELECTED EMBODIMENTS

Figure 1:
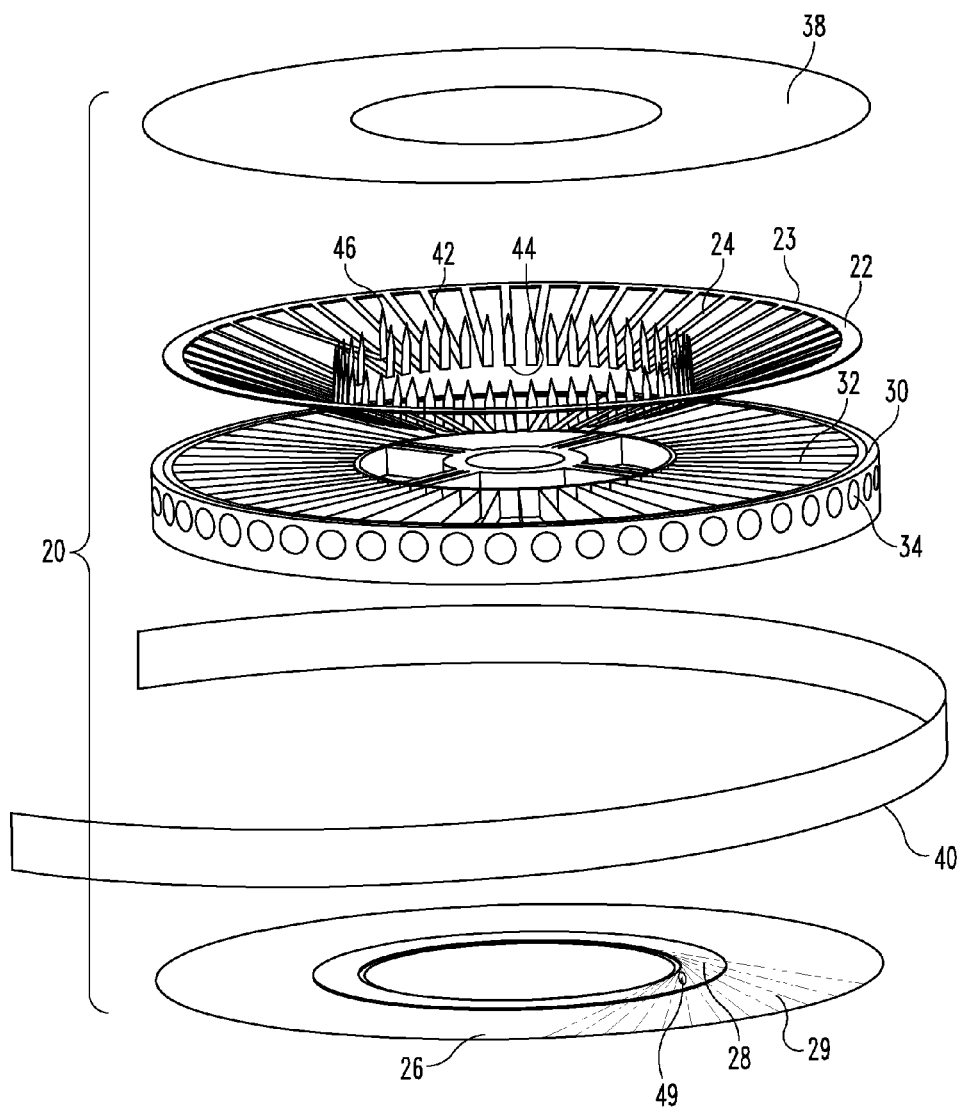
FIG. 1 is an exploded perspective view of an integrated disposable cartridge.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the invention may not be shown for the sake of clarity.

Any directional references in this detailed description with respect to the Figures, such as up or down, or top or bottom, are intended for convenience of description, and by itself does not limit the present invention or any of its components to any particular positional or spatial orientation.

One embodiment concerns a unique integrated disposable cartridge or disc as well as a technique for inexpensively manufacturing the cartridge or disc, which is by virtue of the design. The unique cartridge utilizes a unique "drop-in" or "modular" design that allows a plurality of lancets on a lancet wheel to be aligned in sample chambers of a disc-shaped frame. This unique drop-in design eliminates the need for individual alignment and placement of the plurality of lancets. A test ring is also positioned on the frame such that the sample chambers form a plurality of test elements on the test ring. As should be appreciated, the lancet wheel, frame, and test ring are manufactured separately and assembled to form an integrated disposable cartridge. In one form, the lancet wheel, frame, and test ring are sterilized after assembly of the cartridge. In another form, the lancet wheel, frame, and test ring are sterilized individually. One or more sealing foils or sheets positioned on the exterior of the cartridge maintain the sterility of the lancets and humidity of the test elements prior to lancing the skin or tissue. The cartridge protects other persons from unintended contact of used lancets after lancing the skin or other tissue. The cartridge includes individual, separate chambers to maintain the humidity of the chemistry on each of the test elements prior to lancing the skin or tissue. The unique shape of the lancets and the placement of the test elements on the frame enable automatic transfer of a body fluid sample from the capillary of the lancet to a test element immediately after a lancing and sampling cycle has occurred. The automatic transfer of the body fluid sample enables a "one step" operation of lancing, sampling, and testing of the body fluid sample. Moreover, the lancet is configured to collect a small volume of body fluid, such as less than 0.1 microliter, and transfer this small volume to the test section for analysis without considerable loss of fluid. As should be appreciated, the one step operation and small size of the cartridge and associated meter provides for on-the-go convenience for users.

A second embodiment also concerns a unique integrated disposable cartridge or disc as well as a technique for inexpensively manufacturing the cartridge or disc. The cartridge in this embodiment utilizes a unique lancet wheel design that includes a plurality of microneedles or lancets that alternate with a plurality of ribs. The cartridge includes a test element disc that has a plurality of test elements positioned next to the plurality of lancets. The lancet wheel and the test element disc are manufactured separately and assembled together to form the cartridge. Together the lancet wheel and the test element disc define a plurality of individual lancing and testing events. The lancets have a unique built-in spring shape and the lancet tip forms a slight circular path during lancing. The unique shape of the lancets provides that the lancets spring back or return to their original pre-incision position after lancing the skin or tissue. Moreover, each of the plurality of lancets includes a curved lancet tip corresponding to the curvature of the circular path traced by the lancet tip during the bending and retraction during a lancing cycle of the lancet. The curved shape of the lancet matching a curved trajectory path mimics the straight line motion typical in most common lancing systems. A drive mechanism that forces the lancet tip to follow a curved path during penetration and retraction follows the natural bending or flexing of the lancet arm's radius length and enhances simplicity of design and manufacture of the disposable. As should be appreciated, the return of the contaminated lancet to the pre-incision or un-flexed position protects other persons from accidentally contaminating themselves with a used lancet. Each of the lancet tips includes a micro-capillary sized to collect a body fluid sample via capillary action. The capillary is positioned on the front or rear face of the lancet tip, and the capillary can extend various lengths from the lancet tip along the lancet. The plurality of test elements is positioned next to the capillaries on the lancets such that as the lancet tip returns to its pre-incision position, the body fluid sample in the capillary is transferred from the capillary to the test element.

Figure 2:
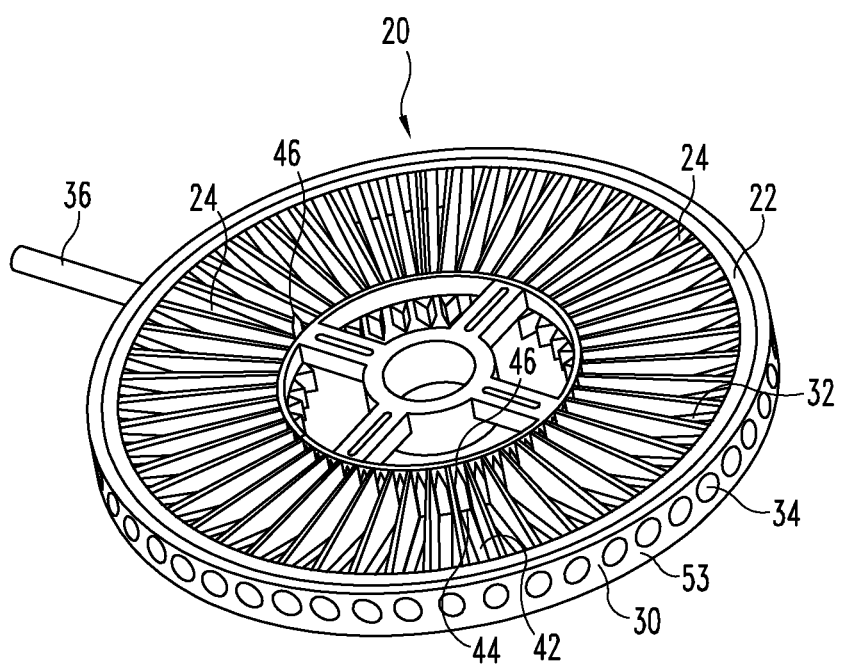
FIG. 2 is a top perspective view of the FIG. 1 cartridge.
Figure 3:
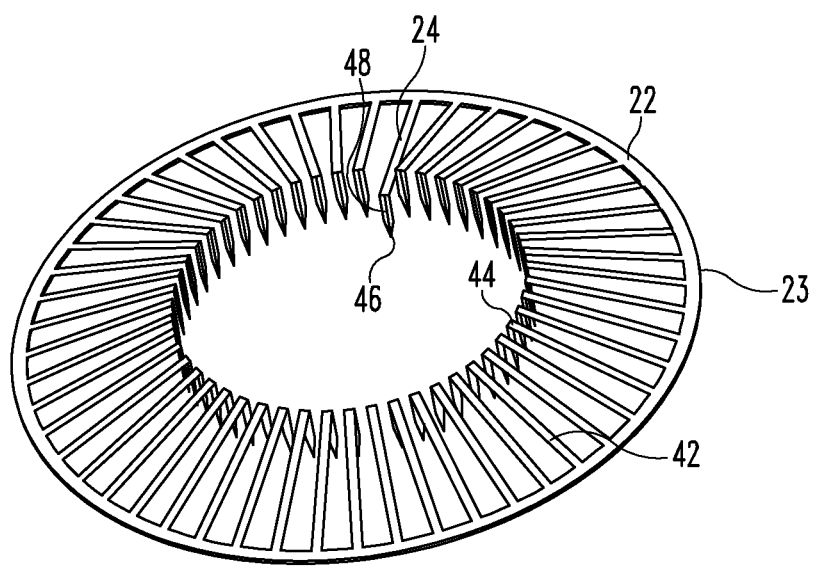
FIG. 3 is a bottom perspective view of a lancet wheel that is incorporated into the FIG. 1 cartridge.
Figure 4:
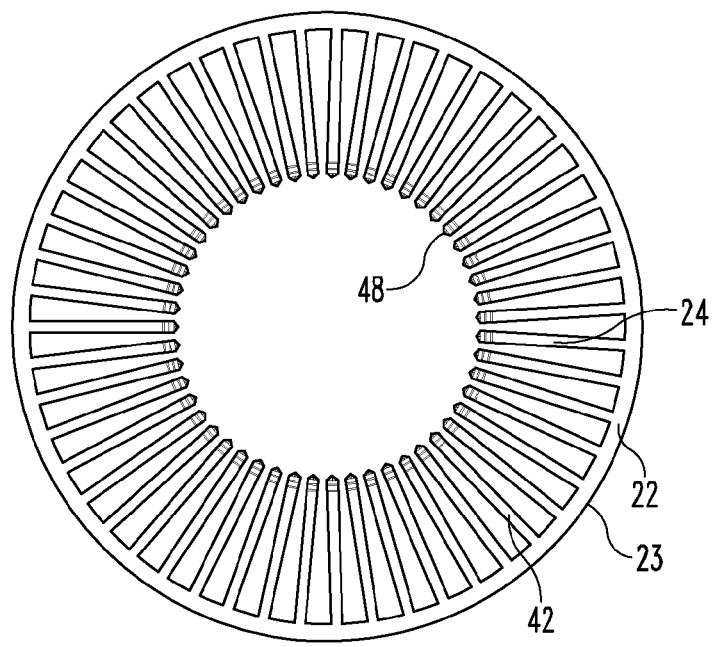
FIG. 4 is a top view of the FIG. 3 lancet wheel.
Figure 5:
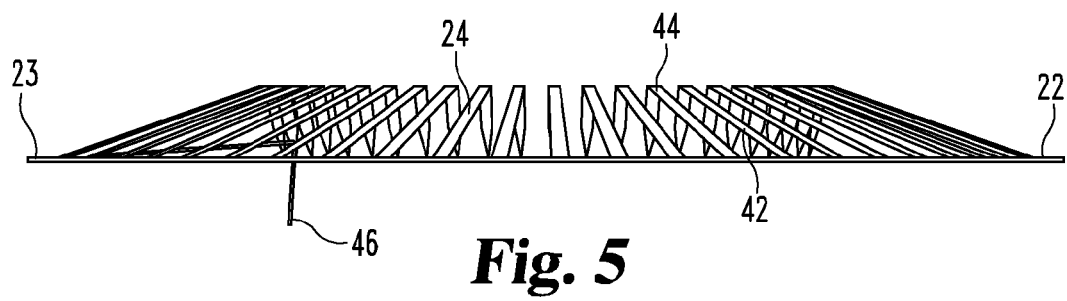
FIG. 5 is a side view of the FIG. 3 lancet wheel.

A cartridge 20 according to one embodiment is illustrated in FIGS. 1 and 2. The cartridge 20 is configured to lance skin to form an incision, collect a body fluid sample from the incision, analyze the body fluid sample, and be indexed for a subsequent lancing. The cartridge 20 forms a sterile environment for a plurality of lancets and a plurality of test elements, and the cartridge 20 maintains the low humidity of the chemistry independently for each of the plurality of test elements prior to lancing the skin or tissue. The individual elements or modular components of the cartridge 20 are manufactured separately and assembled into the final form. For example, in one embodiment, the cartridge 20 includes twenty-five or more lancing and testing modules by assembling five or six components to form cartridge 20. Moreover, there is no user input required to transfer the body fluid sample from the lancet to the test strip as the cartridge 20 performs this task automatically after an incision in skin is formed. The cartridge 20 also stores the used lancets and test elements after lancing and testing to prevent meter contamination and/or cross contamination between the individual lancets and test elements contained in the cartridge 20. As shown, the cartridge 20 is in the shape of a disc or circle that enables indexing by rotation of the cartridge 20 and minimizes the size of cartridge 20 when it is stored in a meter. It should be appreciated that the cartridge 20 can have a different overall shape in other embodiments. For example, the cartridge 20 can be oval, square, or rectangular, to name a few shapes.

The cartridge 20 includes a lancet wheel 22 with a plurality of lancets 24 for lancing the skin and collecting the body fluid sample and a test ring 26 having a continuous test area that is divided into a plurality of test sections 28 for analyzing the body fluid sample when the test ring 26 is assembled to a frame 30. The cartridge 20 also includes a frame 30 that defines a plurality of chambers or compartments 32 for storing the individual lancets 24 in a sterile manner. As described in more detail below, the cartridge 20 can include a breachable sterility sheet 40 to seal the individual lancets 24. The plurality of chambers 32 aligns each of the test sections 28 with an individual lancet 24. The frame 30 is similar to an egg crate design that allows for quick assembly of the lancet wheel 22 with the frame 30 with drop-in or modular design of the lancet wheel 22 into the plurality of compartments 32. The frame 30 also defines a plurality of openings 34 sized to receive a driver 36. Each of the chambers 32 aligns with one of the openings 34 on the frame 30. The driver 36 is sized and configured to extend through one of the openings 34 and into the corresponding one of the chambers 32 to engage and move the lancet 24 to form an incision in skin. The driver 36 can be semi or fully automatic in function, and the driver 36 can be part of an indexing and/or actuation system as described below. The driver 36 includes a sharp or pointed end to pierce through a second sterility sheet 40 placed over the openings 34, as described below. The cartridge 20 includes a first sterility sheet 38 positioned to cover and seal one side of the plurality of chambers 32 of frame 30. The cartridge 20 also includes a second breachable sterility sheet 40 positioned to cover and seal the plurality of openings 34 of the frame 30. The test ring 26 is configured to cover and seal the remaining side of the plurality of chambers 32 of frame 30. The combination of the first sterility sheet 38, the second sterility sheet 40, and the test ring 26 over the plurality of chambers 32 and the plurality of openings 34 maintains the sterility of the plurality of lancets 24 and controls the humidity to which the plurality of test sections 28 are subjected. Example materials for the first sterility sheet 38 and the second sterility sheet 40 include plastic, metal, paper, and/or other materials. In one embodiment, the first sterility sheet 38 and the second sterility sheet 40 are each made of aluminum-coated polyethylene terephthalate having a thickness of less than 12 micrometers. Furthermore, in this embodiment, the test ring 26 is made of polyethylene-coated polyethylene terephthalate having a thickness of less than 125 micrometers. As should be appreciated, the first sterility sheet 38, the second sterility sheet 40, and the test ring 26 can be made of other materials.

As illustrated in FIGS. 3, 4, 5, and 6, the lancet wheel 22 includes a lancet rim 23 with the plurality of lancets 24 extending radially inwardly from the lancet rim 23. In other words, the plurality of lancets 24 extend from the lancet rim 23 towards the center of the lancet wheel 22.

Figure 6:
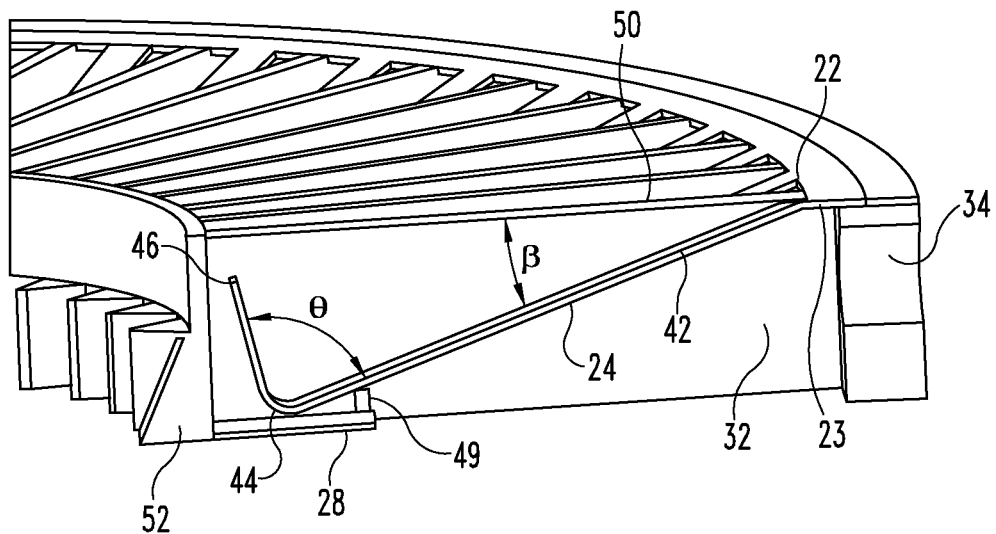
FIG. 6 is an enlarged, cross-sectional view of the FIG. 1 cartridge.

Each of the lancets 24 has a flexible leg portion 42, a contact portion 44, and a lancet tip 46. The leg portion 42 is substantially straight; however, in another form, the leg portion 42 may be curved or bent or otherwise designed to provide a spring-like link. The leg portion 42 extends from the lancet rim 23 to the contact portion 44. The contact portion 44 forms a first angle θ between the leg portion 42 and the lancet tip 46 as shown in FIG. 6. In one embodiment, the first angle θ is approximately a 90 degree angle. In other embodiments, the first angle θ may be another angle between 0 and 270 degrees. The lancet 24 is configured such that the contact portion 44 is positioned to contact one test section 28. The leg portion 42 forms a second angle β with the edge of a wall 50 of the frame 30, as described in more detail below. As shown in FIG. 6, the second angle β is an acute angle.

The lancet tip 46 defines a capillary groove 48 sized to draw a body fluid sample via capillary action and to collect the body fluid sample. In one embodiment, the capillary groove 48 is coated with a hydrophilic material to enhance the capillary action of the groove 48. The capillary groove 48 may be located on either the front side or the back side of the lancet tip 46. The capillary groove 48 may be an open, closed, or combination open and closed capillary in which to draw the body fluid sample. Typically, the capillary groove 48 is located on the inside face of the lancet tip 46 and is an open capillary. As should be appreciated, an open capillary is easier to manufacture because the open capillary can be easily formed. For example, the open capillary can be formed by etching the surface of the lancet tip 46 and removing material to create the open capillary. Moreover, an open capillary groove collects body fluid that is drawn from beneath the skin surface below the incision. The capillary groove 48 extends from the lancet tip 46 into the contact portion 44 such that as the contact portion 44 contacts the test section 28, the body fluid sample contained in the capillary groove 48 is released by fluid contact onto the test section 28. The capillary grooves 48 in the plurality of lancets 24 may be manufactured by stamping, etching, carving, or combinations thereof including other techniques.

The lancet wheel 22 having the plurality of lancets 24 can be manufactured from a single piece of material, such as metal, plastic, or combinations thereof including other materials. In one embodiment, the lancet wheel 22 is formed by etching, stamping, or laser cutting a metal plate and removing portions of the metal plate to expose the plurality of lancets 24. The capillary grooves 48 are formed by etching, laser cutting, or forming the plurality of lancet tips 46 to expose the capillary grooves 48 either simultaneously with the formation of the plurality of lancets 24 or subsequent to the formation of the lancets 24. Each of the plurality of lancets 24 is bent at the contact portion 44 to form the first angle θ and each of the plurality of lancets 24 is bent at the rim 23 to form the second angle β. Each of the plurality of lancets 24 radiates from the rim 23 to the center of the lancet wheel 22. In another embodiment, the lancet wheel 22 can be manufactured by attaching the plurality of lancets 24 to the rim 23. It should be appreciated in other embodiments, the lancet wheel 22 is formed by other manufacturing techniques.

As mentioned previously and illustrated in FIG. 1, the test ring 26 includes the plurality of test sections 28 for testing body or biological fluids, such as blood, interstitial fluid, as well as other fluids, from the incision. The test section 28 for the embodiment of FIGS. 1 and 2 will be described with reference to an optical test strip, but it should be recognized that the test section 28 can analyze body fluid samples in other manners, such as via amperometry, coulometry, or reflectance photometry, to name a few techniques. As should be recognized, the optical test strip can be analyzed via a charge-coupled device (CCD) and/or color-capture device, and a histogram reader can be used to display the test results.

In the illustrated embodiment, the plurality of test sections 28 is in the form of a continuous strip or ring of chemistry mounted on or applied to a film. In FIG. 1, the test ring 26 includes index lines 29 printed on it to distinguish the individual test sections 28; however, in other embodiments the index lines 29 are optional. Each of the test sections 28 is located in one of the chambers 32 and positioned adjacent to and/or in contact with the contact portion 44 of one of the lancets 24. Friction or rubbing between the contact portion 44 of the lancets 24 and the test sections 28 prior to a lancing and testing event can damage the chemistry on the test sections 28 and affect the analysis of the body fluid sample. In this embodiment, the plurality of test sections 28 include a thin, soluble layer to protect the chemistry on the plurality of test sections 28 and to prevent testing errors from the friction or rubbing of the contact portion 44 of the lancet 24 with the chemistry on the plurality of test sections 28 prior to a lancing and testing event. This thin, soluble layer does not interfere with the chemistry or affect the analysis results of the body fluid sample during a lancing and testing event. In another embodiment, each of the test sections 28 does not contact the contact portion 44; instead a breakable tab 49 is positioned between the lancet 24 and the test section 28 to elevate the contact portion 44 away from the test section 28. The breakable tab 49 remains in position until the driver 36 engages the leg portion 42 of the lancet 24. The test ring 26 is configured to cover and seal one side of the frame 30 and the corresponding side of the plurality of chambers 32. In one embodiment, the test ring 26 includes a chemistry lot coding in a bar code or radio frequency identification (RFID) chip to store information on the calibration for the chemistry lot in a convenient format for the plurality of test sections 28.

Figure 7:
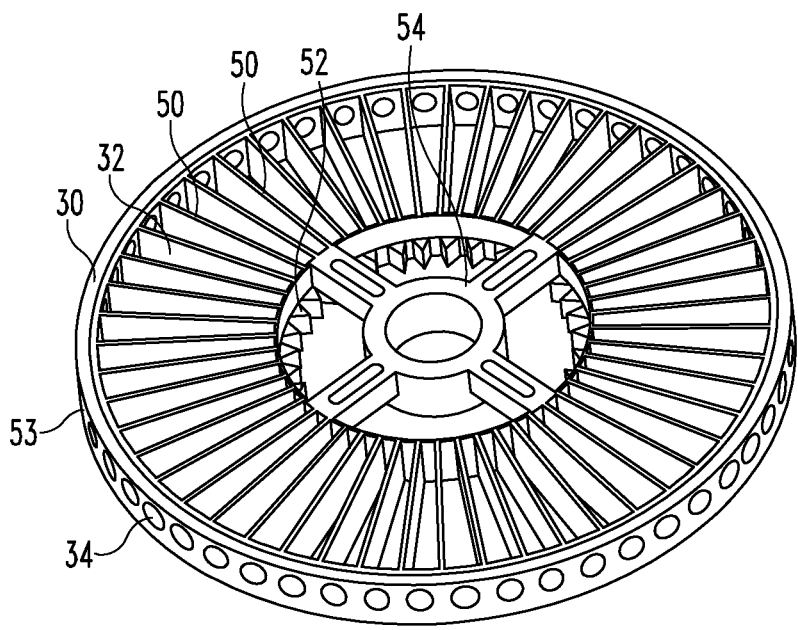
FIG. 7 is a perspective view of a frame used in the FIG. 1 cartridge.

As illustrated in FIGS. 1, 2, and 7, the frame 30 includes a plurality of spokes or walls 50 configured to define the plurality of chambers 32 in which each of the chambers 32 is sized to house one of the lancets 24. The plurality of walls 50 segregate the plurality of lancets 24 and maintain the sterility of the plurality of lancets 24. Moreover, since the lancets 24 return to their original pre-incision forming position in the chambers 32, the plurality of walls 50 prevent contamination of sterile lancets 24 by preventing contact between used and unused (sterile) lancets. The frame 30 is circular in shape, and each of the chambers 32 is a trapezoidal or wedge-like shape. In one form, the frame 30 is approximately 38 millimeters diameter, 3-5 millimeters height, and includes twenty-five chambers to store twenty-five of the lancets 24 and twenty-five of the test sections 28. In other forms, the frame 30 and the chambers 32 may be shaped differently. For example, the frame 30 and/or the chambers 32 can have a rectangular, oval, and/or triangular shape.

As illustrated in FIGS. 2 and 7, the frame 30 also includes a plurality of internal gears 52 located near the center of the frame 30. Each of the internal gears 52 is positioned near one of the chambers 32. The placement of the gears 52 next to the chambers 32 enables a spindle or other engagement mechanism to engage the gears 52 and rotate the frame 30 to position a subsequent chamber 32 and corresponding opening 34 in line with the driver 36. The gears 52 may be positioned at other locations on the frame 30, and the gears 52 may be configured differently to engage other rotational mechanisms in other embodiments. Each of the plurality of internal gears 52 is triangular in shape; however, in other embodiments the plurality of internal gears 52 may be shaped differently. For example, the plurality of internal gears 52 can have a circular, rectangular, and/or oval shape. In another example, the plurality of internal gears 52 index the cartridge 20 to provide only one way in which to insert the cartridge 20 into a meter 66, as discussed below.

The frame 30 also includes a frame rim 53 on the exterior, and a hub 54 on the interior, as illustrated in FIGS. 2 and 7. The frame rim 53 defines the plurality of openings 34 such that each of the openings 34 corresponds with one of the chambers 32. Each of the openings 34 is circular in shape; however, in other embodiments the openings 34 may be shaped differently. For example, each of the openings 34 can have an oval, elliptical, and/or rectangular shape, to name a few shapes. In another example, each of the openings 34 is open to the bottom of the frame 30 to provide for easier molding of the frame 30. Moreover, each of the openings 34 is sized to receive the driver 36. The hub 54 is circular in shape for mounting the frame 30 onto a spindle or other rotatable mechanism. The hub 54 can be shaped differently in other embodiments.

In one embodiment, the frame 30 is constructed from desiccant-filled plastic which is injection molded into a disc shaped frame. In other embodiments, the frame 30 can be made from other materials such as metal, wood, ceramic, plastic, other materials, and/or composites thereof. In another embodiment, the frame 30 includes a separate desiccant wedge or desiccant granules added to each of the chambers 32. Moreover, the frame 30 can be constructed from other techniques such as attaching the plurality of walls 50 and the plurality of internal gears 52 to the hub 54 by gluing, welding, or some other mechanism for attachment. In one form, frame 30 is sterilized using an inline electron beam (e-beam) sterilization process. The frame 30 can be sterilized in other manners, such as via gamma radiation or ultraviolet sterilization techniques. Moreover, frame 30 can also be sterilized at any one of the various assembly stages.

Figure 8:
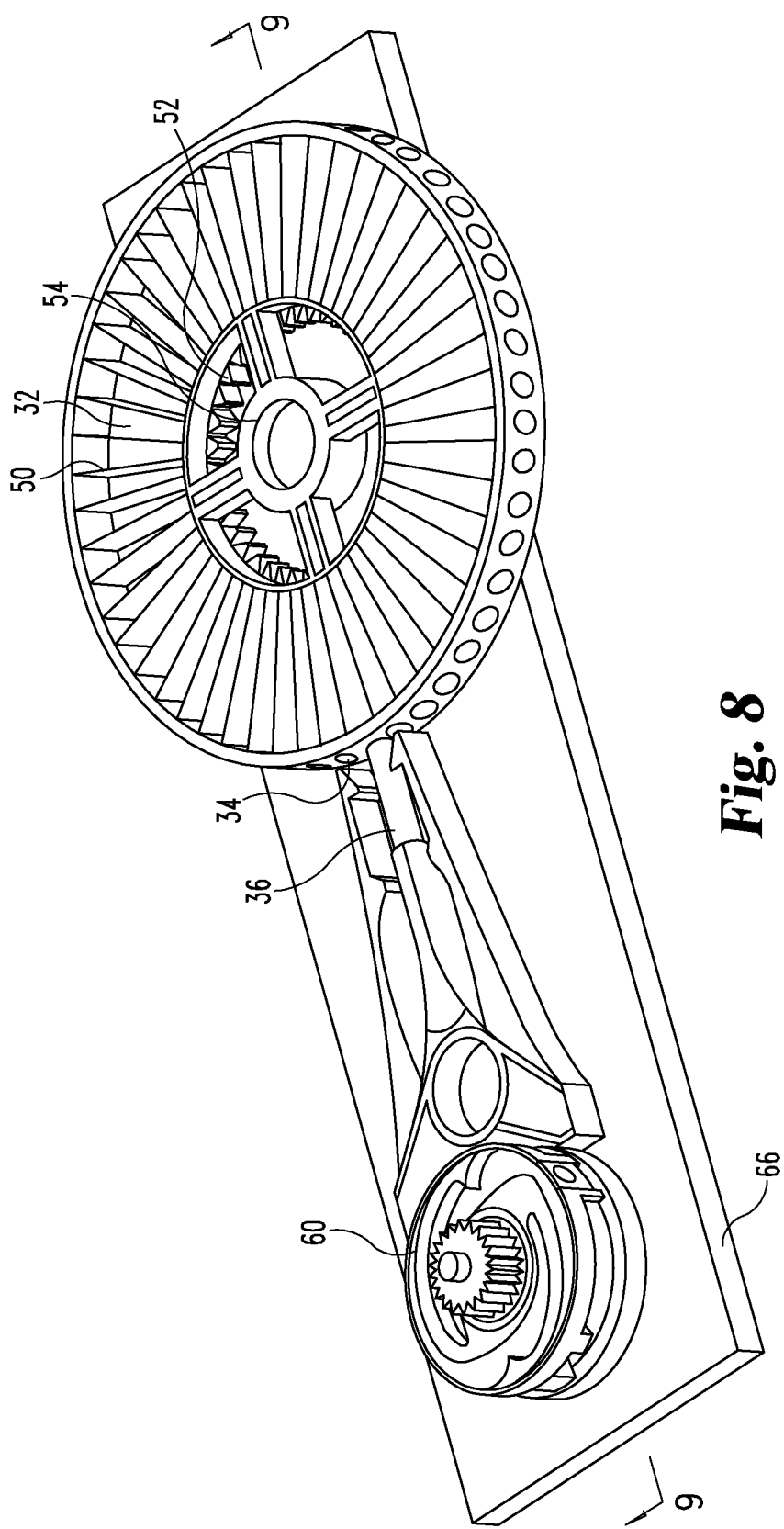
FIG. 8 is a bottom perspective view of the FIG. 1 cartridge loaded in a lancet driver mechanism.
Figure 9:
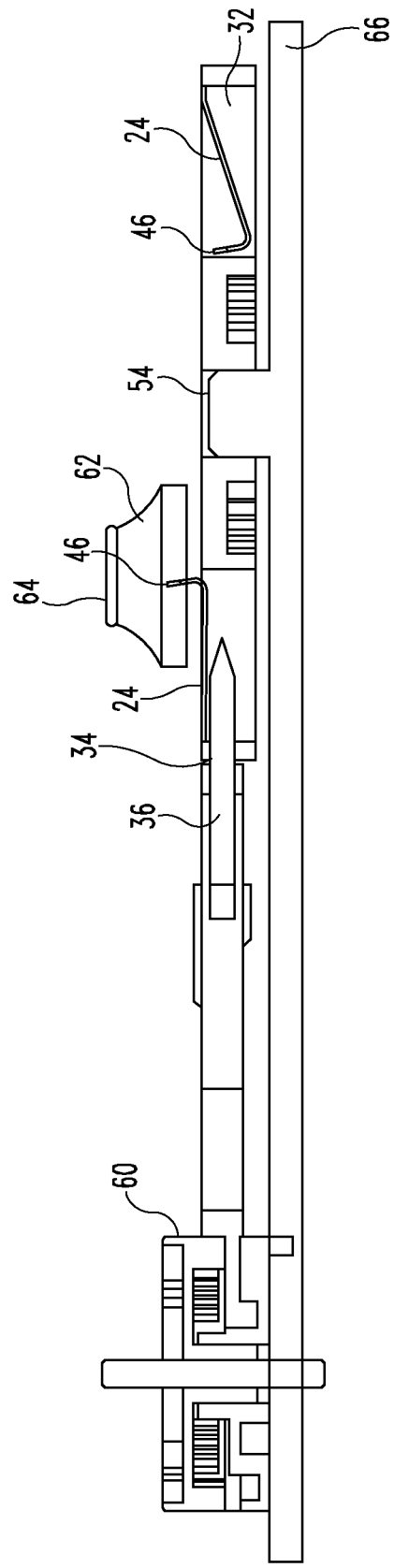
FIG. 9 is a cross-sectional view of the FIG. 8 mechanism.
Figure 10:
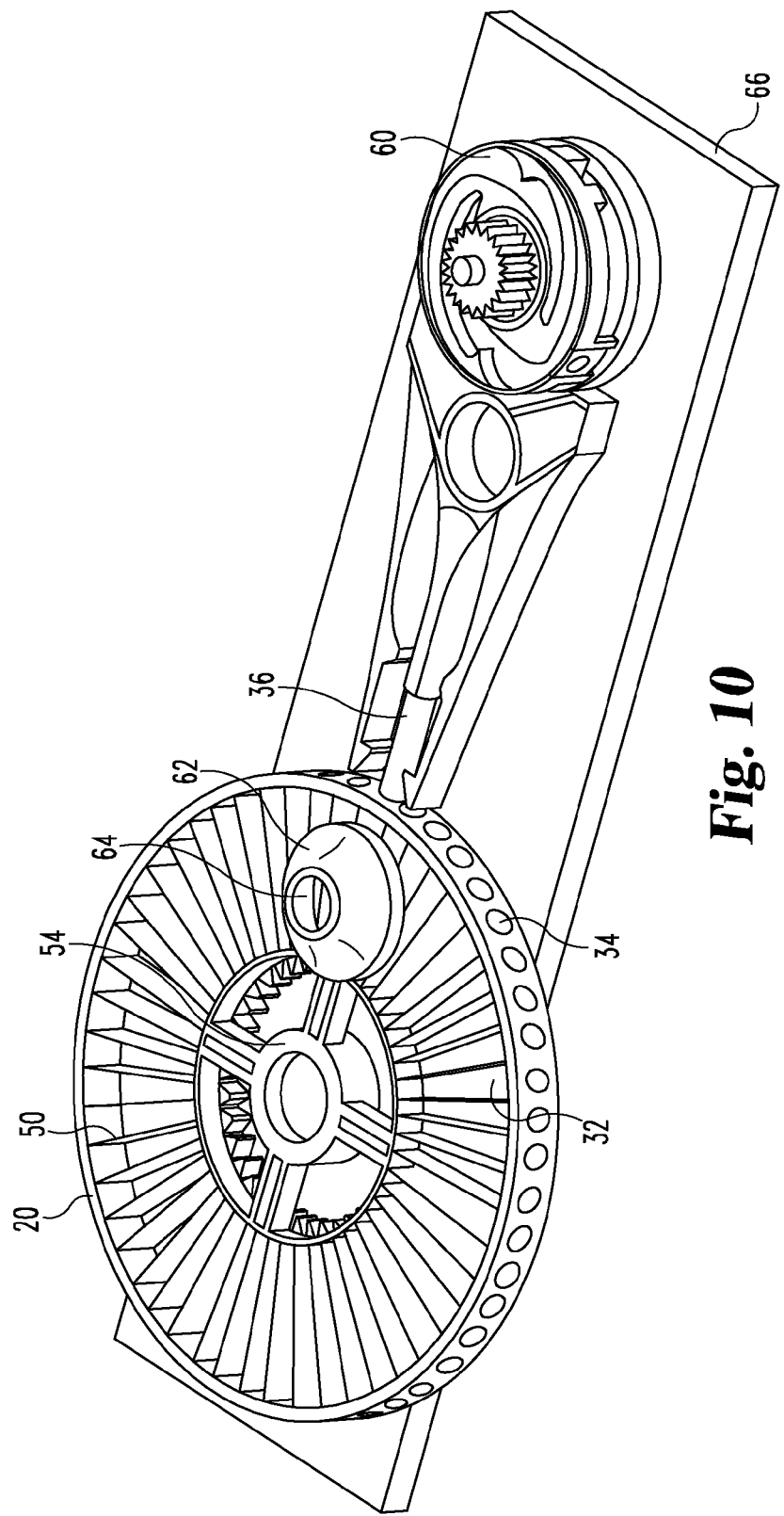
FIG. 10 is a top perspective view of the FIG. 8 mechanism that incorporates a lancing cap.
Figure 11:
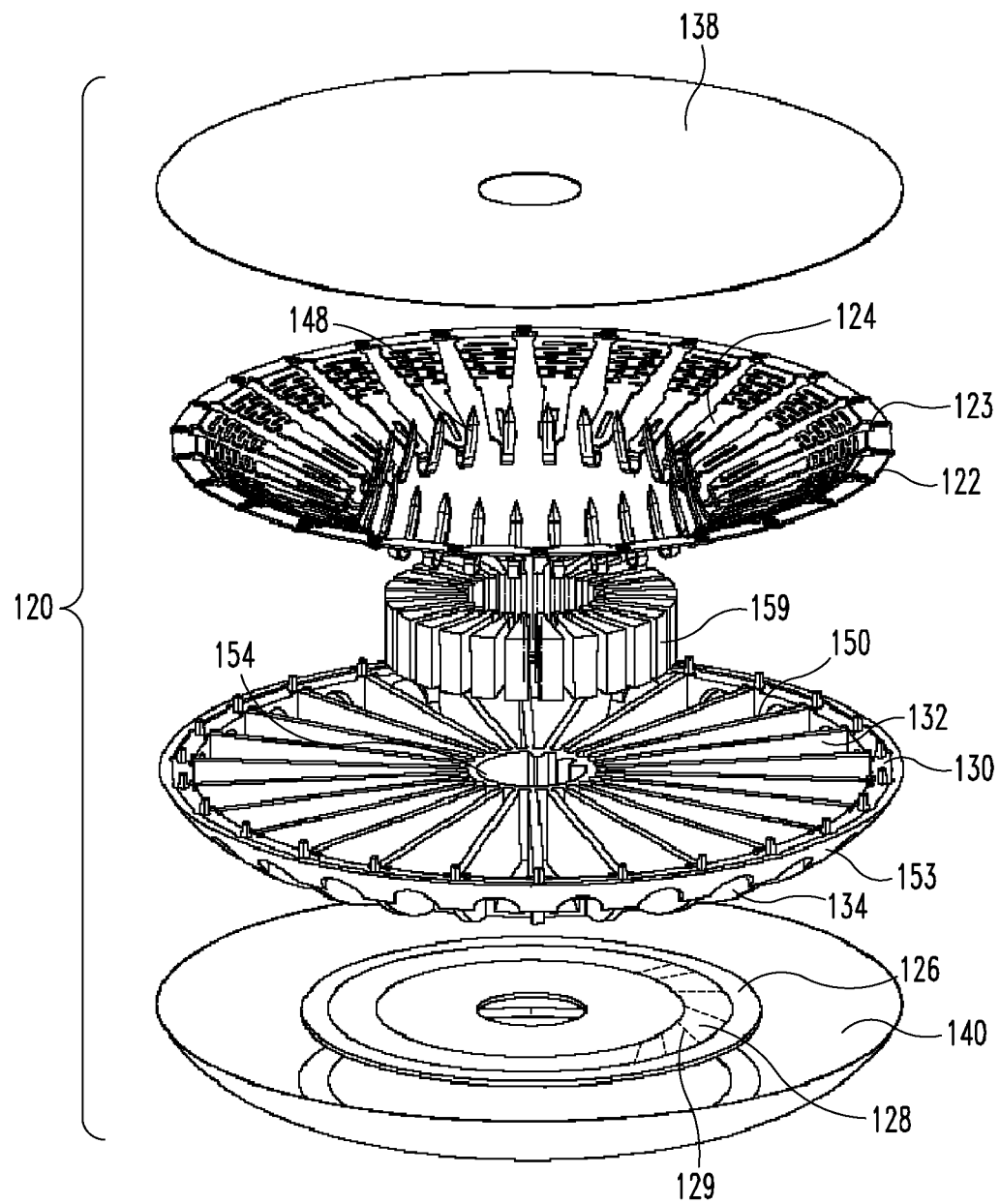
FIG. 11 is an exploded perspective view of an integrated disposable cartridge as viewed from the top of the integrated disposable cartridge.
Figure 12:
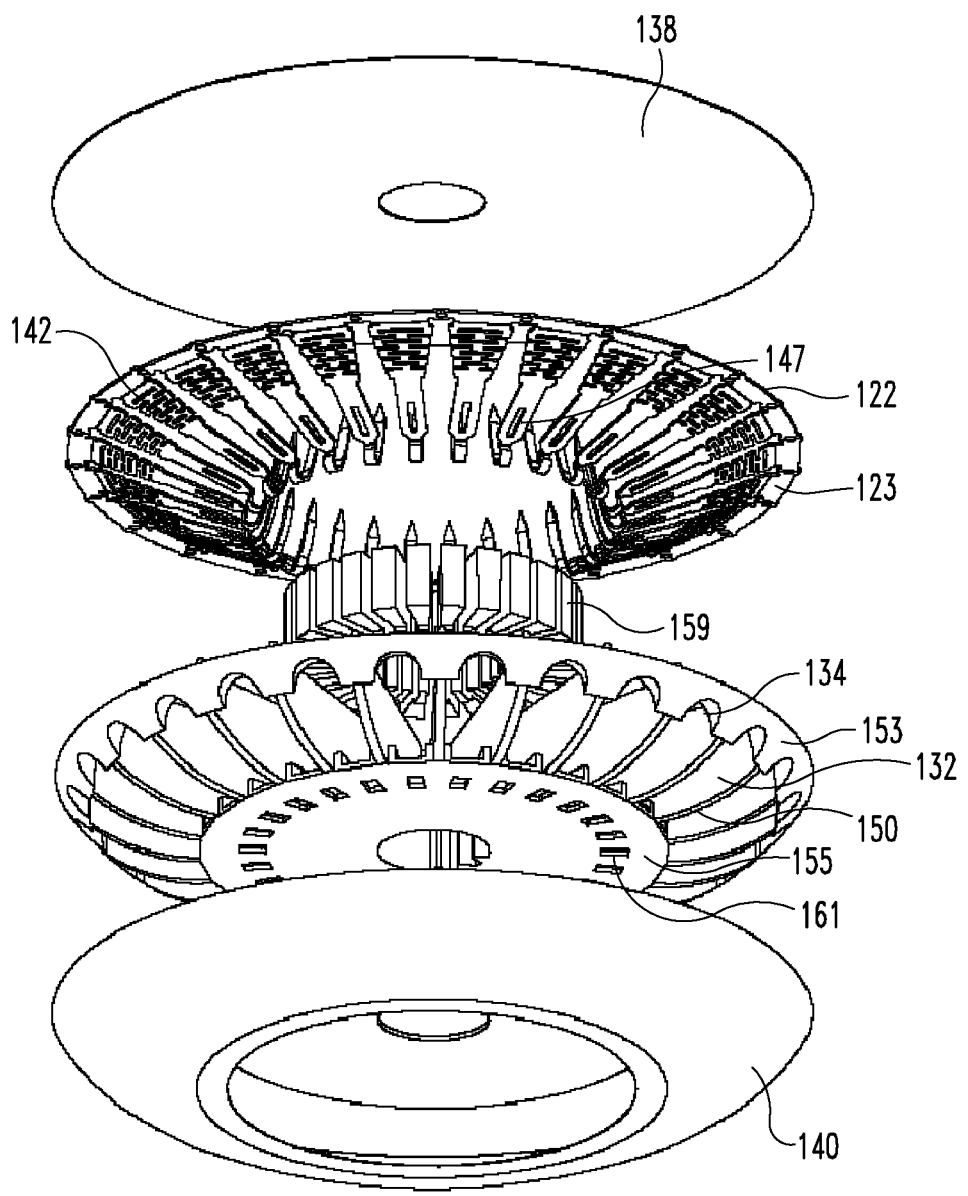
FIG. 12 is an exploded perspective view of the FIG. 11 integrated disposable cartridge as viewed from the bottom of the integrated disposable cartridge.

As illustrated in FIGS. 8, 9, and 10, the cartridge 20 is loaded into a meter 66. The meter 66 can be configured to display the analysis results of the body fluid sample. The meter 66 includes an actuation mechanism 60. In one embodiment, the actuation mechanism 60 engages and moves the driver 36 to engage one of the lancets 24. In another embodiment, the actuation mechanism 60 indexes the frame 30 to position the driver 36 adjacent the opening 34 of an unused lancet 24. As should be appreciated, in one embodiment, the actuation mechanism 60 engages and moves the driver 36 and the actuation mechanism 60 also indexes the frame 30. The meter 66 is not shown in its entirety, but it should be appreciated the meter 66 covers and encloses the cartridge 20, the driver 36, and the actuation mechanism 60. The meter 66 can be various shapes such as rectangular, triangular, circular, and/or oval, to name a few shapes. The meter 66 can be made of various materials, such as plastic, metal, and/or other materials.

In the embodiment illustrated in FIG. 10, the meter 66 includes a lancing cap 62 that is placed against the incision during lancing. The lancing cap 62 defines an incision location opening 64. As should be appreciated, the user places the appropriate body part that is to be lanced over the incision location opening 64 and the lancing tip 46 passes through the incision location opening 64 to form an incision in the user. The lancing cap 62 forms a tapered circular shape but can be shaped differently in other embodiments. For example, the lancing cap 62 can be pyramidal, U-shaped, ovoidal, circular, or some other shape. The incision location opening 64 is also circular in shape but can be shaped differently in other embodiments. The lancing cap 62 can be made of various materials, such as plastic, metal, and/or other materials.

In one embodiment, the lancing cap 62 is configured to adjust the penetration depth of the lancing tip 46. In one example, the lancing cap 62 is threaded into the meter 66. The threaded engagement allows the lancing cap 62 to move relative to the meter 66 in order to control the penetration depth of the lancing tip 46.

In another embodiment, the lancing cap 62 is configured to detect a force required by the user to initiate lancing. The lancing cap 62 can also control the skin deflection thru the lancing cap 62 to a known variation or depth. Further, the lancing depth can be controlled by the amount of travel of the driver 36 to engage the lancet 24 in which the range of motion of the driver 36 is set by the user. Additionally, the driver 36 may move in a linear radial motion, a rotational motion with an eccentric shape, or a tipping motion to lift up and down the flexible leg portion 42.

To use the cartridge 20, a user positions a body part to be lanced, most likely a finger, over the incision location opening 64. The driver 36 is actuated to pierce through the second sterility sheet 40, pass through the corresponding opening 34, and enter the chamber 32. The driver 36 continues moving into the chamber 32, and the driver 36 engages the leg portion 42 of the active lancet 24. As the driver 36 engages the leg portion 42, the driver 36 applies a force to the leg portion 42 to move the lancet tip 46 in a direction orthogonal to the frame 30. As the lancet tip 46 moves, the lancet tip 46 pierces through the first sterility sheet 38 and continues into the skin of the user that has been placed over the incision location opening 64. In one embodiment, as the lancet tip 46 forms an incision, the body fluid sample from the incision travels along the capillary groove 48 via capillary action towards the contact portion 44 and the capillary groove 48 collects the body fluid sample from the incision while the lancet tip 46 is in the skin of the user. After the driver 36 reaches its maximum extension position, the driver 36 stops and reverses its path of movement. As the driver 36 reverses its path of movement, the force applied to the leg portion 42 is reduced and the lancet tip 46 withdraws from the incision. In another embodiment, the capillary groove 48 collects the body fluid sample while the lancet tip 46 returns to its original position in the chamber 32, as described next. As the driver 36 continues to reverse its direction of travel, the motion may be slowed down to allow enough time for the lancet tip 46 to fill the capillary groove 48 before the lancet tip 46 returns to its original position in the chamber 32. Due to the resilient nature of each lancet 24, the lancet tip 46 springs back to its original position in the chamber 32 on its own. In one embodiment, if the first incision formed by the lancet tip 46 is too shallow in depth to provide an adequate amount of body fluid sample for the test section 28 to yield accurate test results, then the lancet tip 46 can form a second incision in skin as described above before the actuation mechanism 60 rotates the frame 30. In its final resting position, the contact portion 44 of the active lancet 24 contacts the test section 28 and the body fluid sample is released from the capillary groove 48 onto the test section 28 by preferential capillarity between the contact portion 44 of the lancet 24 and the chemistry on the test section 28. The lancet 24 remains in its final resting position with the contact portion 44 resting against the test section 28. For the next test, the actuation mechanism 60 rotates the frame 30 via internal gears 52 or another index mechanism. The actuation mechanism 60 retracts the driver 36 and rotates the frame 30 so as to align the next corresponding opening 34 and the next unused or sterile lancet 24 with the driver 36.

A cartridge 120 according to one embodiment is illustrated in FIGS. 11, 12, 13, 14, 15, 16, 17, 18, and 19. The cartridge 120 is similar to cartridge 20; therefore for the sake of brevity features from the cartridge 120 that are similar to the cartridge 20 will not be discussed. Similar to cartridge 20, cartridge 120 includes a first sterility sheet 138 positioned to cover and seal one side of a plurality of chambers 132 of frame 130. However, cartridge 120 includes a second sterility sheet 140 positioned to cover and seal a plurality of openings 134 and the other side of the plurality of chambers 132. In another form, a test ring 126 and the second sterility sheet 140 are configured to cover and seal the same side of the plurality of chambers 132. In one embodiment, the second sterility sheet 140 is made of aluminum foil having a thickness of 25 micrometers and the second sterility sheet 140 is heat sealed over a frame 130 to seal each of chambers 132 separately.

Lancet wheel 122 is similar to lancet wheel 22. Similar to lancet wheel 22, lancet wheel 122 includes a lancet rim 123 with a plurality of lancets 124 extending radially inward from the lancet rim 123. Similar to lancet wheel 22, each of the lancets 124 includes a flexible leg portion 142, a contact portion 144, and a lancet tip 146. However, the contact portion 144 of each of the lancets 124 is curved and sized to rest on a cover barrier 156 when the lancet 124 is at rest. Further the contact portion 144 fits in a window 157 of the cover barrier 156 when the lancet is actuated, as described below. The spring force of flexible leg portion 142 applies a force to the cover barrier 156 to press the cover barrier 156 against a test section 128 until the lancet 124 is actuated by a driver 136. Each of lancets 124 also defines a slot 147 sized to receive a driver 136, as described in more detail below. Similar to lancet tip 46, lancet tip 146 defines a capillary groove 148.

Figure 13:
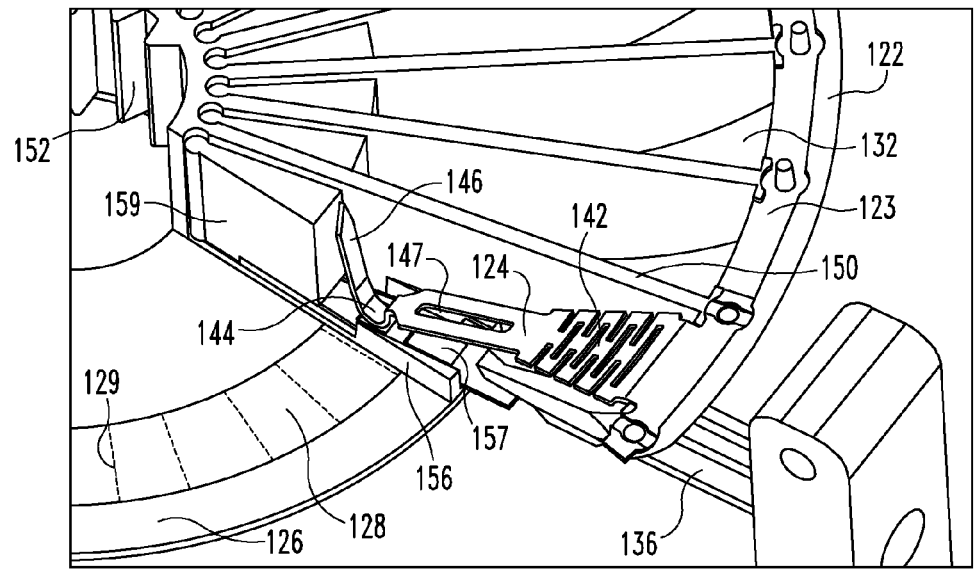
FIG. 13 is a top perspective view of a lancet wheel and a test ring that are incorporated into the FIG. 11 cartridge.
Figure 14:
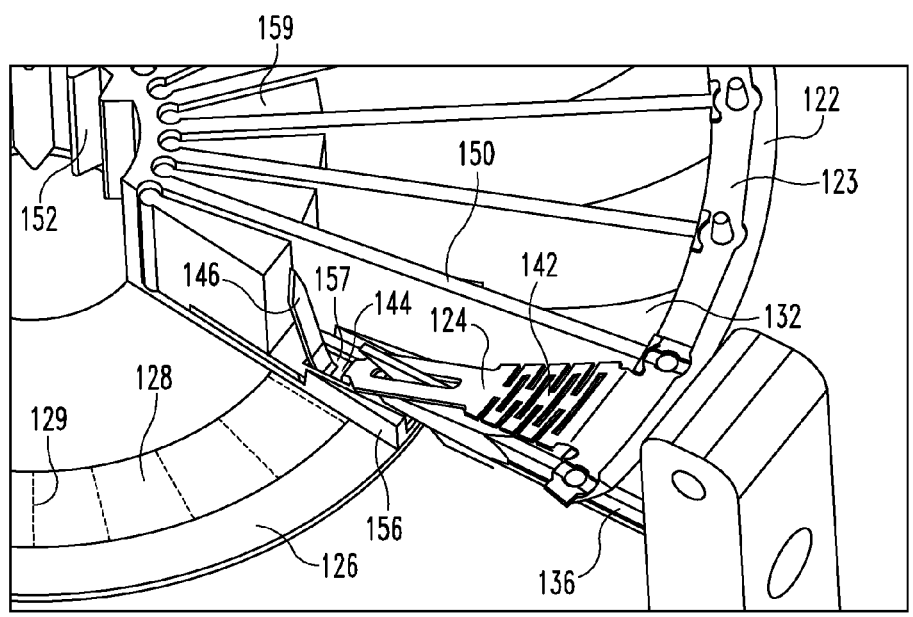
FIG. 14 is a top perspective view of a lancet wheel and a test ring that are incorporated into the FIG. 11 cartridge.
Figure 15:
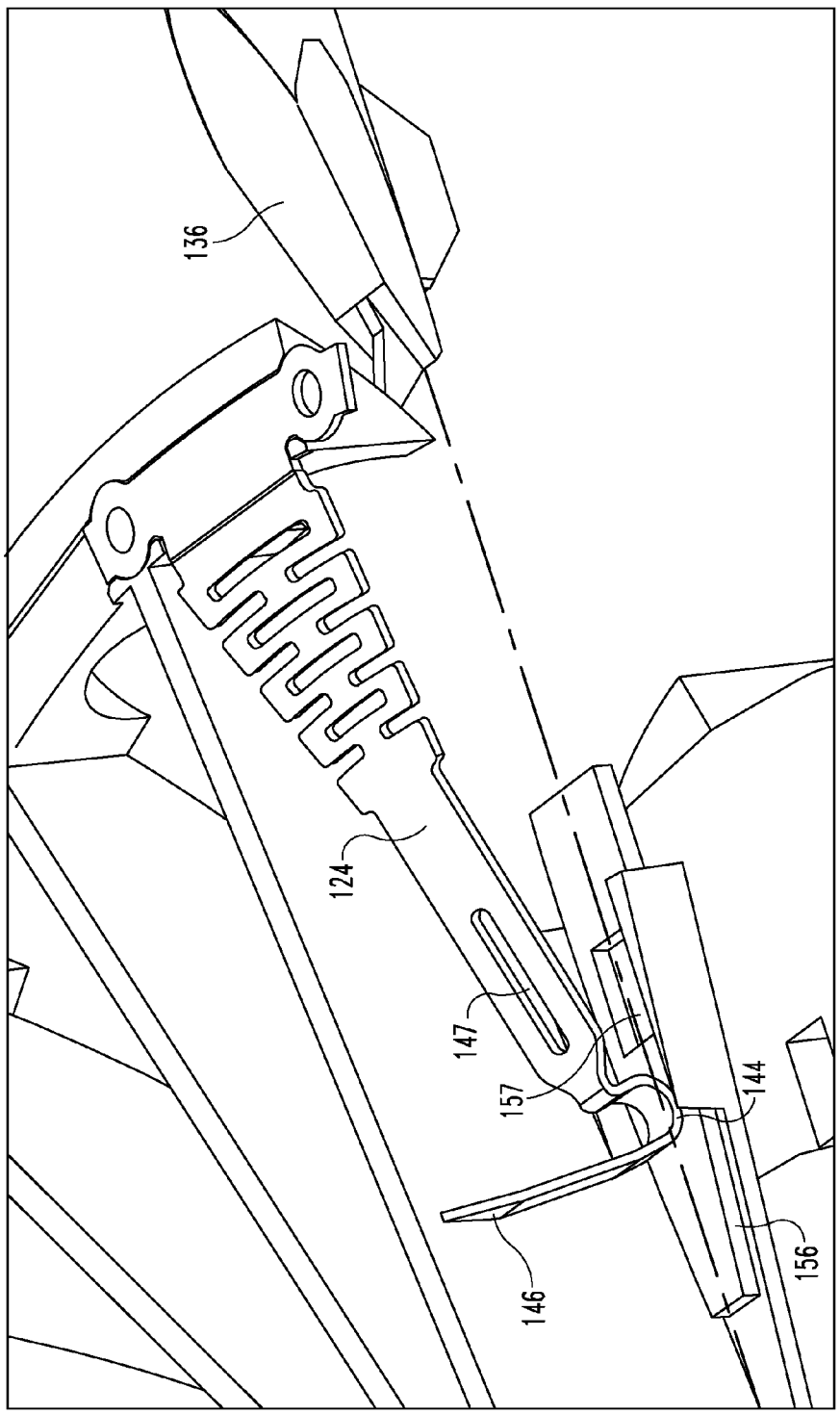
FIG. 15 is a top perspective view of a lancet wheel, a cover barrier, and a driver that are incorporated into the FIG. 11 cartridge.
Figure 16:
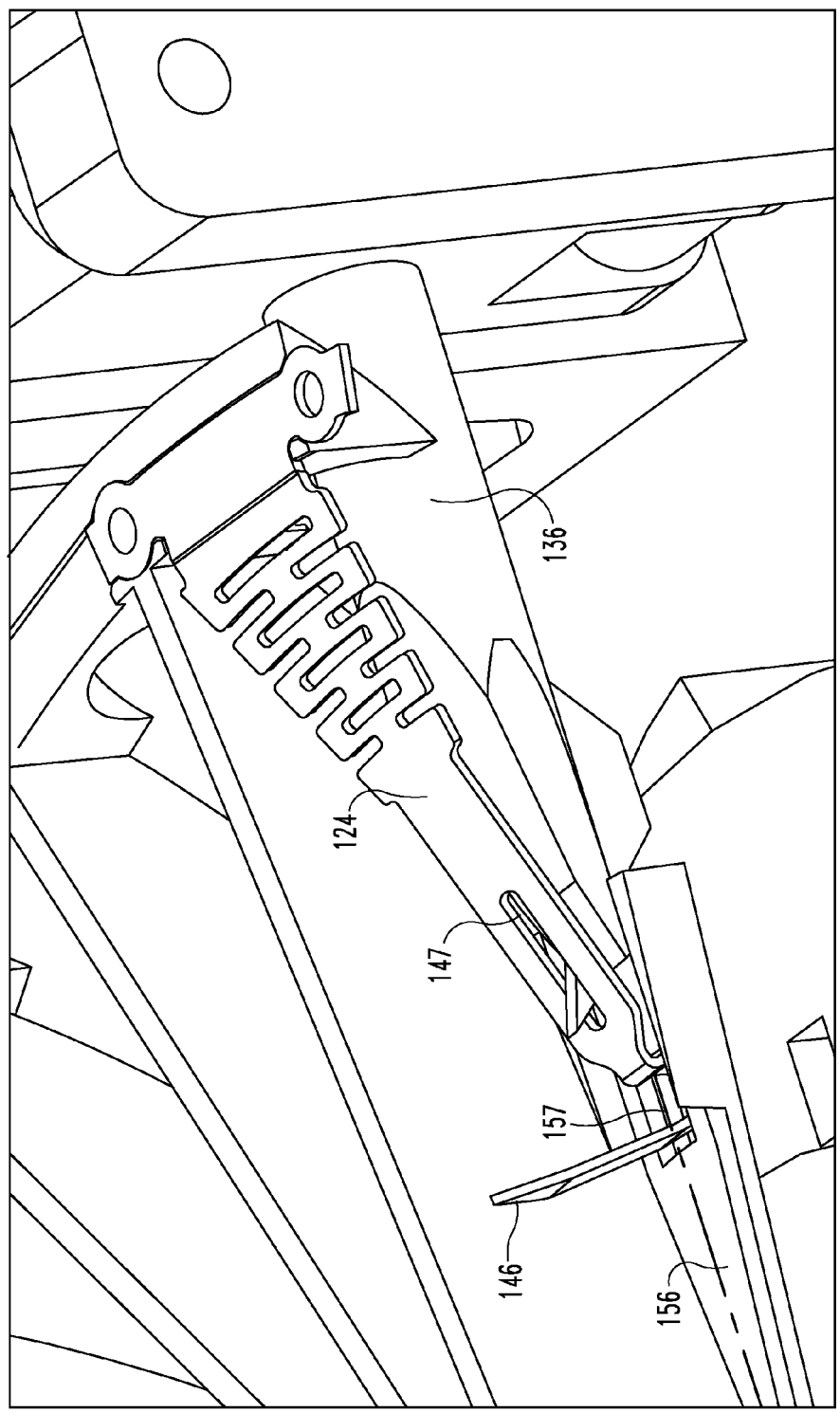
FIG. 16 is a top perspective view of a lancet wheel, a cover barrier, and a driver that are incorporated into the FIG. 11 cartridge.
Figure 17:
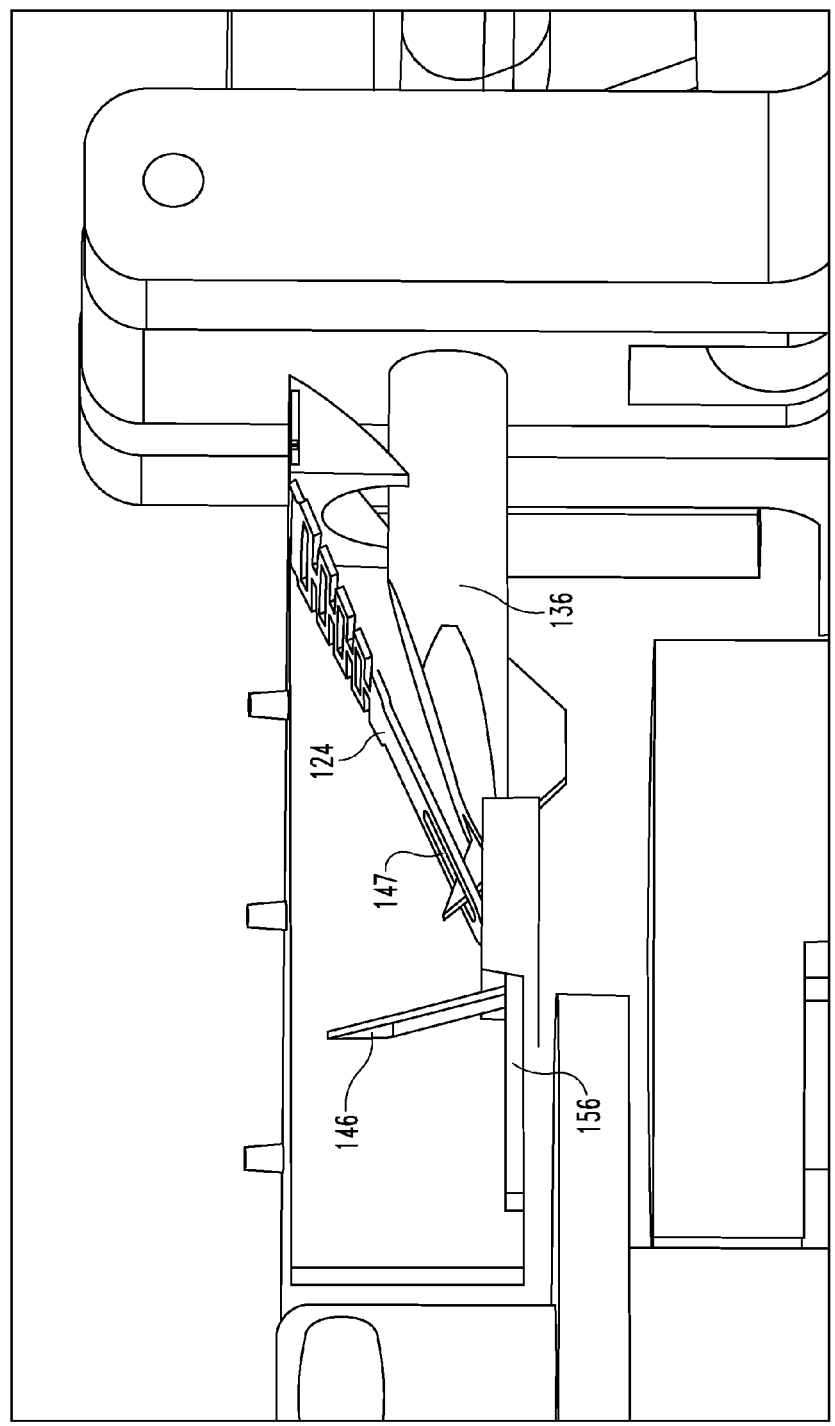
FIG. 17 is a side view of the FIG. 16 lancet wheel, cover barrier, and driver.
Figure 18:
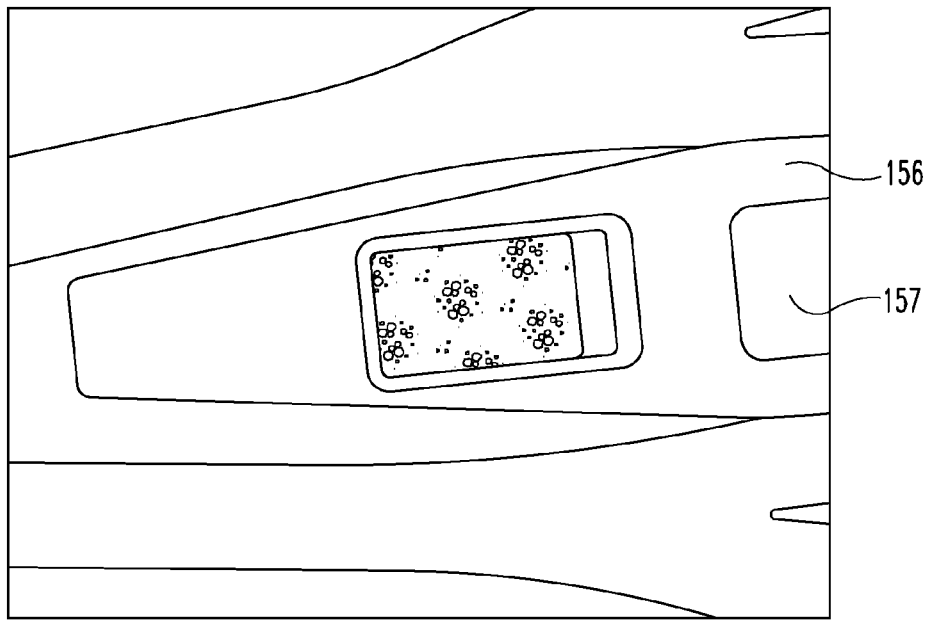
FIG. 18 is a top view of a cover barrier in a closed position.
Figure 19:
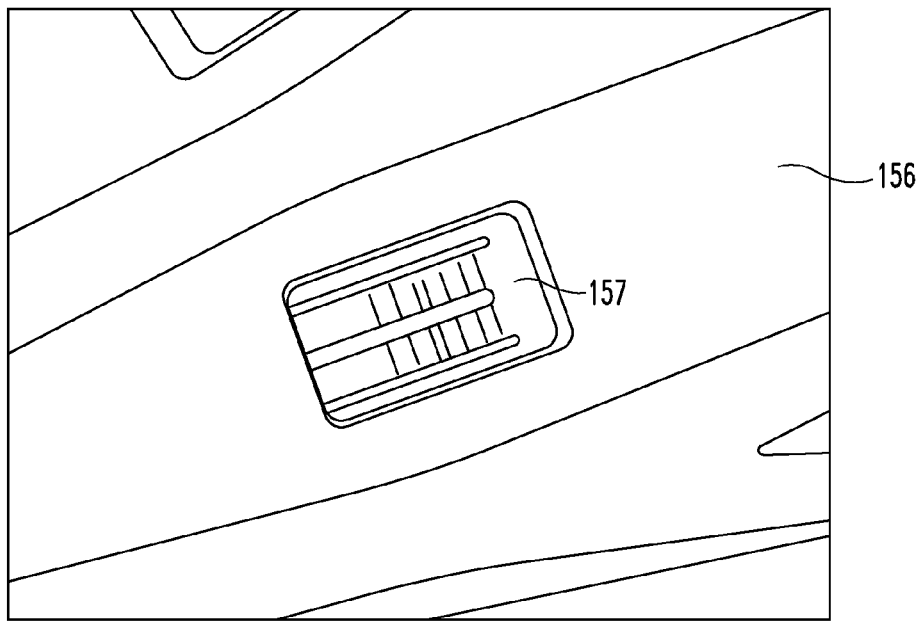
FIG. 19 is a top view of the FIG. 18 cover barrier in an open position.

Test ring 126 is similar to test ring 26; however, the plurality of test sections 128 is in the form of a continuous ring of chemistry mounted on or applied to a film. In one form, the chemistry coating is applied to a film made of polyethylene terephthalate having a thickness of 250 micrometers. The test ring 126 is attached to the second sterility sheet 140. As illustrated in FIGS. 13 and 14, a plurality of cover barriers 156 defining a plurality of windows 157 are positioned on the test ring 126 under the contact portion 144 of the plurality of lancets 124. The plurality of cover barriers 156 protect and cover the chemistry on the test ring 126 by eliminating contact between the test ring 126 and the lancet 124 prior to actuation of the lancet 124. Moreover, each cover barrier 156 is configured to cover one test section 128 as defined by the plurality of index lines 129. As the lancet 124 is actuated by the driver 136, the driver 136 slides through the slot 147 of the lancet 124 and engages the cover barrier 156 to push the cover barrier 156 across the test section 128 thereby positioning the window 157 over frame window 161 (described below) and the test section 128. The driver 136 also pushes the cover barrier 156 under a corresponding wedge 159 made of desiccant material, in the illustrated embodiment. Lancet 124 forms an incision in skin and collects a body fluid sample similarly to lancet 24, as described above. After the lancet 124 forms an incision and collects a body fluid sample, the contact portion 144 contacts the test section 128 through the window 157 and frame window 161 (described below) and deposits the body fluid sample onto the test section 128.

In the illustrated embodiment, the cartridge 120 includes a plurality of wedges 159 made of a desiccant material. Each of the wedges 159 is positioned in each chamber 132 of the frame 130 adjacent the lancet tip 146.

Frame 130 is similar to the frame 30. Frame 130 includes a plurality of walls 150 that define a plurality of chambers 132. Frame 130 includes an upper rim 153 that defines a plurality of openings 134. Each of the openings 134 is connected with a corresponding chamber 132. As should be appreciated, since each of the openings 134 are connected with one of the chambers 132, manufacturing of frame 130 is simplified. In the illustrated embodiment, each of the openings 134 has a semi-circular shape; however, in other embodiments the openings 134 are shaped differently. The frame 130 also includes a lower rim 155 defining a plurality of frame windows 161 for allowing contact between the contact portion 144 of the lancet 124 and the test section 128 in which a body fluid sample from the contact portion 144 is transferred to the test section 128 through the window 157 and the frame window 161. In the illustrated embodiment, the lower rim 155 is substantially flat. In other embodiments, the lower rim 155 is curved.

In this embodiment, the frame 130 is made of polypropylene and constructed by injection molding techniques. In other embodiments, the frame 130 is made of other material and other techniques as described above.

The frame 130 also includes a plurality of internal gears 152 similar to internal gears 52. The frame 130 also includes a hub 154 on the interior or center of the frame 130. Hub 154 is similar to hub 54.

Figure 20:
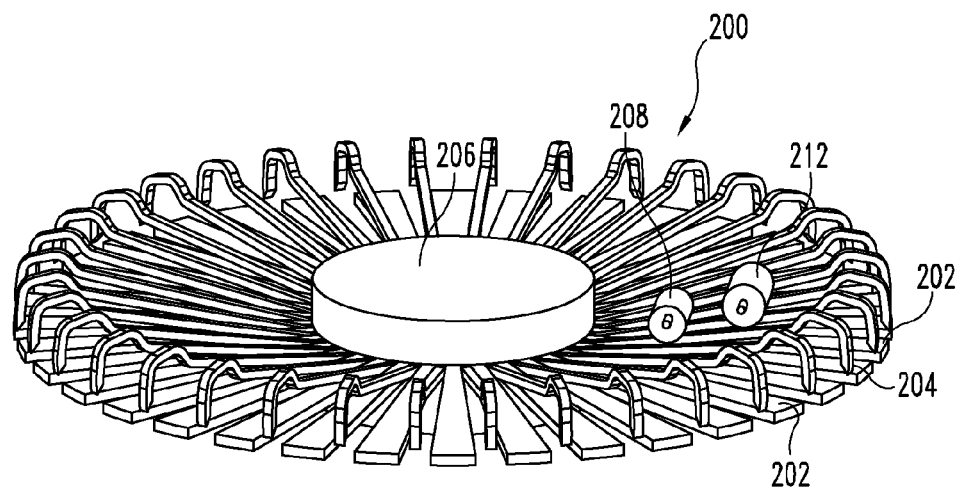
FIG. 20 is a top perspective view of a microsampler wheel according to another embodiment.
Figure 21:
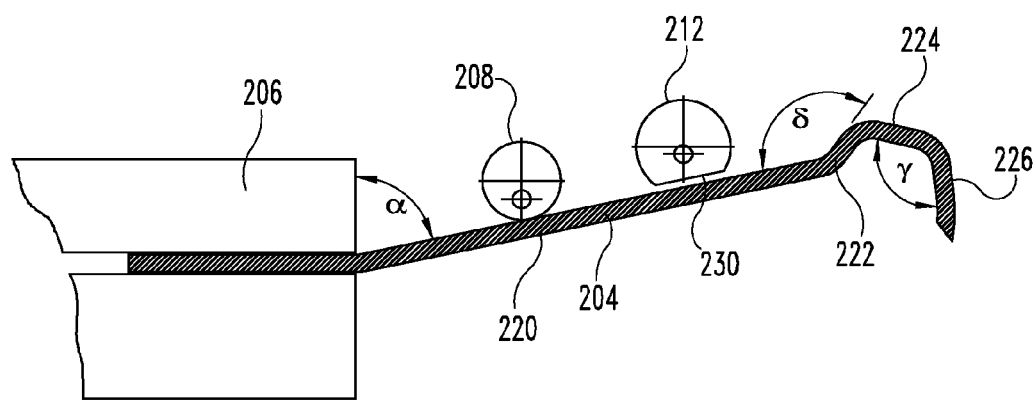
FIG. 21 is a cross-sectional view of the FIG. 20 microsampler wheel.

As mentioned previously, a second embodiment of an integrated disposable cartridge or disc includes a microsampler wheel 200 and a test ring or plurality of test sections 210. As should be appreciated, the lancets on the microsampler wheel 200 and the plurality of test sections 210 are oriented in an alternative manner, as described below. One embodiment of a microsampler wheel 200 is illustrated in FIGS. 20 and 21. The microsampler wheel 200 lances skin to form an incision and collects the body fluid sample from the incision. The body fluid sample is transferred from the microsampler wheel 200 to one of the plurality of test sections 210 where the body fluid sample is analyzed.

The microsampler wheel 200 includes a plurality of ribs 202 alternating with a plurality of microneedles or lancets 204. The microsampler wheel 200 also includes a base 206 from which the plurality of ribs 202 and the plurality of lancets 204 extend from and a first cylinder 208 configured to drive each of the plurality of lancets 204 to form an incision in skin.

Each of the ribs 202 serves as a guide or a reference plane for an adjacent lancet 204 to determine the depth of penetration of a lancet tip 226, as described below. Each of the plurality of ribs 202 is a trapezoidal shape; however, in other embodiments, each of the ribs 202 may be shaped differently, such as polygonal or oval, to name a few. Furthermore, each of the plurality of ribs 202 is substantially flat, which beneficially enables the microsampler wheel 200 to form an overall compact shape. Moreover, each of the ribs 202 serves as a reference plane or surface from which the depth of penetration of the corresponding lancet tip 226 can be determined.

Each of the lancets 204 includes a leg portion 220 that extends from the base 206 towards a first leg member 222. The first leg member 222 spans between the leg portion 220 and a second leg member 224 of each of the lancets 204. The second leg member 224 spans between the first leg member 222 and a lancet tip 226 of each of the lancets 204. As shown in FIG. 21, the leg portion 220 extends from the base 206 and forms a first angle α with the base 206. First angle α is an acute angle. The leg portion 220 is substantially straight. The first leg member 222 forms a second angle δ with the leg portion 220. The second angle δ is an obtuse angle, as illustrated. The first leg member 222 is substantially straight. The second leg member 224 forms a third angle γ with the lancet tip 226. The third angle γ is an obtuse angle. The second leg member 224 is substantially straight. In another embodiment, the first leg member 222 and/or the second leg member 224 are curved.

As shown in FIG. 21, the lancet tip 226 is curved. The curvature of lancet tip 226 corresponds to the radius of the circular path that the lancet 204 follows during actuation and retraction of the lancet 204. Moreover, the curvature of the lancet tip 226 corresponds with the curvature of the movement of the lancet 204 as the lancet tip 226 forms an incision in a user's skin and thereafter withdraws from the user's skin. In another embodiment, the lancet tip 226 is straight.

Figure 22:
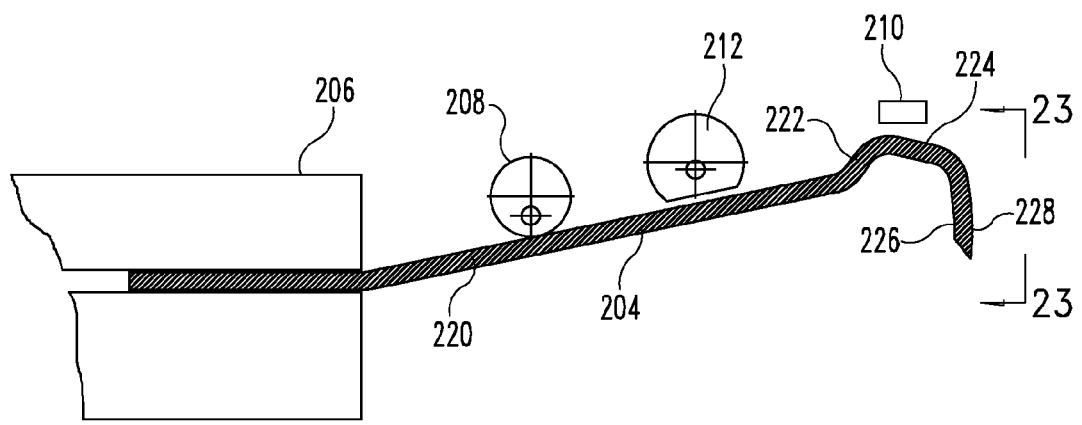
FIG. 22 is a cross-sectional view of the FIG. 20 microsampler wheel including a testing element.
Figure 23:
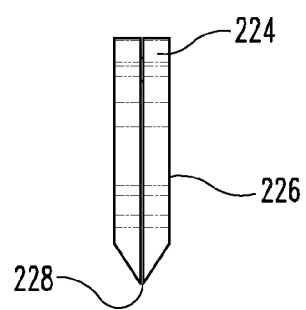
FIG. 23 is a front partial view of the FIG. 22 lancet and capillary.

Each of the lancets 204 also includes a capillary groove 228 sized to draw body fluid from an incision or skin surface via capillary action. In one embodiment, the capillary groove 228 includes a hydrophilic coating to draw the body fluid along the capillary groove 228 towards the second leg member 224. The capillary groove 228 extends from the lancet tip 226 to the second leg member 224 as shown in FIGS. 22 and 23. In some embodiments, the capillary groove 228 extends from the lancet tip 226 to the second leg member 224 and into the first leg member 222. As illustrated in FIGS. 22 and 23, the capillary groove 228 is positioned on the front side of the lancet tip 226. In other embodiments, the capillary groove 228 may be positioned on the front side or the rear side of the lancet tip 226 corresponding to the placement of the test section 210. The front side of the lancet tip 226 corresponds to the face of the lancet 204 that is furthest away from the base 206. The back side of the lancet tip 226 corresponds to the face of the lancet tip 226 that is closest to the base 206.

As shown in FIG. 23, the capillary groove 228 forms an open sampling channel to collect a body fluid sample via capillary action. In another embodiment, the capillary groove 228 is enclosed. As should be appreciated, when compared to a closed capillary or channel, an open capillary groove 228 has the advantage that the lancet 204 can be produced more easily in an etching process. Other examples of forming the capillary groove 228 in the lancet 204 include a sharp point, a laser beam, or other forms or mechanisms of removing material from the lancet 204 to create the open capillary groove 228. Any technique of forming the capillary groove 228 results in automatic body fluid sampling when the lancet tip 226 is positioned in skin. Additionally, an open capillary as compared to a closed capillary more easily collects the body fluid sample that may be on the skin surface surrounding the incision.

As illustrated in FIG. 20, the base 206 is circular in shape. The base 206 may be shaped differently in other embodiments, such as, rectangular, oval, or square. As described below, the ribs 202, the lancets 204, and the base 206 may be formed from one piece of material. In other forms, the ribs 202 and/or the lancets 204 may be manufactured separately and then attached to the base 206. In one embodiment, the wheel 200 is loaded into a meter configured to display the analysis results. Further, in this embodiment, the wheel 200 is stationary and the base 206 is attached to a housing of the meter such that the housing or exterior of the meter rotates about the wheel 200 to expose an unused lancet 204. However, in another embodiment, the base 206 rotates about its center to expose an unused lancet 204 in the housing.

As illustrated in FIGS. 20 and 21, the first cylinder 208 is located adjacent the leg portion 220 of the lancet 204. The first cylinder 208 is substantially circular in shape and rolls or rotates along the leg portion 220 of the lancet 204 towards the lancet tip 226 in one embodiment, or in another embodiment the first cylinder 208 slides along the surface of the leg portion 220 towards the lancet tip 226. As should be appreciated, the first cylinder 208 applies a force to the leg portion 220 to move the lancet 204 in a direction away from the first cylinder 208. The movement of the lancet 204 from the force of the first cylinder 208 causes the lancet tip 226 to follow a circular path to form an incision in a user as described previously. At the end of the movement or range of motion of the first cylinder 208, the first cylinder 208 reverses its direction and moves toward the base 206. In other embodiments, actuation of the lancet 204 occurs by other forms, such as a driver, a spring, or another mechanical or electrical mechanism. These other forms of actuation of the lancets 204 will also force the curved lancet tip 226 to follow a circular movement. The lancing profile of the lancet tip 226 can be traced by correlating the distance the first cylinder 208 travels along the leg portion 220, the diameter of first cylinder 208, and the geometry of the lancet 204.

After the incision has been formed by the lancet tip 226, the lancet tip 226 is removed from the skin of the user by springing back to its original pre-incision forming position and contacting one of the test sections 210 to transfer the body fluid sample to the test section 210. As the first cylinder 208 reverses its direction and moves toward the base 206, the curvature of the lancet tip 226 ensures that as the lancet tip 226 withdraws from the incision, the lancet tip 226 will follow the same circular path that it formed during the incision. No additional actuator is necessary to withdraw the lancet tip 226 from the incision; rather the resilient nature of the lancet 204 causes the lancet tip 226 to spring back to its original position referenced by the ribs 202 as the first cylinder 208 returns to its original position. Moreover, as the lancet 204 springs back to its original pre-incision forming position, the body fluid sample contained in the capillary groove 228 is transferred to the test section 210 as the second leg member 224 or the lancet tip 226 contacts the test section 210, as described below. The lancet 204 in its original position will ensure that a subsequent user is not accidentally stuck by the contaminated lancet tip 226.

In the embodiment illustrated in FIG. 21, a second cylinder 212 is positioned adjacent or near the first cylinder 208 to act as a stop mechanism for the first cylinder 208 during actuation of the first cylinder 208. In the illustrated embodiment, the second cylinder 212 is substantially circular in shape with a flat surface 230 positioned to contact the leg portion 220. In other embodiments, the second cylinder 212 may be another shape. For example, the second cylinder can be a rectangular, triangular, or oval, to name a few shapes. The second cylinder 212 forms a stop for the first cylinder 208 to limit the movement of the first cylinder 208 and the lancet 204. In another embodiment, the second cylinder 212 contacts the leg portion 220 during actuation of the lancet 204 and retraction of the lancet tip 226 from the incision. For example, during actuation, the second cylinder 212 applies a force to the leg portion 220 as the first cylinder 208 also applies a force to the leg portion 220. In this embodiment, the engagement between the second cylinder 212 and the leg portion 220 ensures that the lancet tip 226 is drawn slowly out of the incision formed in the user's skin. Second cylinder 212 controls the velocity of the lancet tip 226 during removal of the lancet tip 226 from the incision and movement of the lancet tip 226 to its original position. The combination of the first cylinder 208 and the second cylinder 212 ensures that particular prescribed lancing and velocity profiles will be followed by the lancet tip 226. The combination of the first cylinder 208 and the second cylinder 212, in one embodiment, ensures that the lancet tip 226 forms the incision rapidly and the lancet tip 226 is withdrawn slowly from the incision. In another embodiment, the first cylinder 208 controls the velocity of the lancet tip 226 without the second cylinder 212.

In one embodiment, the microsampler wheel 200 is formed from a single piece of material by stamping a metal plate to form the plurality of ribs 202 and the plurality of microneedles or lancets 204 and removing any excess material. In another embodiment, the microsampler wheel 200 is formed from etching and bending a metal plate to form the plurality of ribs 202 and the plurality of microneedles or lancets 204. In other embodiments, the microsampler wheel 200 may be formed by attaching the plurality of ribs 202 and the plurality of lancets 204 to the base 206. The microsampler wheel 200 may be made of metal, such as stainless steel, titanium, or nickel; plastic; and/or other materials.

The plurality of test sections 210 is similar to the test sections 28 described above; therefore for the sake of brevity the details are not repeated. The plurality of test sections 210 are positioned near the plurality of lancets 204 such that one test section 210 is positioned near each capillary groove 228. The plurality of test sections 210 may be positioned near the second leg member 224 as shown in FIG. 22, the front of the lancet tip 226 as shown in FIG. 24, or the rear of the lancet tip 226 as shown in FIG. 26.

Reference will now be made to the various configurations of the lancet 204 and the test section 210. As shown in FIG. 22, the test section 210 is positioned near the second leg member 224 to analyze the body fluid sample. In this embodiment, the capillary groove 228 is positioned on the front side of the lancet 204 as illustrated in FIG. 23. To form an incision, the first cylinder 208 rotates along the leg portion 220 and applies a force to the leg portion 220 to rotate the lancet 204 about the edge of the base 206. In the embodiment illustrated in FIG. 22, the second cylinder 212 applies a force to the leg portion 220 to assist the first cylinder 208 to rotate the leg portion 220 about the edge of the base 206. As should be appreciated, the second cylinder 212 is optional. While the leg portion 220 rotates about the edge of the base 206, the lancet tip 226 follows a circular path to form an incision in a user. The capillary groove 228 collects a body fluid sample as the lancet tip 226 forms the incision. The body fluid sample in the capillary groove 228 first flows in the lancet tip 226 in a direction substantially parallel to the incision in skin. In this embodiment, the body fluid sample continues to flow into capillary groove 228 in the second leg member 224. As the body fluid sample flows into the second leg member 224, the direction of flow changes by the third angle γ. In one form, the third angle γ is approximately 90 degrees; therefore the flow of the body fluid sample changes direction by about 90 degrees from the lancet tip 226 to the second leg member 224. The first cylinder 208 and the second cylinder 212 reverse their directions such that the force is removed from the leg portion 220 and the lancet tip 226 withdraws from the skin. As the first cylinder 208 and the second cylinder 212 reverse their directions, the lancet 204 springs or moves past the original pre-incision forming position of the lancet 204 such that the second leg member 224 touches the test section 210. While the second leg member 224 contacts the test section 210, the body fluid sample is transferred from the capillary groove 228 to the test section 210. In this embodiment, the capillary groove 228 extends into the second leg member 224 a corresponding distance such that as the second leg member 224 contacts the test section 210, the body fluid sample in the capillary groove 228 is transferred to the test section 210. The test section 210 analyzes the body fluid sample.

Figure 24:
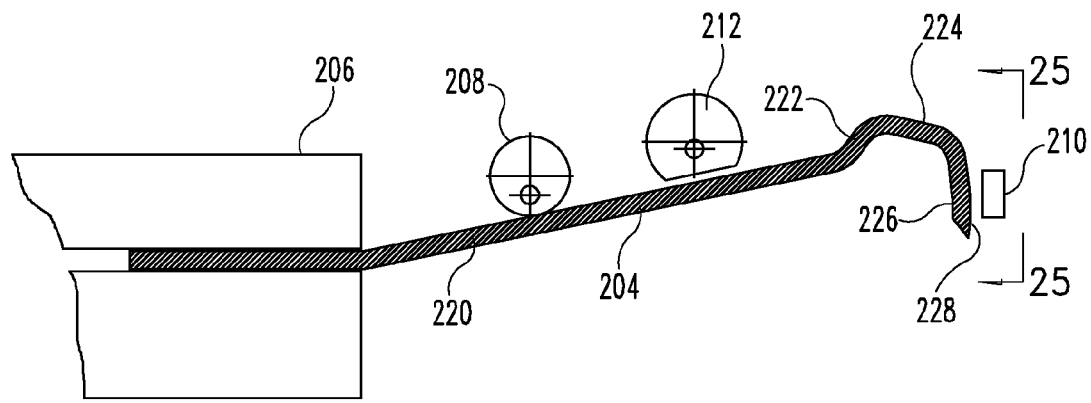
FIG. 24 is a cross-sectional view of the microsampler wheel including a testing element positioned near a lancet tip according to another embodiment.
Figure 25:
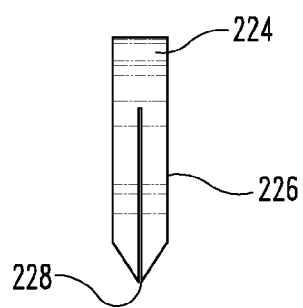
FIG. 25 is a front partial view of the FIG. 24 lancet and capillary.

As illustrated in FIGS. 24 and 25, the capillary groove 228 is positioned on the front side of the lancet tip 226 and likewise the test section 210 is positioned near the front side of the lancet tip 226. The first cylinder 208, second cylinder 212, and the lancet 204 are similar to the embodiment described with reference to FIGS. 22 and 23, unless described differently herein. The lancet tip 226 is actuated to form an incision in skin, and the capillary groove 228 collects a body fluid sample from the incision. In this embodiment, the body fluid sample flows in the capillary groove 228 in a direction substantially parallel to the incision in skin. After the lancet tip 226 is withdrawn from the incision in skin, the lancet 204 moves to its original pre-incision forming position and the lancet tip 226 contacts the test section 210. As the lancet tip 226 contacts the test section 210, the body fluid sample from the capillary groove 228 is deposited onto the test section 210.

Figure 26:
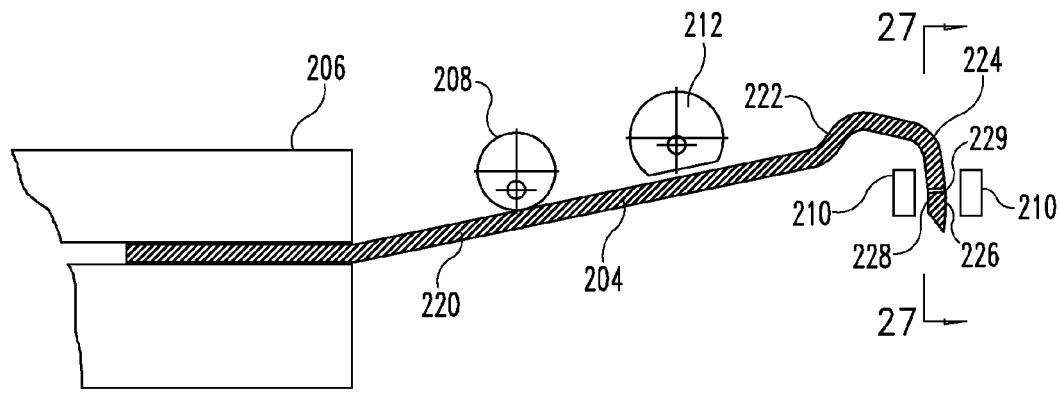
FIG. 26 is a cross-sectional view of the microsampler wheel including a testing element positioned near a lancet tip according to another embodiment.
Figure 27:
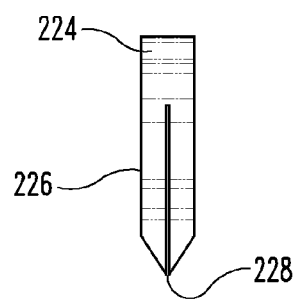
FIG. 27 is a front partial view of the FIG. 26 lancet and capillary.

In another embodiment, illustrated in FIGS. 26 and 27, the capillary groove 228 is located on the rear side or back side of the lancet tip 226. As illustrated, the lancet tip 226 can include a second capillary groove 229 that extends from the capillary groove 228 on the rear side of the lancet tip 226 through the lancet tip 226 to the front side of the lancet tip 226. With the additional capillary groove 229, the test section 210 can be either positioned adjacent the rear side or adjacent the front side of the lancet tip 226. The first cylinder 208, second cylinder 212, and the lancet 204 are similar to the embodiment described with reference to FIGS. 22 and 23, unless described differently herein. The lancet tip 226 forms an incision in skin and the capillary groove 228 collects a body fluid sample from the incision. In this embodiment, the body fluid sample flows in the capillary groove 228 in a direction substantially parallel to the incision in skin. In one embodiment, as the lancet tip 226 returns to its original pre-incision forming position, the rear side of the lancet tip 226 contacts the test section 210 positioned adjacent the rear side of the lancet tip 226 and the body fluid sample in the capillary groove 228 is deposited onto the test section 210. As should be appreciated, the presence of capillary groove 229 ensures the body fluid sample will be deposited onto the test section 210 whether the capillary groove 228 is located on the front or rear side of the lancet tip 226 and the test section 210 is positioned adjacent either the rear side or front side of the lancet tip 226.

A third embodiment also concerns an integrated disposable cartridge or disc similar to the second embodiment above. The cartridge in the third embodiment also utilizes a unique lancet wheel design that includes a plurality of microneedles or lancets that alternate with a plurality of ribs. The lancets in this embodiment are similar to the lancets in the previously described embodiments. The lancets and the plurality of ribs are attached to a base in an alternating manner and configured in an initial pre-incision forming position. The lancets and the plurality of ribs are configured to rotate about the base. A first drive mechanism forces the lancet tip to rotate about the base during penetration and retraction as the first drive mechanism presses against the lancet and the one or more ribs adjacent the lancet. A second drive mechanism forces one or more of the ribs next to the lancet to contact skin near the incision location as the ribs rotate about the base and thereby form a reference plane from which the penetration depth of a lancet is measured relative to the adjacent one or more ribs. The position of the one or more ribs relative to the lancet allows the user to adjust the penetration depth of the lancet independent of the actuation and movement of the lancet. For example, the actuation and movement of the lancet is determined by pressing the first drive mechanism against the one or more ribs and the lancet while the penetration depth is determined by pressing the second drive mechanism against the one or more ribs. The penetration depth of the lancet is easily adjusted as the orientation of the one or more ribs changes as determined by the second drive mechanism. Moreover, the unique and elegant shape of the second drive mechanism enables the one or more ribs to express additional bodily fluid to the skin as the second drive mechanism presses against and releases the one or more ribs to create a pumping action of the ribs against skin.

A microsampler wheel 300 according to another embodiment is illustrated in FIGS. 28, 29, 30, 31, and 32. The microsampler wheel 300 is similar to microsampler wheel 200; therefore for the sake of brevity features from the microsampler wheel 200 that are similar to the microsampler wheel 300 will not be discussed. Similar to microsampler wheel 200, microsampler wheel 300 includes a plurality of ribs 302 alternating with a plurality of lancets 304. Also similar to the microsampler wheel 200, the microsampler wheel 300 includes a base 306 from which the plurality of ribs 302 and the plurality of lancets 304 extend from. Each of the plurality of ribs 302 includes a first end 330 attached to the base 306 and a second end 332 configured to contact skin S of a user. In this embodiment, prior to actuation of a particular lancet 304, the pair of ribs 302 adjacent to that lancet are substantially parallel to a leg portion 320 of the lancet 304. The microsampler wheel 300 also includes a first cylinder 308 and a second cylinder 312. First cylinder 308 is configured similar to first cylinder 208. Second cylinder 312 includes a pair of cylinders or rollers positioned such that each roller contacts an individual rib 302. The rollers of second cylinder 312 straddle one lancet 304 between them such that the individual rollers of second cylinder 312 are positioned to avoid contact with the lancet 304. In this embodiment, each of the individual rollers of second cylinder 312 includes a curved portion 314 and a substantially flat portion 316. In other embodiments, the second cylinder 312 may be another shape. Although not shown, in some embodiments, microsampler wheel 300 also includes a plurality of test sections as previously described.

Figure 28:
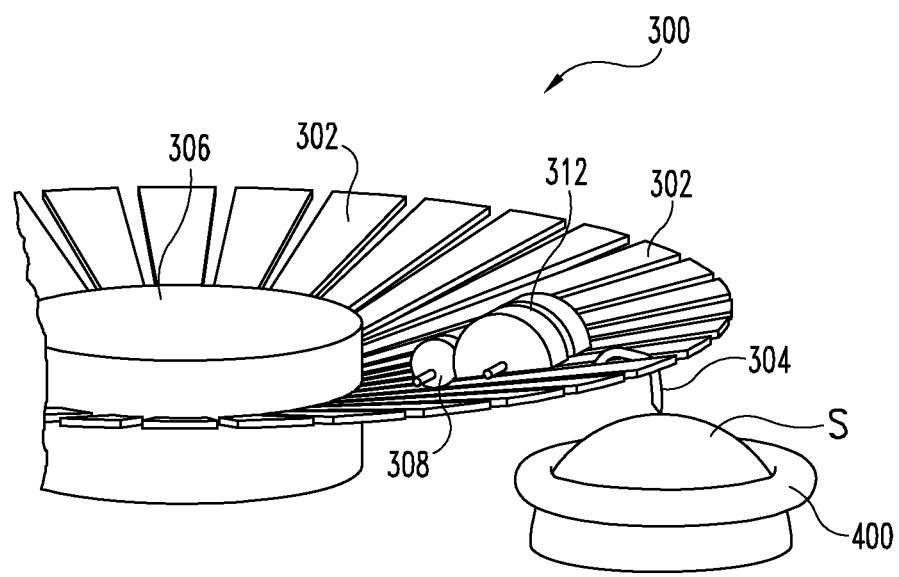
FIG. 28 is a top perspective view of a microsampler wheel according to another embodiment.

As illustrated in FIG. 28, a lancet tip 326 of one of the lancets 304 is positioned adjacent to or in contact with skin S of a user. In the illustrated embodiment, an expression ring 400 is positioned on a finger tip; however, in other embodiments expression ring 400 is not required for microsampler wheel 300 to form an incision, express a bodily fluid sample, and collect a bodily fluid sample. Moreover, the microsampler wheel 300 is configured for use on other body parts of a user in addition to a finger, in other words the microsampler wheel 300 is configured for alternate site testing. In this initial start position, substantially flat portion 316 of second cylinder 312 contacts the pair of ribs 302. In this embodiment, the pair of ribs 302 are substantially parallel to the leg portion 320 of the lancet 304 positioned between them. In other embodiments, the pair of ribs 302 can be positioned either above or below the lancet 304.

Figure 29:
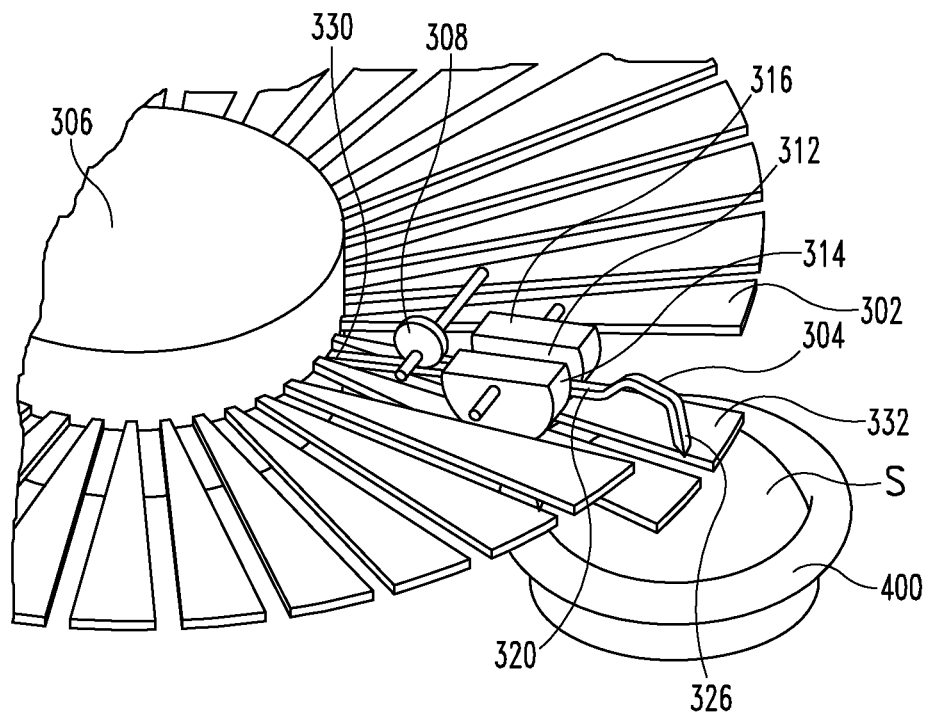
FIG. 29 is a top perspective view of the FIG. 28 microsampler wheel.

As illustrated in FIG. 29, second cylinder 312 is rotated such that the curved portion 314 of second cylinder 312 contacts and presses the second end 332 of each of the pair of ribs 302 against skin S of the user. The orientation of the curved portion 314 with the ribs 302 facilitates rotation of second cylinder 312 to thereby adjust the orientation of the ribs 302 during lancing, expressing, and sampling. The initial contact between the pair of ribs 302 and the skin S of the user is a skin reference position from which penetration depth of the lancet tip 326 can be measured. In some embodiments, the second cylinder 312 is rotated to further press the pair of ribs 302 against skin S of the user to express bodily fluid to the incision site. In other embodiments, the second cylinder 312 is rotated back and forth to cause a pumping action of the pair of ribs 302 against skin S of the user to further facilitate expression of the body fluid to the incision site.

Figure 30:
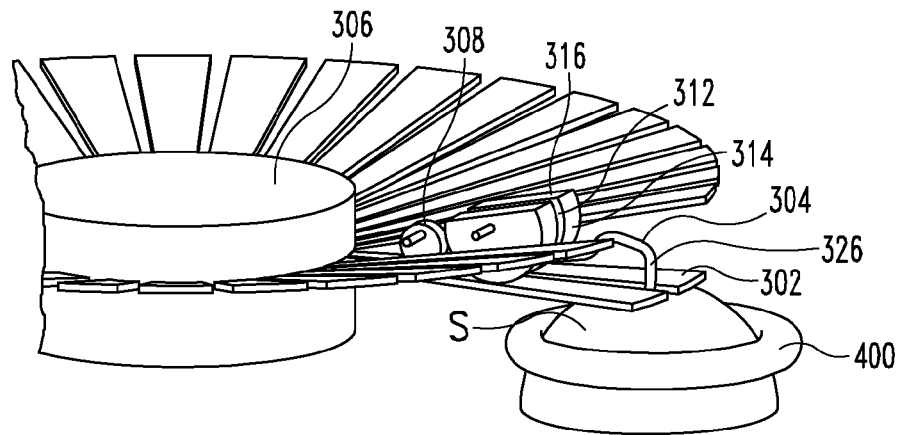
FIG. 30 is a top perspective view of the FIG. 28 microsampler wheel.

As shown in FIG. 30, the lancet 304 is actuated to form an incision in skin. The first cylinder 308 is pressed against the pair of ribs 302 and the leg portion 320 of the lancet 304 to rotate the lancet 304 about the base 306 and force the lancet tip 326 into skin S of the user. The penetration depth of the lancet tip 326 is determined by the geometry of the lancet 304, the orientation of the pair of ribs 302 against the skin S of a user, and the distance the first cylinder 308 travels along the pair of ribs 302 and/or until the first cylinder 308 contacts the second cylinder 312. In this form, as the first cylinder 308 rolls along the pair of ribs 302 and the leg portion 320, the lancet tip 326 rotates about the base 306 to form an incision in skin S. As the first cylinder 308 contacts the second cylinder 312, penetration of the lancet tip 326 in skin S is stopped. In another embodiment, the first cylinder 308 rolls along only the leg portion 320 of the lancet 304 to rotate the lancet 304 about the base 306 and force the lancet tip 326 into skin S of the user. In yet another embodiment, the first cylinder 308 is configured to press against or roll along the pair of ribs 302 adjacent the leg portion 320. In any embodiment, the lancet tip 326 follows a circular path to form an incision in skin S of the user as the lancet 304 is rotated about the base 306.

Figure 31:
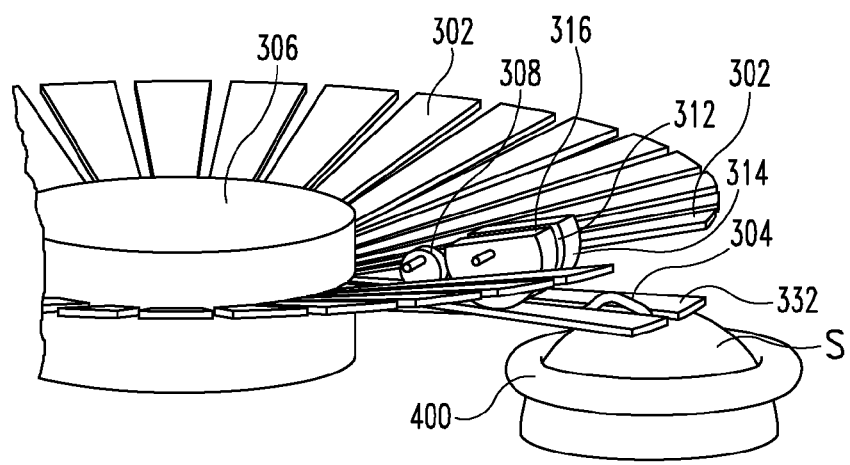
FIG. 31 is a top perspective view of the FIG. 28 microsampler wheel.

As shown in FIG. 31, the lancet 304 collects the bodily fluid sample similarly as lancet 204 described above. However, the second end 332 of each of the pair of ribs 302 is pressed against the skin S. As mentioned previously, in another embodiment, the second cylinder 312 is rotated back and forth to cause a pumping action of the pair of ribs 302 against skin S of the user. This pumping action facilitates expression of the body fluid to the incision site and sampling of the body fluid in the lancet 304.

Figure 32:
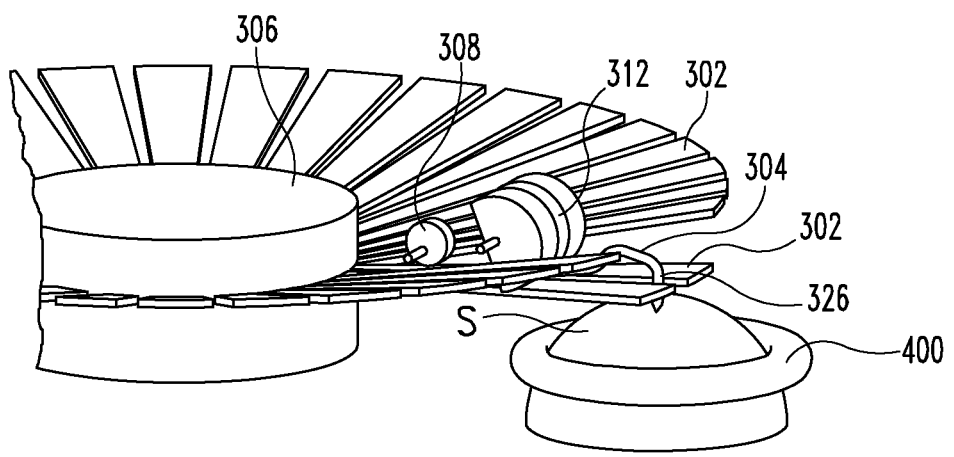
FIG. 32 is a top perspective view of the FIG. 28 microsampler wheel.

The first cylinder 308 starts to move or roll back from the second cylinder 312 to its initial start position as shown in FIG. 32. As the first cylinder 308 returns to its original position, the lancet 304 rotates about the base 306 and springs back to its pre-incision forming position. Since second cylinder 312 is configured from two rollers or members separated a distance, the lancet 304 springs back and travels through the gap formed between the two rollers or members. As mentioned previously and described above, the lancet 304 contacts a test section to transfer the body fluid sample to the test section similarly to lancet 204. The second cylinder 312 is rotated such that the curved portion 314 disengages from the pair of ribs 302, and the pair of ribs 302 rotates about the base 306 towards their initial pre-incision forming position. Although not illustrated, the second cylinder 312 will continue to rotate to its original pre-incision forming position until the substantially flat portion 316 contacts the pair of ribs 302.

A cartridge 420 according to one embodiment is illustrated in FIGS. 33, 34, 35, 36, 37, 38, 39, and 40. As should be recognized from these figures, cartridge 420 shares a number of features in common with cartridge 20 illustrated in FIGS. 1, 2, 3, 4, 5, 6, and 7. Therefore for the sake of brevity, common features from the cartridge 420 and the cartridge 20 will not be discussed. Cartridge 420 has a test ring frame 480; however, cartridge 20 does not have a test ring frame. Like cartridge 20, cartridge 420 has a test ring 426; however, test ring 426 is mounted to test ring frame 480 as described in more detail below. Also like cartridge 20, cartridge 420 includes a lancet wheel 422 positioned in a lancet frame 430. However, lancet wheel 422 and lancet frame 430 are slightly different than lancet wheel 22 and frame 30, respectively. In one embodiment, cartridge 20 includes twenty-five lancets 24, twenty-five test sections 28, and twenty-five chambers 32. Comparatively, in one embodiment, cartridge 420 includes fifty lancets 424, fifty test sections 428, and fifty chambers 432 in which cartridge 420 has an approximately 20% larger diameter than cartridge 20.

The manner in which cartridge 420 transfers a body fluid sample from a lancet 424 to a test section 428 is different than cartridge 20. As explained below, cartridge 420 includes a lancet 424 having a lancet tip 446 that forms an incision in tissue, collects a body fluid sample from the incision in capillary groove 448, and transfers the body fluid sample to a test section 428 as the lancet tip 446 contacts the test section 428. In other words, the lancet tip 446 transfers the body fluid sample to the test section 428. As should be appreciated, the body fluid sample is not required to fill the entire capillary groove 448 of the lancet 424 to have a sufficiently sized sample from which to test. Moreover, since the body fluid sample is not required to fill the entire capillary groove 448 a higher testing success rate is achieved and a smaller sized body fluid sample is needed to test with. As described previously, cartridge 20 includes a lancet 24 having a lancet tip 46 that forms an incision, the body fluid sample is collected in capillary groove 48, and as the lancet returns to its original position the contact portion 44 contacts the test section 28 to transfer the body fluid sample to the test section 28. In this configuration, the contact portion 44 or tail of the lancet 24 transfers the body fluid sample to the test section 28.

Figure 33:
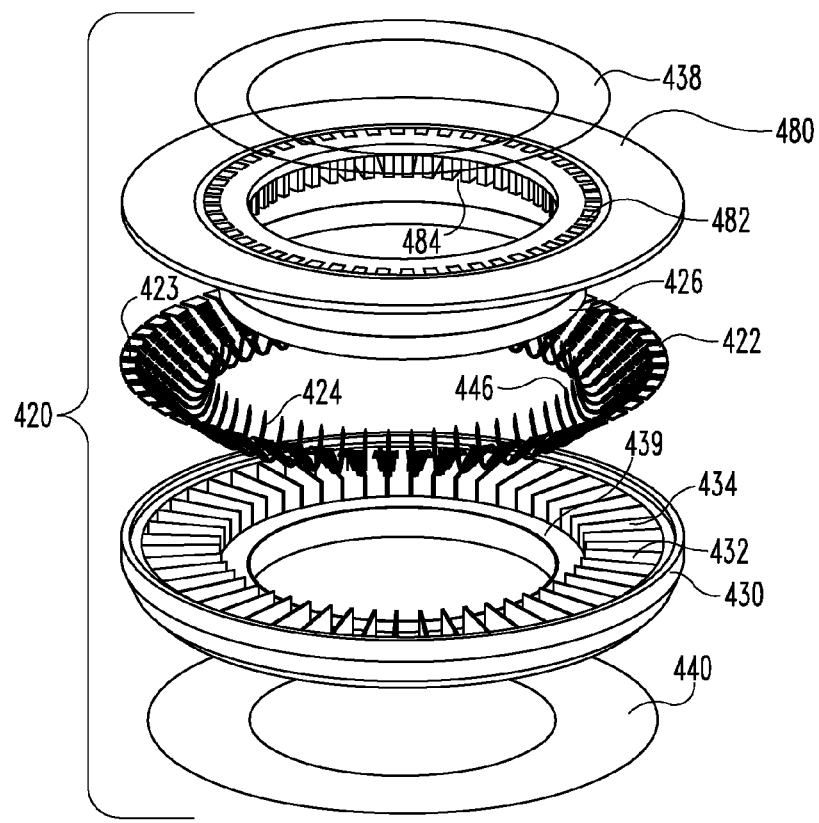
FIG. 33 is an exploded perspective view of an integrated disposable cartridge as viewed from the top of the integrated disposable cartridge.

Similar to cartridge 20, cartridge 420 includes a first sterility sheet 438 as shown in FIG. 33. When cartridge 420 is assembled, the first sterility sheet 438 is positioned to cover and seal one side of a plurality of tester openings 482 of test ring frame 480. As mentioned above, cartridge 420 includes a test ring frame 480. Test ring frame 480 includes a plurality of tester openings 482. Each of the tester openings 482 is sized to receive a lancet tip 446. Test ring frame 480 also includes a plurality of windows 484 and a plurality of frame walls 485 wherein each of windows 484 is positioned between a pair of frame walls 485. Each of the internal windows 484 is positioned between a pair of lancet walls 434 of lancet frame 430 when the test ring frame 480 and lancet frame 430 are assembled. The placement of the windows 484 next to test sections 428 enables an optical device or other device positioned in the center of the cartridge 420 to view a corresponding test section 428 through one of windows 484. In one embodiment, an engagement mechanism can engage one of the frame walls 485 and rotate the cartridge 420 to position a subsequent chamber 432 of lancet frame 430 and corresponding tester opening 482 in line with a driver 436. Each of the plurality of internal windows 484 is rectangular in shape; however, the windows 484 may be configured differently in other embodiments. The plurality of internal windows 484 and plurality of frame walls 485 are positioned to receive a test ring 426.

Figure 34:
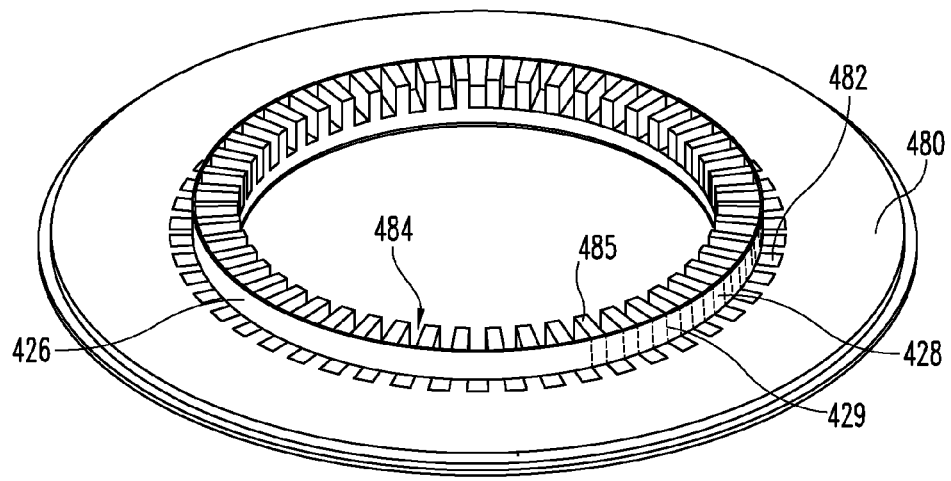
FIG. 34 is a bottom perspective view of a test ring and a test ring frame that is incorporated into the FIG. 33 cartridge.

Test ring 426 includes a plurality of index lines 429 that define a plurality of test sections 428 as illustrated in FIG. 34. The test ring 426 is attached to the plurality of internal windows 484 and plurality of frame walls 485 of the test ring frame 480 such that each of the index lines 429 is in line with each of the lancet walls 434. Moreover, each of test sections 428 is positioned in one of the chambers 432 of the lancet frame 430 such that the corresponding window 484 is aligned with one of a plurality of lancets 424.

Figure 37:
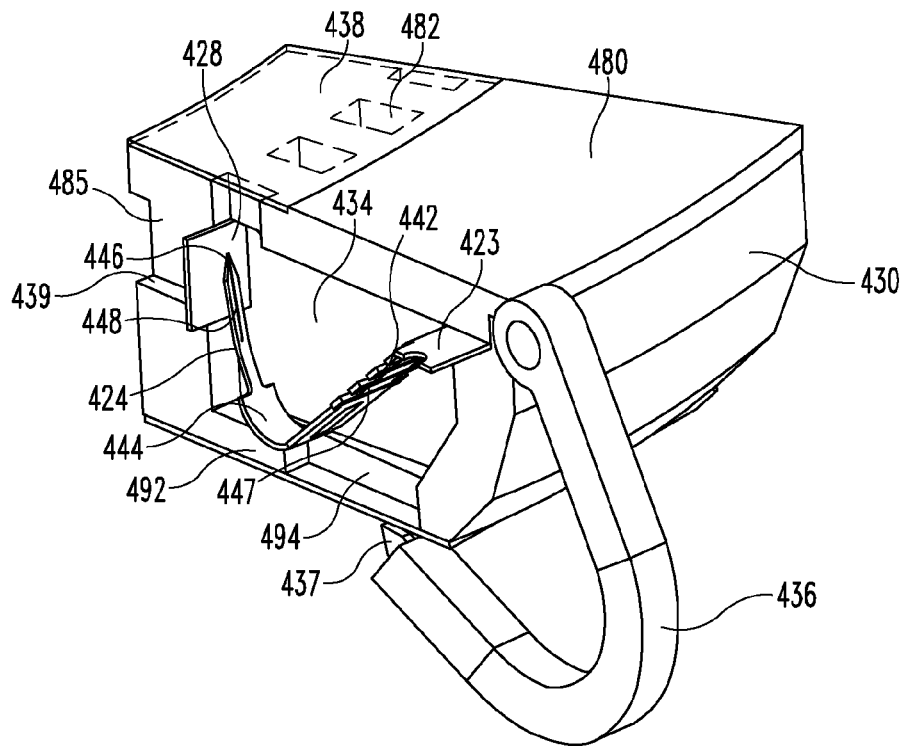
FIG. 37 is a perspective view of a driver that is incorporated into a cross-sectional view of the FIG. 33 integrated disposable cartridge.

As shown in FIGS. 33 and 37, lancet wheel 422 includes a lancet rim 423 with a plurality of lancets 424 extending radially inward from the lancet rim 423. Each of the lancets 424 includes a flexible leg portion 442, a contact portion 444, and a lancet tip 446. The contact portion 444 of each of the lancets 424 is curved and sized to rest on one of a plurality of ledges 492 of the lancet frame 430 when the lancet 424 is at rest. Additionally, in this resting position, the lancet tip 446 does not contact the test section 428. Further the lancet tip 446 fits in the tester opening 482 when the lancet 424 is actuated, as described below. Each of lancets 424 also defines a slot 447 sized to receive a pointed end 437 of a driver 436, as described in more detail below. Lancet tip 446 defines a capillary groove 448. Moreover, after the lancet 424 has been actuated and is in a final position, the lancet tip 446 rests against the test section 428 such that a body fluid sample is transferred from the capillary groove 448 to the test section 428.

Figure 35:
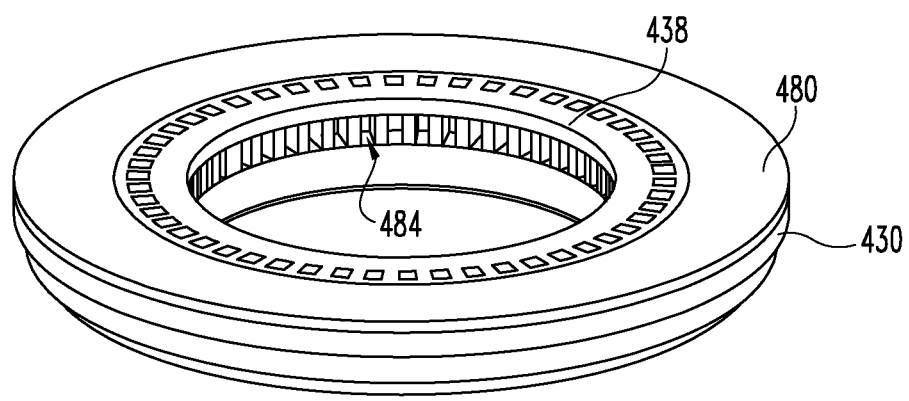
FIG. 35 is a top perspective view of the FIG. 33 integrated disposable cartridge.
Figure 36:
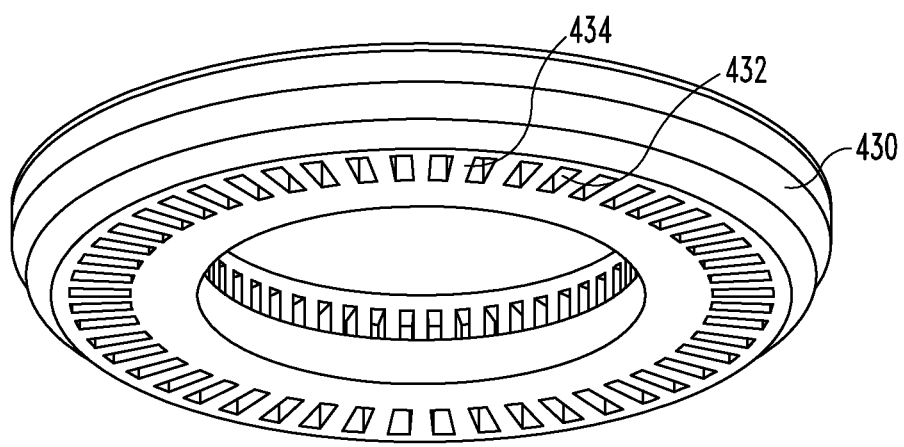
FIG. 36 is a bottom perspective view of the FIG. 33 integrated disposable cartridge.

Lancet frame 430 in FIGS. 33, 35, and 36 is configured a little different than frame 30 illustrated in FIGS. 1 and 2. Lancet frame 430 in FIG. 33 includes a plurality of walls 434 that define a plurality of chambers 432. Lancet frame 430 includes a rim 439 that is sized to receive the plurality of frame walls 485 to position the test ring frame 480 on the lancet frame 430. The lancet frame 430 also includes a plurality of ledges 492. Each of the ledges 492 is sized to receive the contact portion 444 of the lancet 424. One of the ledges 492 is positioned in each of the plurality of chambers 432. In the illustrated embodiment, each of the plurality of ledges 492 is substantially flat. A plurality of openings 494 are positioned between the plurality of walls 434 and the plurality of ledges 492. Each of the openings 494 is sized to receive a driver 436. As illustrated in FIGS. 37, 38, 39, and 40, driver 436 includes a sharp or pointed end 438 to pierce through second sterility sheet 440 placed over the openings 494, as described below. Pointed end 438 enters slot 447 of lancet 424 to actuate the lancet 424, as described below.

As shown in FIG. 33, cartridge 420 includes a second sterility sheet 440 positioned to cover and seal the plurality of chambers 432 of the lancet frame 430. First sterility sheet 438, test ring 426, and second sterility sheet 440 are configured to cover and seal the plurality of tester openings 482, the plurality of chambers 432, and the plurality of internal windows 484 to form an air-tight cartridge 420. Similarly, first sterility sheet 38, test ring 26, and sterility sheet 40 of cartridge 20 are configured to form an air-tight cartridge 20.

To use cartridge 420, a user positions a body part to be lanced, most likely a finger, over a currently active one of the plurality of tester openings 482. The driver 436 is actuated to pierce through the second sterility sheet 440, pass through the corresponding opening 494, and enter the chamber 432. The driver 436 continues moving into the chamber 432, and the pointed end 438 of the driver 436 engages the slot 447 of the active lancet 424. As the driver 436 engages the slot 447, the driver 436 applies a force to the leg portion 442 to move the lancet tip 446 in a direction orthogonal to the frame 430. As the lancet tip 446 moves, the lancet tip 446 pierces through the first sterility sheet 438 and continues into the skin of the user that has been placed over the active tester opening 482. In one embodiment, as the lancet tip 446 forms an incision, the body fluid sample from the incision travels along the capillary groove 448 via capillary action towards the contact portion 444 and the capillary groove 448 collects the body fluid sample from the incision while the lancet tip 446 is in the skin of the user. In one embodiment, an adequate sample size of body fluid is approximately 90 nanoliters.

After the driver 436 reaches its maximum extension position, the driver 436 stops and reverses its path of movement.

As the driver 436 reverses its path of movement, the force applied to the leg portion 442 is reduced and the lancet tip 446 withdraws from the incision. Due to the resilient nature of each lancet 424, the lancet tip 446 springs back to its original position in the chamber 432 on its own. In this final position, the lancet tip 446 of the active lancet 424 contacts the test section 428 and the body fluid sample is released from the capillary groove 448 onto the test section 428 by preferential capillarity between the lancet tip 446 of the lancet 424 and the chemistry on the test section 428. The lancet 424 remains in its final resting position with the contact portion 444 resting against the ledge 492. For the next test, an actuation mechanism retracts the driver 436 and rotates the test ring frame 480 so as to align the next corresponding tester opening 482 and the next unused or sterile lancet 424 with the driver 436.

A lancet frame 530, a lancet wheel 522, and a test ring 526 according to another embodiment are illustrated in FIGS. 41, 42, 43, and 44. As should be recognized from these figures, the lancet frame 530 shares a number of features in common with lancet frame 430 illustrated in FIGS. 33, 35, and 36. Therefore for the sake of brevity features from the lancet frame 530 that are similar to the lancet frame 430 will not be discussed. Unlike lancet frame 430, lancet frame 530 has a plurality of ledges 592 that are configured to retain a lancet in a flexed position prior to actuation. Due to the resiliency of the lancet and the configuration of each of the ledges 592, after the lancet is released from its corresponding ledge 592, it springs back to its original unflexed configuration and the lancet is lifted to form an incision. In other words, the tension imposed on the lancet from the ledge 592 is released. After the lancet forms an incision and the lancet returns to its corresponding ledge 592, the lancet tip contacts a test section 528 and transfers a body fluid sample to the test section 528. The transfer of a body fluid sample from the lancet tip to a test section as compared to the transfer of a body fluid sample from a contact portion of a lancet to a test section requires less travel distance for the body fluid sample before the body fluid sample is transferred to a test section. A transfer of the body fluid sample from the lancet tip as compared to other portions of the lancet results in higher success rates for lancing and testing events. In some clinical trials of this embodiment and the embodiments shown in FIGS. 33, 34, 35, 36, 37, 38, and 39, the success rate for lancet tip transfer of a bodily fluid sample to a test section was greater than 93%. In some embodiments, the total testing time including forming an incision, collecting a bodily fluid sample, and analyzing the bodily fluid sample is less than 1 second.

Lancet frame 530 includes a plurality of walls 534 that define a plurality of chambers 532. Lancet frame 530 also includes a plurality of ledges 592. Each of the ledges 592 is sized to receive the contact portion 544 of the lancet 524. One of the ledges 592 is positioned in each of the plurality of chambers 532. In the illustrated embodiment, the plurality of ledges 592 is substantially rectangular. Each of the ledges 592 also contains a notch 593 configured to receive the lancet tip 546, as explained in more detail below. A plurality of openings 594 are positioned between the plurality of walls 534 and the plurality of ledges 592. Each of the openings 594 is sized to receive a driver.

Figure 41:
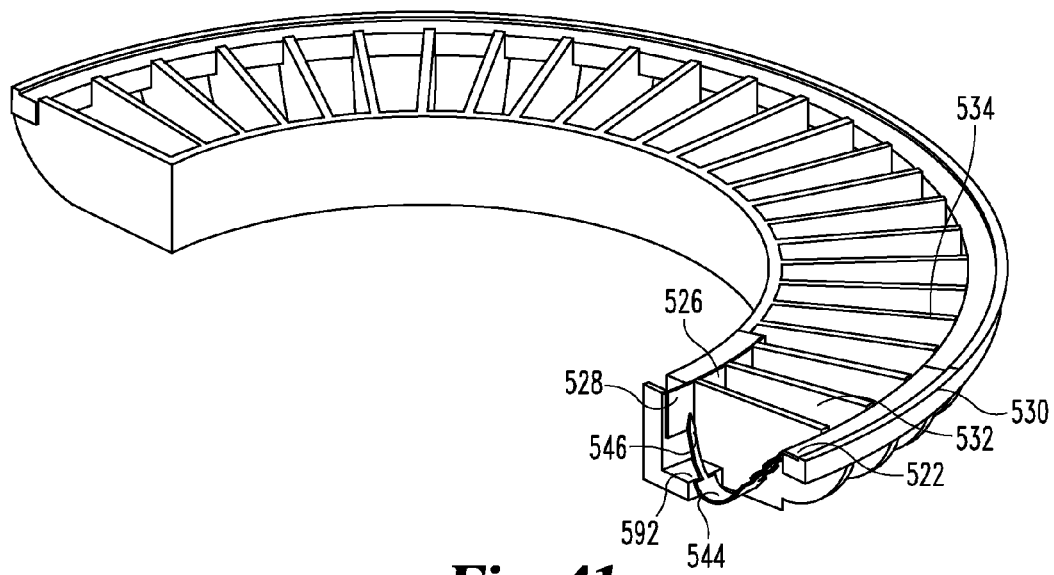
FIG. 41 is a top perspective view of a lancet frame, lancet wheel, and test ring according to another embodiment.

A lancet wheel 522 is positioned in the lancet frame 530 as shown in FIG. 41. Lancet wheel 522 shares a number of features in common with lancet wheel 422 illustrated in FIGS. 33 and 37. Therefore for the sake of brevity, common features from the lancet wheel 522 and lancet wheel 422 will not be discussed.

Test ring 526 is illustrated in FIG. 41. Test ring 526 shares a number of features in common with test ring 426 illustrated in FIGS. 33 and 37. Therefore for the sake of brevity common features from the test ring 526 and the test ring 426 will not be discussed. Test ring 526 includes a plurality of test sections 528. Test ring 526 is positioned on the lancet frame 530 such that each of the test sections 528 is positioned between a pair of walls 534 of the lancet frame 530.

In an initial position, the lancet tip 546 is positioned in the notch 593 such that the contact portion 544 rests against the ledge 592 to restrain the lancet 524 from movement until a driver engages the lancet 524 to release the lancet tip 546 from the notch 593. In this initial position, each of the ledges 592 extends towards the lancet rim 523 to bend the contact portion 544 towards flexible leg portion 542. As the lancet 524 moves from the initial position to an incision forming position, the contact portion 544 passes over both the notch 593 and the ledge 592 and the lancet tip 546 moves in a direction orthogonal to the lancet frame 530. After the contact portion 544 passes over the ledge 592, the contact portion 544 springs back to its original configuration due to the resilient nature of each lancet 524. As the lancet tip 546 moves, the lancet tip 546 pierces the skin of the user that has been placed over the corresponding chamber 532. In one embodiment, as the lancet tip 546 forms an incision, the body fluid sample from the incision travels along the capillary groove 548 via capillary action towards the contact portion 544 and the capillary groove 548 collects the body fluid sample from the incision while the lancet tip 546 is in the skin of the user. After a driver or other mechanism reaches its final extension position, the driver stops and reverses its path of movement. As the driver reverses its path of movement, the force applied to the leg portion 542 is reduced and the lancet tip 546 withdraws from the incision. In its final position, the contact portion 544 of the active lancet 524 rests against the ledge 592 and the bodily fluid sample is transferred from the capillary groove 548 to the corresponding test section 528.

Figure 45:
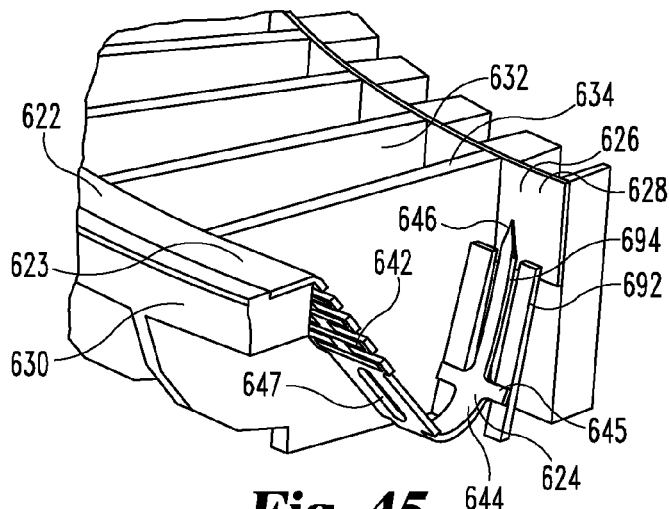
FIG. 45 is a perspective view of a lancet frame, lancet wheel, and test ring according to another embodiment that depicts a lancet in an initial position.
Figure 46:
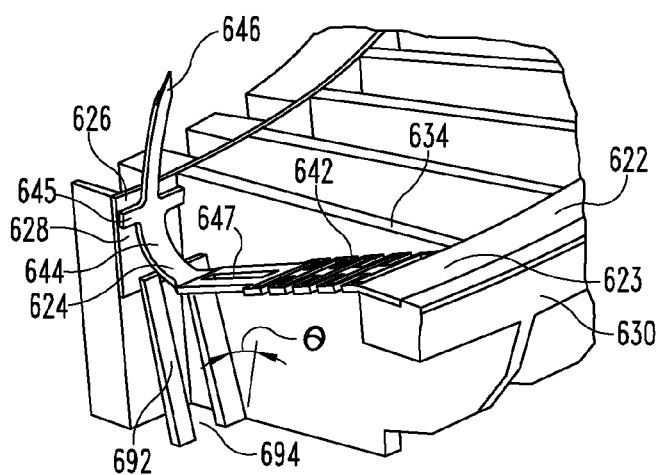
FIG. 46 is a perspective view of the FIG. 45 mechanism that depicts the lancet in a fully actuated position.
Figure 47:
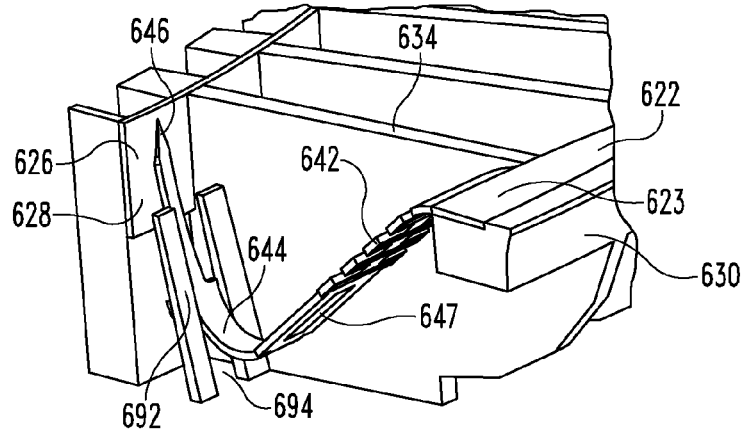
FIG. 47 is a perspective view of the FIG. 45 mechanism that depicts the lancet in a final position.

A lancet frame 630, a lancet wheel 622, and a test ring 626 according to another embodiment are illustrated in FIGS. 45, 46, and 47. As should be recognized from these features, lancet frame 630 shares a number of features in common with lancet frame 430 illustrated in FIGS. 33, 35, and 36. Therefore for the sake of brevity, common features from lancet frame 630 and lancet frame 430 will not be discussed. As described below, lancet frame 630 includes a plurality of slats 692 that are configured to restrain the plurality of lancets 624 such that the plurality of lancets 624 do not contact the plurality of test sections 628 prior to actuation. Beneficially, the plurality of slats 692 are configured to force the lancet tip 646 to contact a test section and transfer a body fluid sample to the test section after the lancet tip 646 has collected a body fluid sample. As mentioned above, the transfer of body fluid from the lancet tip requires less blood travel distance than compared to the transfer of body fluid from the contact section or any other section of the lancet. Also beneficially, the plurality of slats 692 restrains the contaminated lancets 624 after a testing event.

Lancet frame 630 includes a plurality of walls 634 that define a plurality of chambers 632 as shown in FIGS. 45, 46, and 47. The lancet frame 630 also includes a plurality of slats 692. A pair of the slats 692 is positioned in each of the plurality of chambers 632. Each of the slats 692 is attached to one of the walls 634. Between each of the pairs of slats 692 is a slat opening 694. The pair of slats 692 is sized and positioned on the walls 634 to receive the lancet tip 646 of the lancet 624 in the slat opening 694 when the lancet 624 is in an initial position. The pair of slats 692 is also sized and positioned to restrain the lancet 624 when the lancet 624 is in its final position. After the lancet 624 has been actuated and rests in a final position, the pair of slats 692 restrains the pair of tabs 645 between the pair of slats 692 and the lancet frame 630. In the illustrated embodiment, each of the plurality of slats 692 is substantially rectangular. Each of the plurality of slats 692 forms an angle θ with each of the walls 634. Angle θ is an acute angle.

Figure 38:
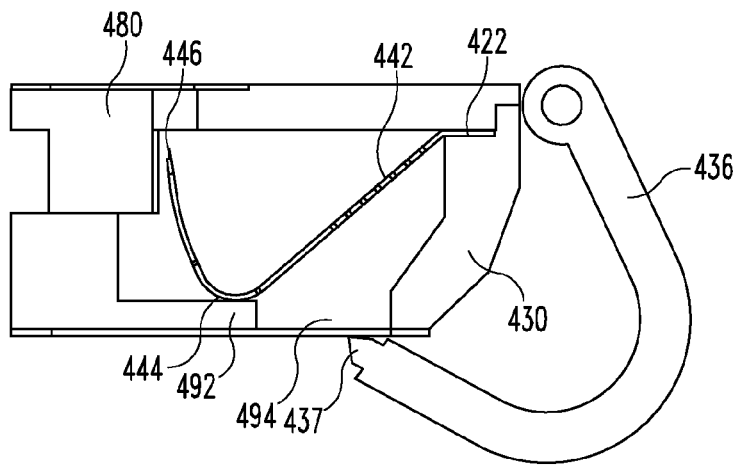
FIG. 38 is a side view of the FIG. 37 mechanism.
Figure 39:
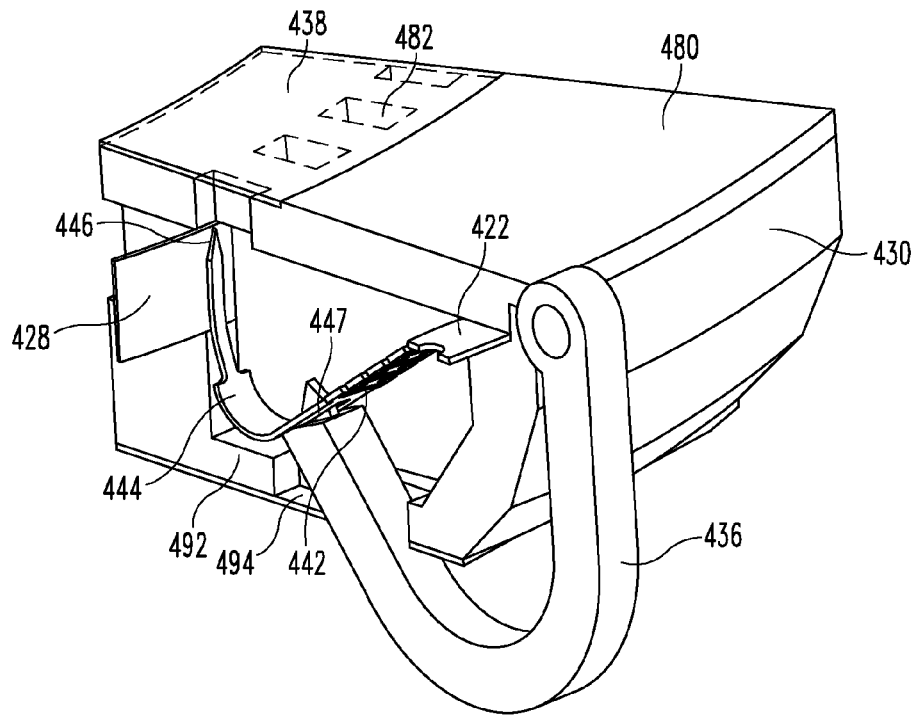
FIG. 39 is a perspective view of the FIG. 37 mechanism with the driver in a partially actuated position.
Figure 40:
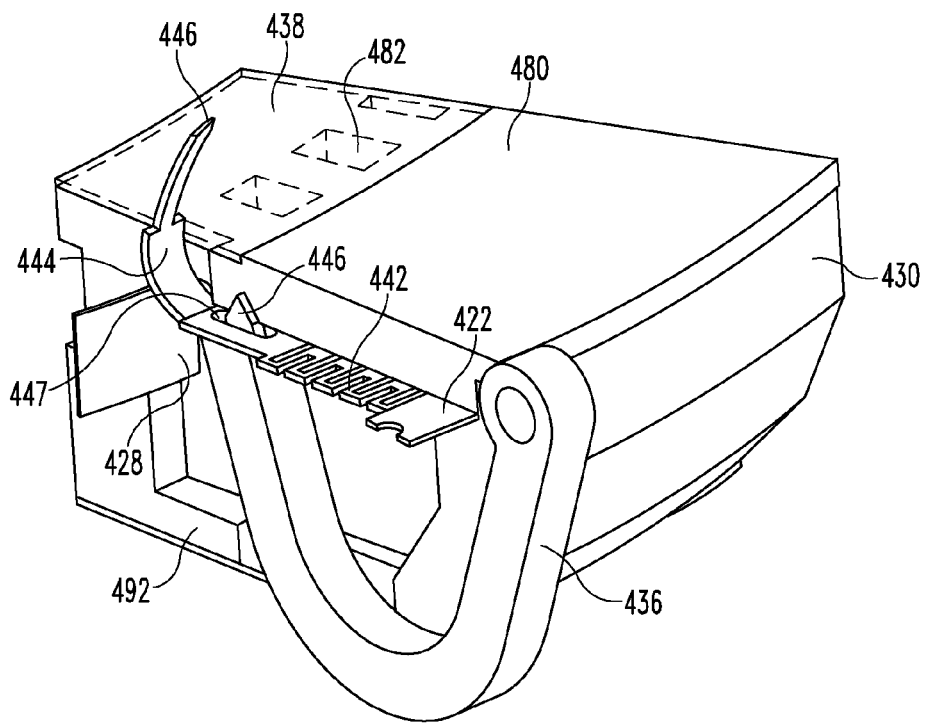
FIG. 40 is a perspective view of the FIG. 37 mechanism with the driver in a fully actuated position.

A lancet wheel 622 is positioned in the lancet frame 630 as shown in FIG. 45. Lancet wheel 622 includes a number of features in common with lancet wheel 422 as shown in FIGS. 33, 37, and 38; therefore for the sake of brevity common features from the lancet wheel 622 and the lancet wheel 422 will not be discussed. Lancet wheel 622 includes a lancet rim 623 with a plurality of lancets 624 extending radially inward from the lancet rim 623. Each of the lancets 624 includes a flexible leg portion 642, a contact portion 644, and a lancet tip 646. The contact portion 644 of each of the lancets 624 includes a pair of tabs 645 sized to rest on the pair of slats 692 of the lancet frame 630 when the lancet 624 is in an initial position. After the lancet 624 has been actuated and rests in its final position, the pair of slats 692 restrains the pair of tabs 645 between the pair of slats 692 and the lancet frame 630. Each of lancets 624 also defines a slot 647 sized to receive a pointed end of a driver. In one embodiment, lancet tip 646 defines a capillary groove (not illustrated).

Figure 42:
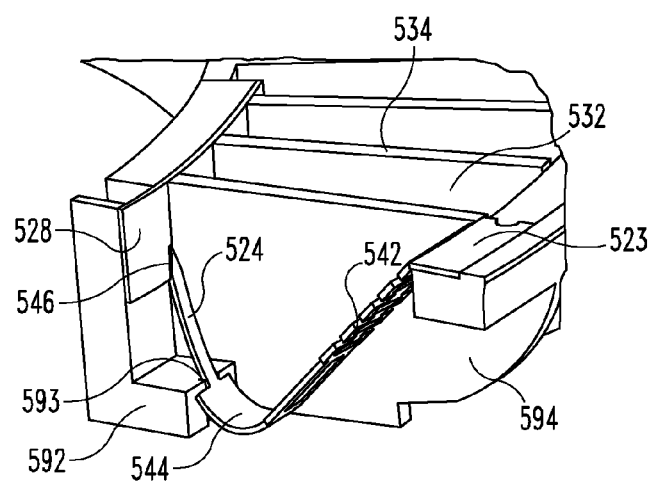
FIG. 42 is a perspective view of the FIG. 41 mechanism that depicts a lancet in an initial position.
Figure 43:
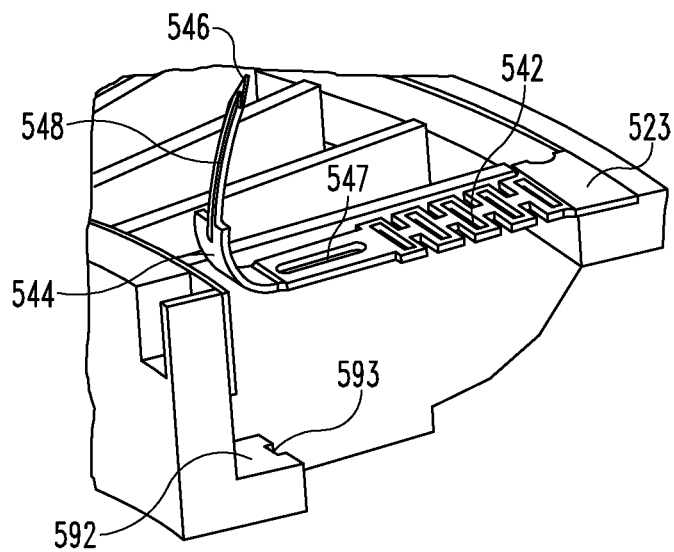
FIG. 43 is a perspective view of the FIG. 42 mechanism that depicts the lancet in a fully actuated position.
Figure 44:
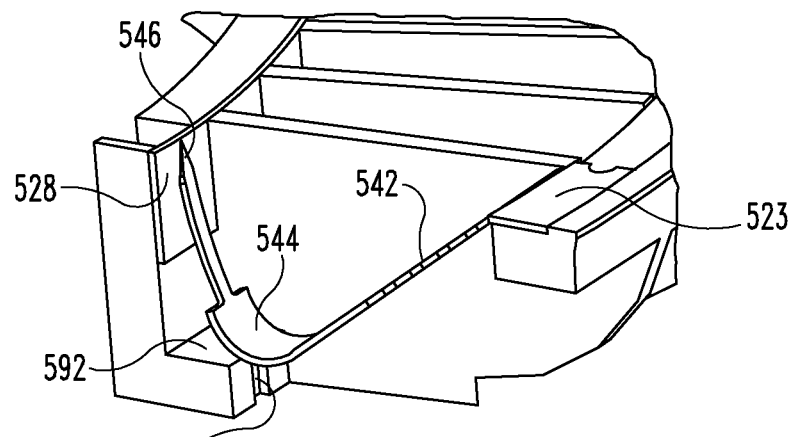
FIG. 44 is a perspective view of the FIG. 42 mechanism that depicts the lancet in a final position.

Test ring 626 shares a number of common features with test ring 526 illustrated in FIGS. 41, 42, and 44; therefore for the sake of brevity common features from the test ring 626 and the test ring 526 will not be discussed. Test ring 626 includes a plurality of test sections 628. Test ring 626 is positioned on the lancet frame 630 such that each of the test sections 628 is positioned between a pair of walls 634 of the lancet frame 630.

In an initial position, the lancet tip 646 is positioned in the slat opening 694 such that the pair of tabs 645 rest against the pair of slats 692 to restrain the lancet 624 from movement until a driver engages the lancet 624 to move the lancet 624 and release the pair of tabs 645 from the pair of slats 692. Additionally, in the initial position, the resiliency of the lancet 624 causes the contact portion 644 to bend as the pair of tabs 645 push against the slats 692. As the driver moves the lancet 624 from the initial position to an incision forming position, the contact portion 644 passes over the pair of slats 692 and the compressive force on the contact portion 644 is released. Due to the resilient nature of each lancet 624, the lancet tip 646 springs to an uncompressed configuration. The lancet tip 646 moves in a direction orthogonal to the lancet frame 630 when the lancet 624 moves from the initial position to the incision forming position. As the lancet tip 646 moves, the lancet tip 646 pierces the skin of the user that has been placed over the corresponding chamber 632. In one embodiment, as the lancet tip 646 forms an incision, the body fluid sample from the incision travels along a capillary groove via capillary action towards the contact portion 644 and the capillary groove collects the body fluid sample from the incision while the lancet tip 646 is in the skin of the user. After a driver or other mechanism reaches its final extension position, the driver stops and reverses its path of movement. As the driver reverses its path of movement, the force applied to the leg portion 642 is reduced and the lancet tip 646 withdraws from the incision. Since the lancet 624 has returned to an uncompressed configuration, the pair of tabs 645 slide behind the pair of slats 692 to restrain the lancet 624 in a final position and allow the lancet tip 646 to engage the test section 628. In its final position, the lancet 624 rests against the test section 628 and the bodily fluid sample is transferred from the capillary groove or the lancet tip 646 to the corresponding test section 628.

Figures 48A, 49A, 50A:
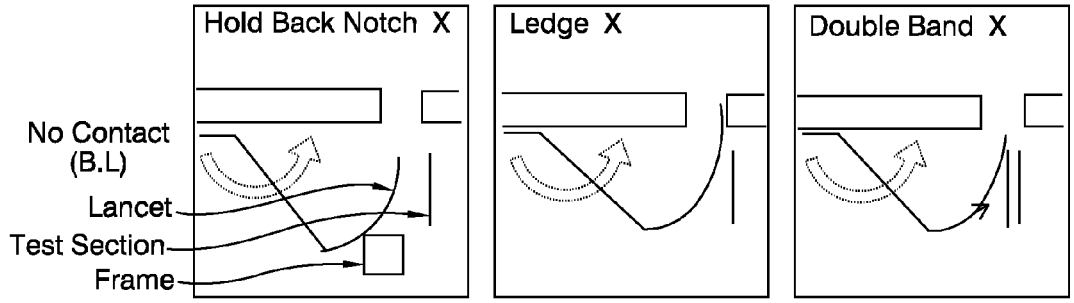
FIGS. 48, 49, 50, 51, 52, and 53 are schematical representations of various techniques of actuating a lancet and transferring the body fluid sample to a test section.
Figures 48B, 49B, 50B:
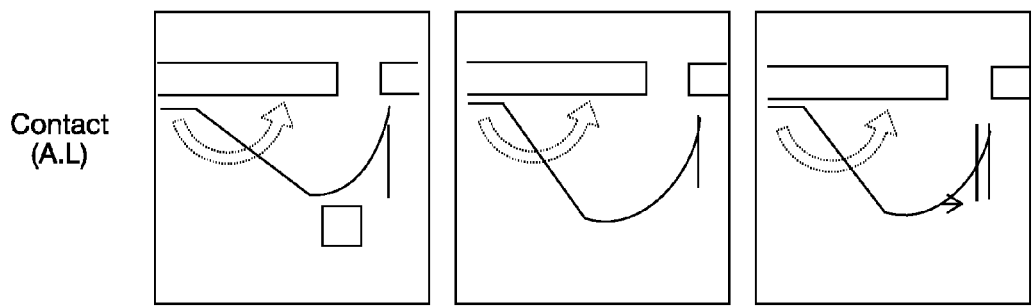

FIGS. 48A and 48B are schematic representations of one technique of restraining a lancet prior to actuation such that the lancet does not contact the test section. As illustrated in FIG. 48A, the lancet rests against a notch in a frame such that the position of the frame results in a compressive force in the lancet. After the lancet is actuated, the lancet is released from the notch and returns to an uncompressed state. The lancet then forms an incision and collects a body fluid sample in the lancet tip. As shown in FIG. 48B, the lancet tip in an uncompressed state touches a test section to transfer the body fluid sample from the lancet to the test section. The position of the test section allows the uncompressed lancet to engage the test section and transfer the body fluid sample to it. Beneficially, the lancet does not contact the test section unless the lancet is transferring a body fluid sample to the test section therefore the test chemistry remains intact. Resiliency of the lancet allows it to return to an uncompressed state after it is released from the notch therefore no additional mechanisms are required to cause the lancet to return to an uncompressed state and transfer a body fluid sample to the test section.

FIGS. 49A and 49B are schematic representations of another technique of restraining a lancet prior to actuation such that the lancet does not contact the test section. Beneficially, the test chemistry on the test section remains intact and untouched. As shown in FIG. 49A, the lancet rests against a ledge such that the position of the ledge results in a compressive force in the lancet. After the lancet is actuated, the lancet is released from the ledge and returns to an uncompressed state. The lancet then forms an incision and collects a body fluid sample in the lancet tip. As shown in FIG. 49B, the lancet tip in an uncompressed state touches a test section to transfer the body fluid sample from the lancet to the test section. Beneficially no other mechanisms are required to cause the lancet to return to an uncompressed state and transfer a body fluid sample to the test section. The position of the test section allows the uncompressed lancet to engage the test section and transfer the body fluid sample to it.

FIGS. 50A and 50B are schematic representations of yet another technique of restraining a lancet prior to actuation such that the lancet does not contact the test section therefore the test chemistry on the test section remains intact and untouched. In a first position shown in FIG. 50A, a first band restrains a lancet such that the position of the band results in a compressive force in the lancet and the lancet is flexed or bent. Next, the lancet is actuated and the lancet pierces through the first band to form an incision in skin and collect a body fluid sample. During actuation the lancet returns to its uncompressed shape. As shown in FIG. 50B, after collecting the body fluid sample the lancet tip contacts a second band that includes a test section as the lancet returns to the first position. The body fluid sample in the lancet tip is transferred from the lancet tip to the test section on the second band.

Figures 51A, 52A, 53A:
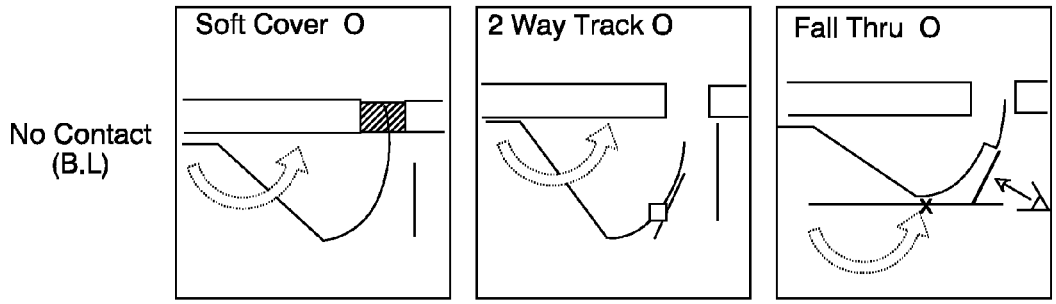
Figures 51B, 52B, 53B:
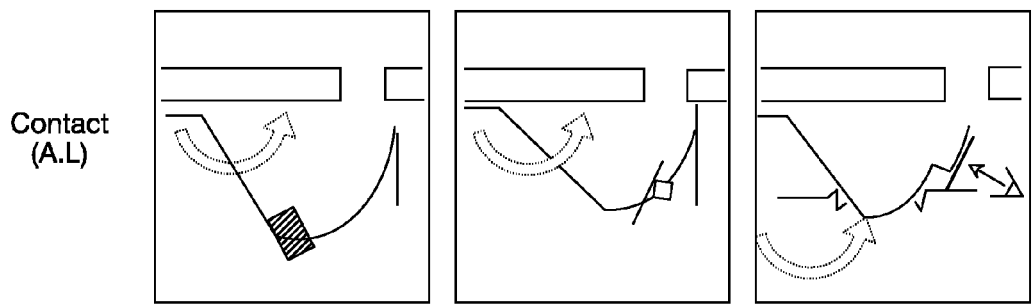

FIGS. 51A and 51B are schematic representations of yet another technique of restraining a lancet prior to actuation such that the lancet does not contact the test section therefore the test chemistry on the test section remains intact and untouched. As shown in FIG. 51A, the lancet tip rests in a cover made of a soft material such that the position of the cover results in a compressive force in the lancet. After the lancet is actuated, the lancet is driven through the soft cover and returns to an uncompressed state. After the lancet is driven through the cover, the cover then slides down a portion of the lancet as the lancet tip forms an incision and collects a body fluid sample. As shown in FIG. 51B, the lancet has returned to its original position and the lancet tip touches a test section to transfer the body fluid sample from the lancet to the test section. Beneficially no other mechanisms are required to cause the resilient lancet to return to an uncompressed state and transfer a body fluid sample to the test section. The position of the test section allows the uncompressed lancet to engage the test section and transfer the body fluid sample to it.

FIGS. 52A and 52B are schematic representations of one technique of restraining a lancet prior to actuation such that the lancet does not contact the test section therefore the test chemistry on the test section remains intact and untouched. As shown in FIG. 52A, the lancet includes a tab that rides along a track such that the position of the track causes the lancet to bend or compress. After the lancet is actuated, the tab is driven along the track until the tab clears the track thereby releasing the compressive force on the lancet and the lancet returns to an uncompressed state. After the tab has cleared the track, the lancet tip forms an incision and collects a body fluid sample. As shown in FIG. 52B, the lancet tip touches a test section to transfer the body fluid sample from the lancet to the test section as the lancet returns to its original position. Beneficially no other mechanisms are required to cause the resilient lancet to return to an uncompressed state and transfer a body fluid sample to the test section. The position of the test section allows the uncompressed lancet to engage the test section and transfer the body fluid sample to it.

FIGS. 53A and 53B are schematic representations of another technique of restraining a lancet prior to actuation such that the lancet does not contact the test section therefore the test chemistry on the test section remains intact and untouched. As shown in FIG. 53A, the lancet is in a bent configuration resting against a bottom layer of a lancet frame. In one form, the bottom layer is a sterility sheet. The bottom layer of the lancet frame is configured such that the driver breaks through it. After forming an incision and collecting a body fluid sample, the lancet falls through the bottom layer of the lancet frame, and the lancet then touches a test section to transfer the body fluid sample from the lancet to the test section.

A portable meter system 1000 according to one embodiment is illustrated in FIGS. 54, 55, 56, 57, 58, 59, 60, 61, 62, 63, 64, 65, 66, 67, 68, 69, and 70. Although the portable meter system 1000 will be described with reference to portable blood glucose testing, it should be appreciated that the meter system 1000 can be adapted to test a wide variety of biological fluids and fluid properties. Looking at FIGS. 54 and 55, the meter system 1000 includes a housing 1002 that houses the lancet frame 130, lancet wheel 122, and test ring 126. Schematically only lancet frame 130 is shown in the meter system 100 for clarity although the meter system 1000 will be described with reference to the lancet wheel 122 and test ring 126. Although the portable meter system 1000 will be described with reference to lancet frame 130, lancet wheel 122, and test ring 126, it should be appreciated that the meter system 1000 can be adapted to the above listed cartridges and/or lancet frames, lancet wheels, and test rings.

Figure 54:
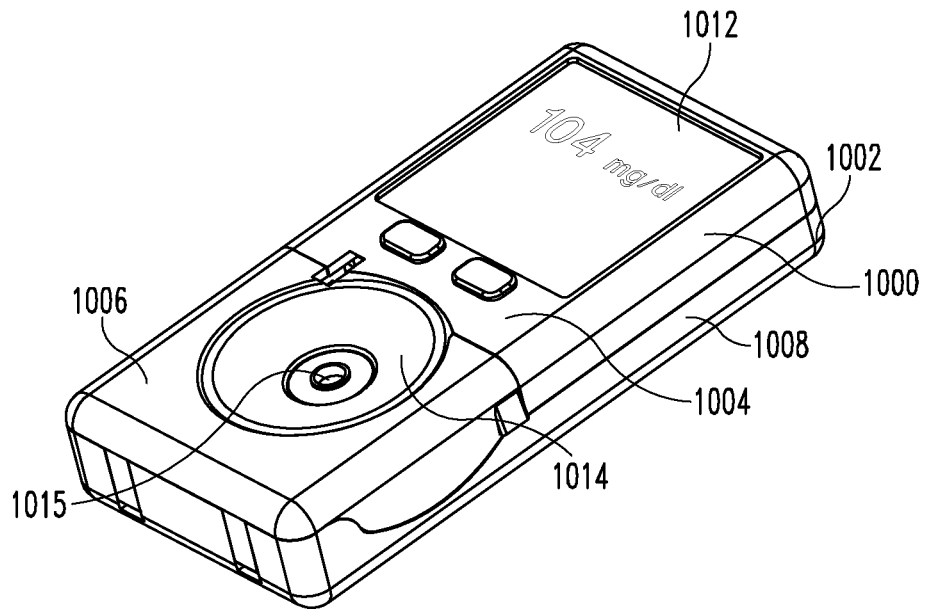
FIG. 54 is a perspective view of a portable meter system according to one embodiment.
Figure 55:
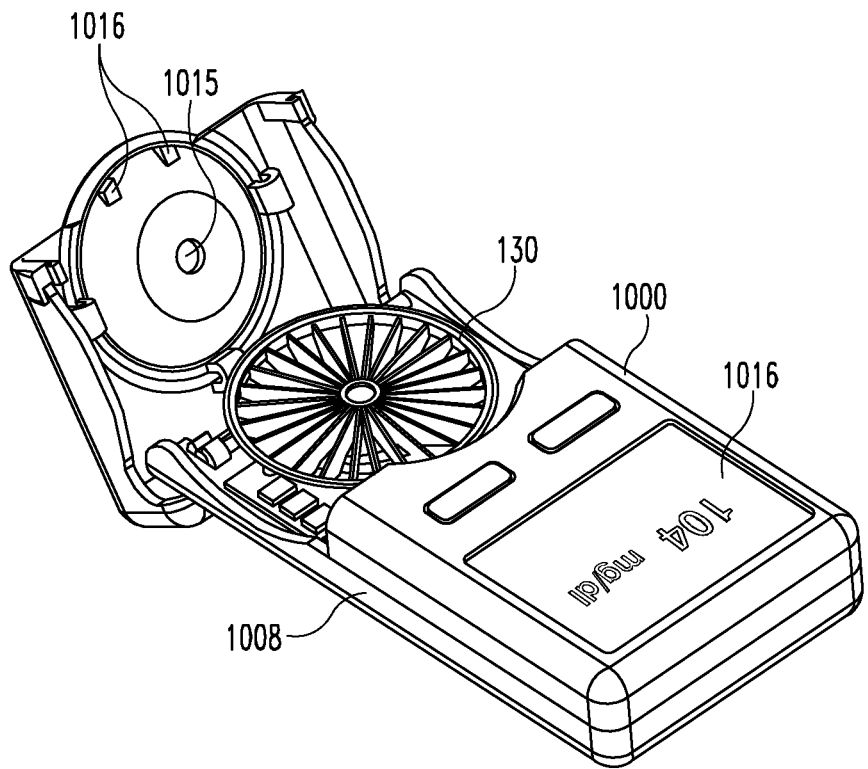
FIG. 55 is a top view of a lancet frame, lancet wheel, and test ring loaded in the FIG. 54 mechanism with the lid open.
Figure 56:
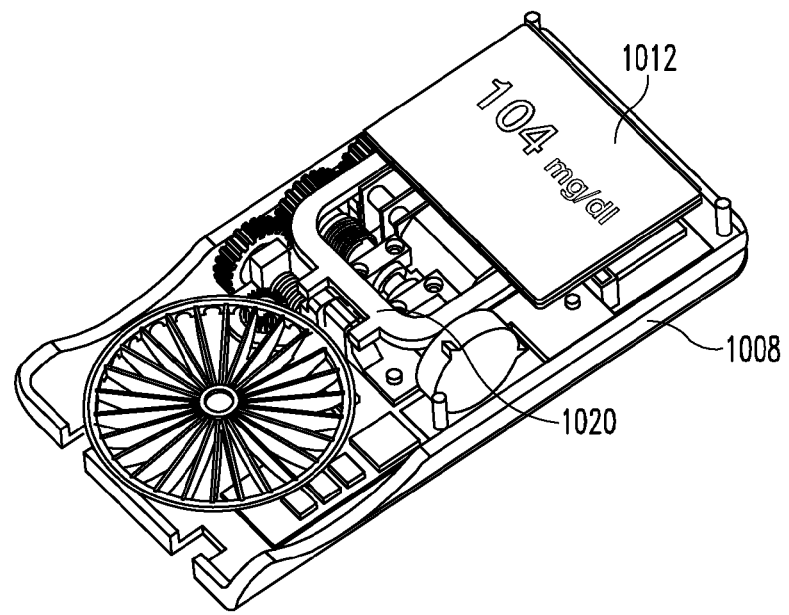
FIG. 56 is a top perspective view of the FIG. 54 mechanism with the top cover removed.
Figure 57:
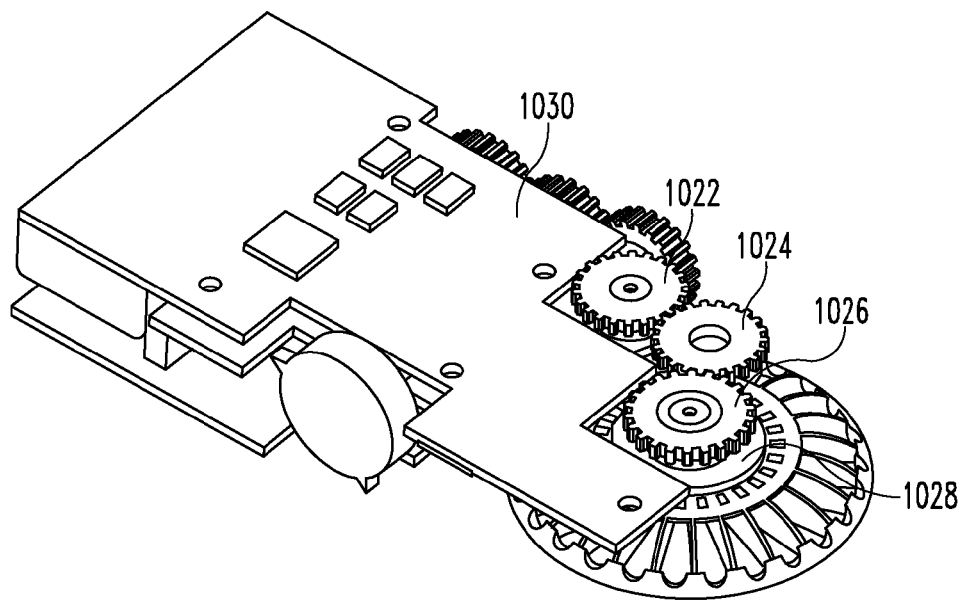
FIG. 57 is a bottom perspective view of the FIG. 56 mechanism with the top and bottom covers removed.
Figure 58:
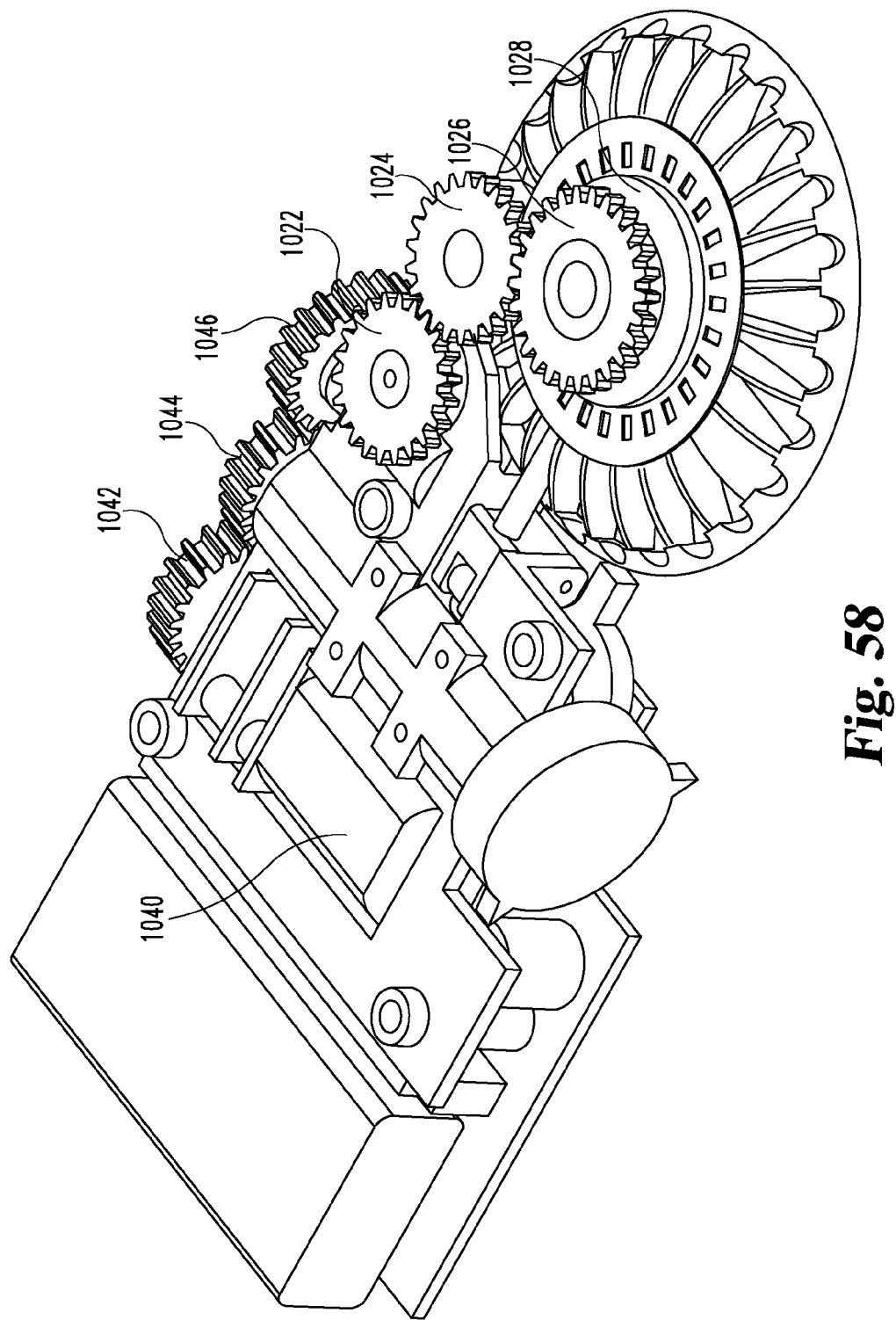
FIG. 58 is a bottom perspective view of the FIG. 57 mechanism with the lower printed circuit board removed.
Figure 59:
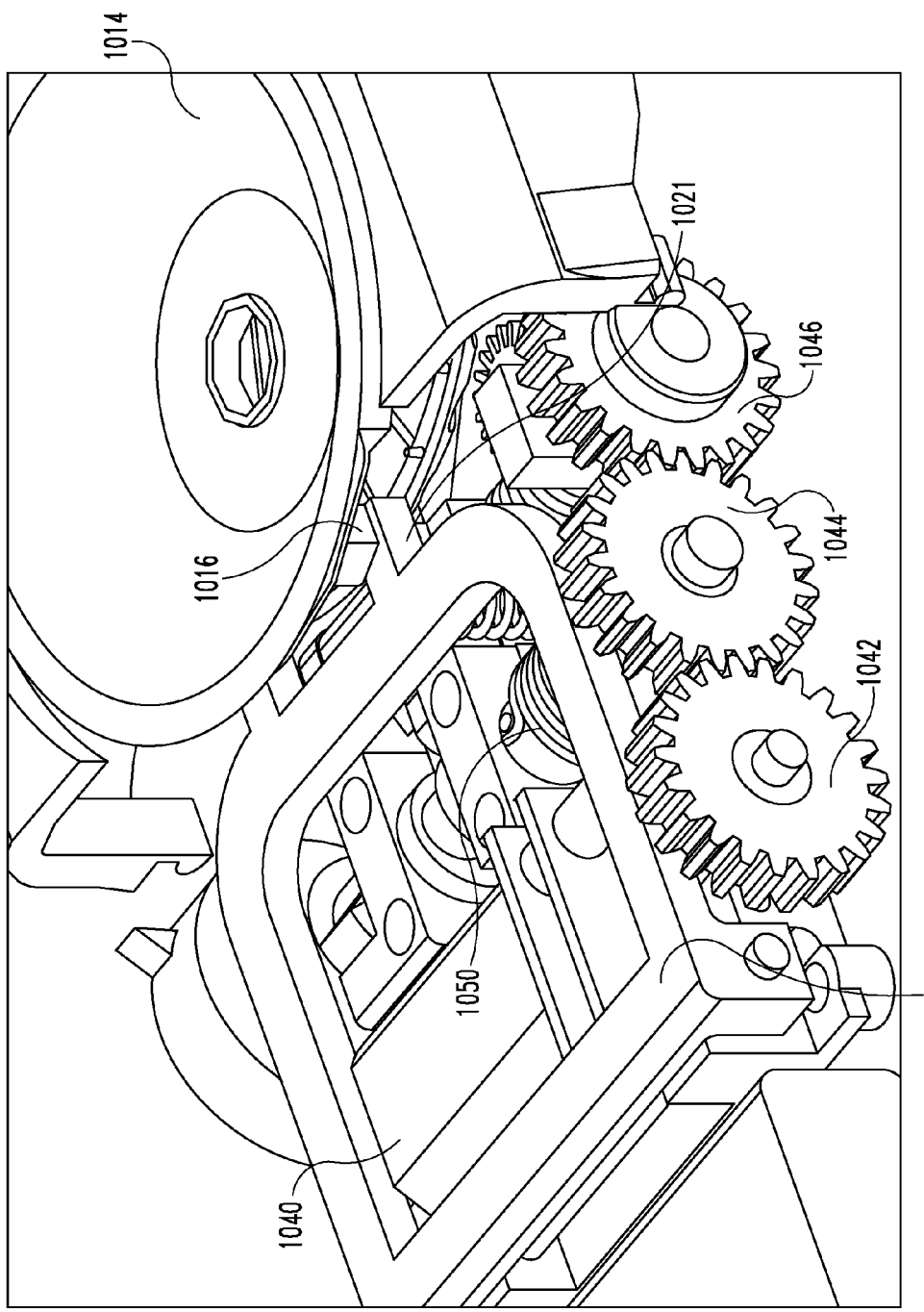
FIG. 59 is a partial top perspective view of the FIG. 58 mechanism with the upper printed circuit board removed.

The housing 1002 includes a front cover 1004, a door 1006, and a base 1008 as illustrated in FIGS. 54 and 55. The front cover 1004 has a display 1012 for displaying test results as well as other information. It should be appreciated that the meter system 1000 can include other output devices, like a speaker, for example. Display 1012 is positioned such that the user can readily view the display 1012 when the meter system 1000 is gripped in the hand of the user. The door 1006 includes a pressure cup 1014 sized to receive a fingertip of a user. The pressure cup 1014 is made from an elastic-type supported plastic material to allow for movement of the pressure cup 1014 to transfer force from finger pressure of the user to release arm 1020 in the meter system 1000 to fire the lancet 124, as described in more detail below. The pressure cup 1014 is positioned over the lancet frame 130, lancet wheel 122, and the test ring 126 to advance the lancet frame 130, lancet wheel 122, and the test ring 126 for each lancing event. The pressure cup 1014 defines an opening 1015 in which the lancet 124 exits to form an incision in skin. The back surface of the pressure cup 1014 has a pair of trigger contact tabs 1016 positioned to engage a pair of tabs 1021 of release arm 1020 to actuate the lancet 124, as described in more detail below. In one embodiment, the door 1006 is hingedly attached to the base 1008 to allow access to the interior of the meter system 1000. As such, a used lancet frame 130, lancet wheel 122, and test ring 126 can be replaced with a clean or new lancet frame, lancet wheel, and test ring. In other embodiments, the door 1006 can be attached to base 1008 by another mechanism.

The portable meter system 1000 includes a release arm 1020. Release arm 1020 has a pair of tabs 1021 configured to contact the pair of trigger contact tabs 1016. Release arm 1020 includes a trigger 1062 positioned to engage a latch and thereby release spring motor 1050. The portable meter system 1000 also includes a first gear 1022, a second gear 1024, and a third gear 1026 that interact with each other to rotate the lancet frame 130, lancet wheel 122, and the test ring 126 to advance the lancet frame 130, lancet wheel 122, and the test ring 126 for each lancing event. Gear 1026 is mounted to a platform 1028 in which the lancet frame 130, lancet wheel 122, and the test ring 126 have also been attached. First gear 1022 is driven by fourth gear 1024, as described in more detail below. Due to the interaction of gears 1022, 1024, and 1026, the rotational movement of gear 1022 causes gears 1024 and 1026 to rotate.

Figure 64:
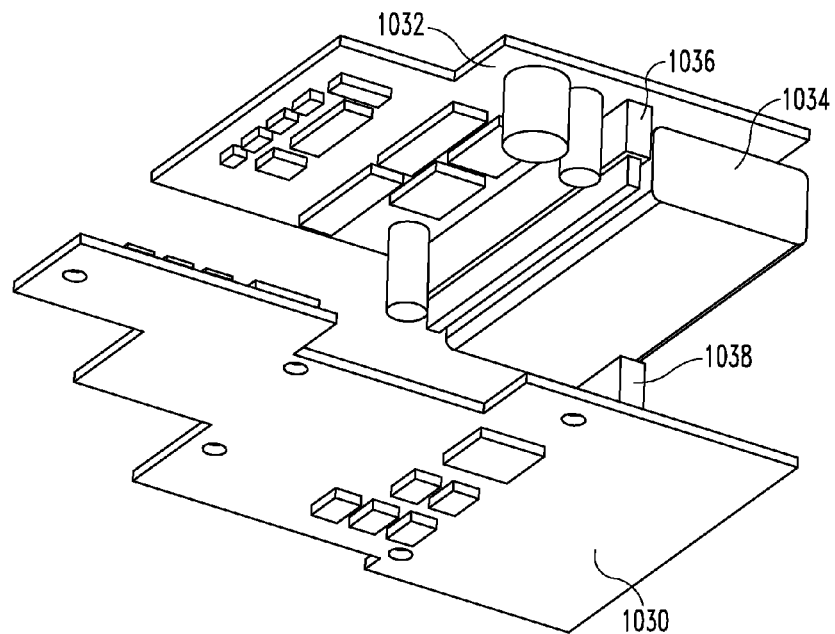
FIG. 64 is a bottom perspective view of the upper printed circuit board, lower printed circuit board, and battery.
Figure 65:
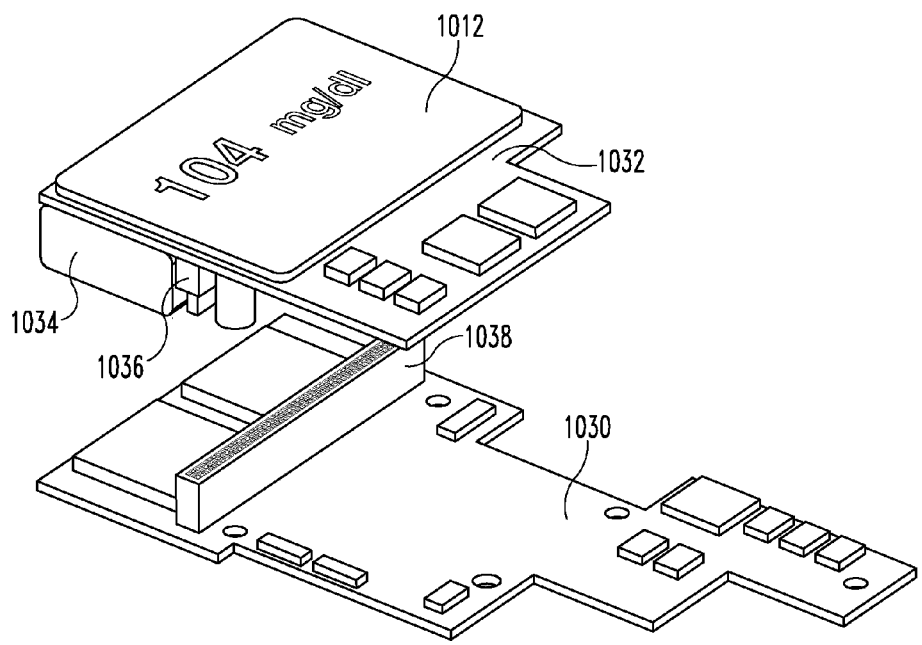
FIG. 65 is a top perspective view of the display, upper printed circuit board, lower printed circuit board, and battery.

The portable meter system 1000 has a lower printed circuit board 1030 and an upper printed circuit board 1032 that are powered by a battery 1034 as illustrated in FIGS. 64 and 65. The upper printed circuit board 1032 is connected to the display 1012. The upper printed circuit board 1032 includes an edge connector 1036. The lower printed circuit board 1030 includes an edge connector socket or slot 1038. Edge connector socket 1038 is typically a female electrical connector for use with a male electrical connector such as edge connector 1036. When assembled, edge connector 1036 mates with edge connector socket 1038 to connect upper printed circuit board 1032 to lower printed circuit board 1030.

The portable meter system 1000 includes a motor 1040 that drives a fourth gear 1042. A priming gear 1044 connects with the fourth gear 1042 and a fifth gear 1046. The placement of the fourth gear 1042, priming gear 1044, and fifth gear 1046 enables the motor 1040 to have at least two functions depending on the rotational direction of the gears 1042, 1044, and 1046. If the fourth gear 1042 has a clockwise rotation by motor 1040, then the lancet frame 130, lancet wheel 122, and test ring 126 will be rotated for the next lancing, sampling, and testing event, as described in more detail below. If the fourth gear 1042 has a counterclockwise rotation by motor 1040, then the spring motor 1050 is primed to drive the crank shaft 1070 and after triggering, cause a lancing, sampling, and testing event, as described in more detail below.

Figure 60:
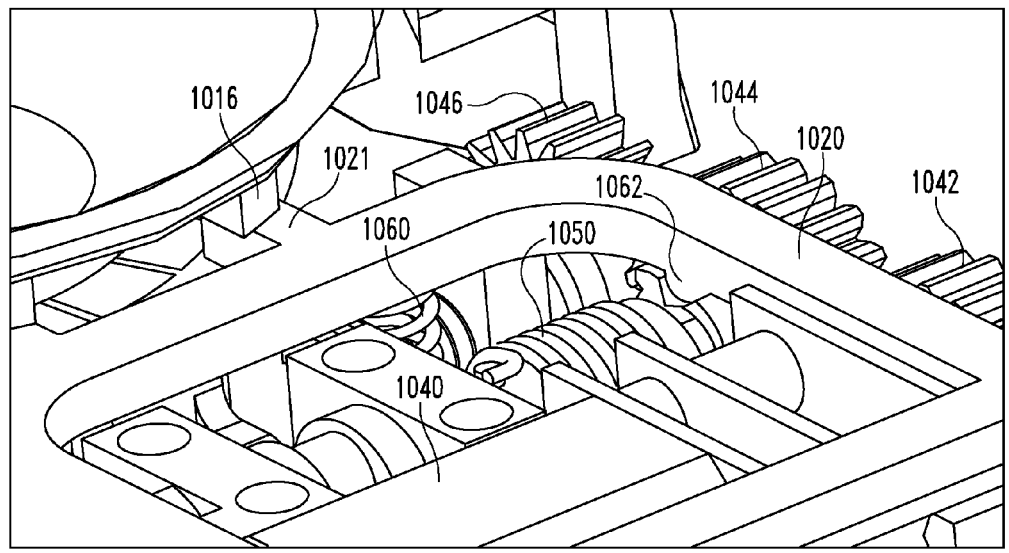
FIG. 60 is a partial top perspective view of the FIG. 59 mechanism.
Figure 61:
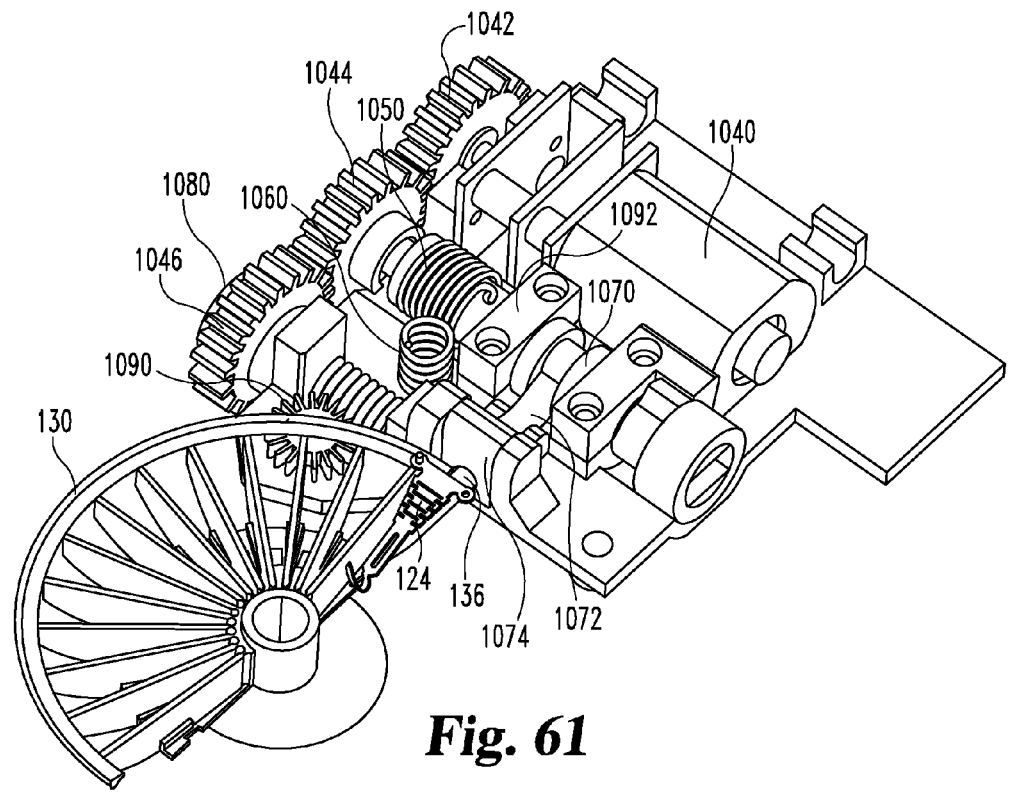
FIG. 61 is a partial top perspective view of the FIG. 60 mechanism with the release arm removed.
Figure 62:
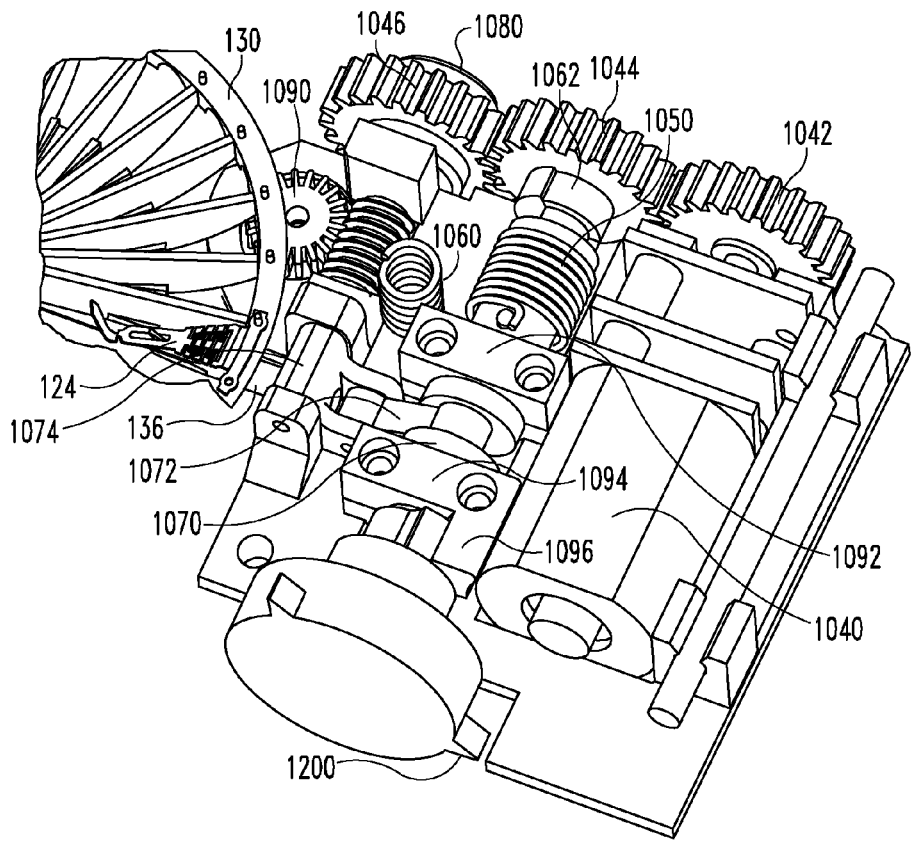
FIG. 62 is a partial top view of the FIG. 61 mechanism.
Figure 66:
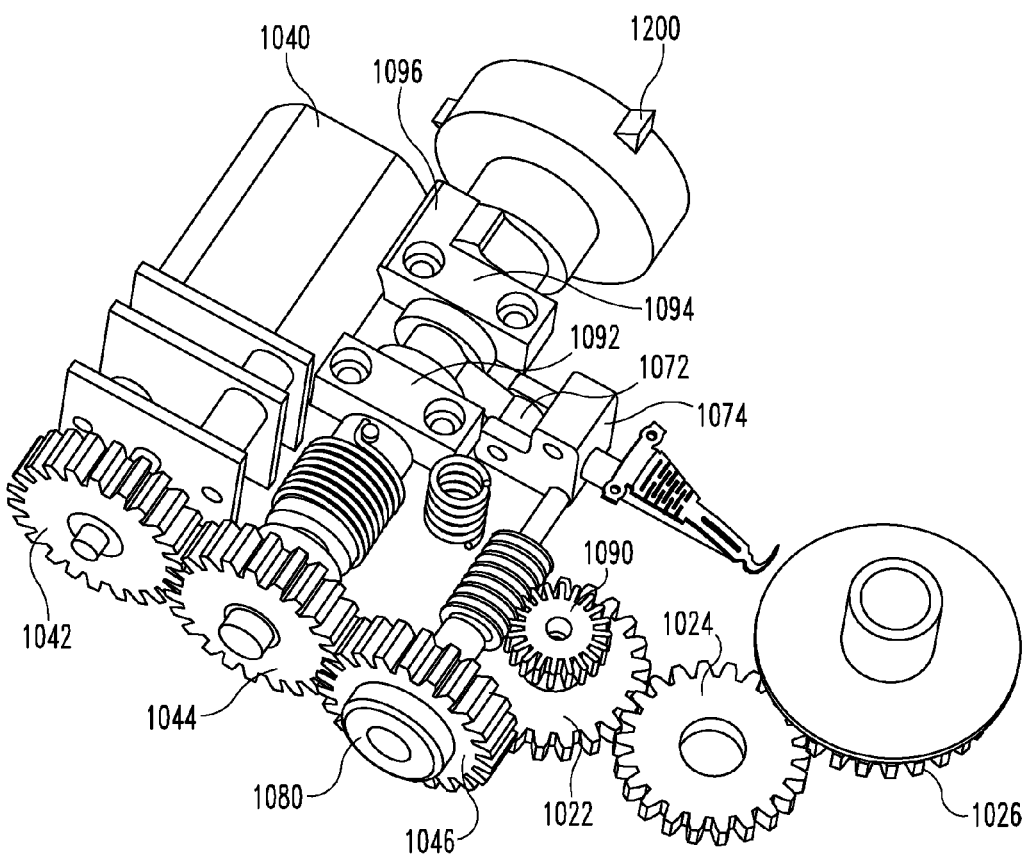
FIG. 66 is a top perspective view of the FIG. 61 mechanism with the frame and lancet frame removed.

As illustrated in FIGS. 60, 61, and 62, the portable meter system 1000 includes a force spring 1060. The portable meter system 1000 also includes a crank shaft 1070 that is connected to a crank arm 1072. The crank shaft 1070 has a dampener stop tab 1200, as illustrated in FIG. 66. The crank arm 1072 is pivotally connected to a tip up link 1074. The tip up link 1074 is connected to driver 136 that engages lancet 124. The portable meter system 1000 includes a one-way clutch 1080 that extends through fifth gear 1046 and a worm drive 1090. The portable meter system 1000 has a first bearing cap 1092 and a second bearing cap 1094. Second bearing cap 1094 has a hard stop 1096.

Figure 63:
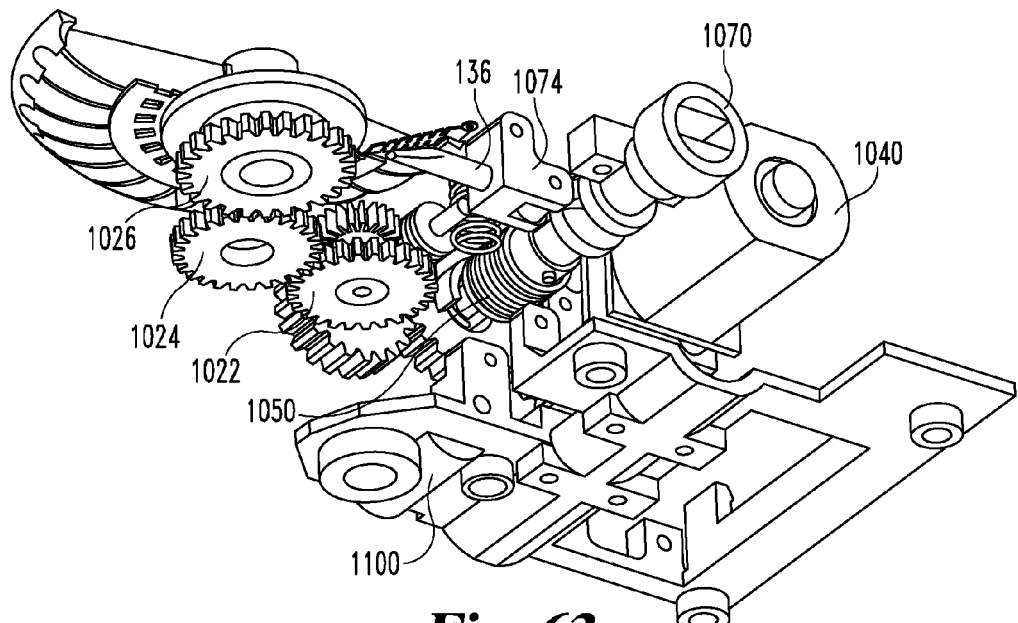
FIG. 63 is a partial exploded bottom view of the FIG. 62 mechanism.

As illustrated in FIG. 63, the portable meter system 1000 includes a frame 1100. Frame 1100 supports motor 1040, crank shaft 1070, tip up link 1074, one-way clutch 1080, and worm drive 1090. In particular, tip up link 1074 is pivotally mounted to frame 1100. Frame 1100 is positioned next to the lower printed circuit board 1030.

Figure 67:
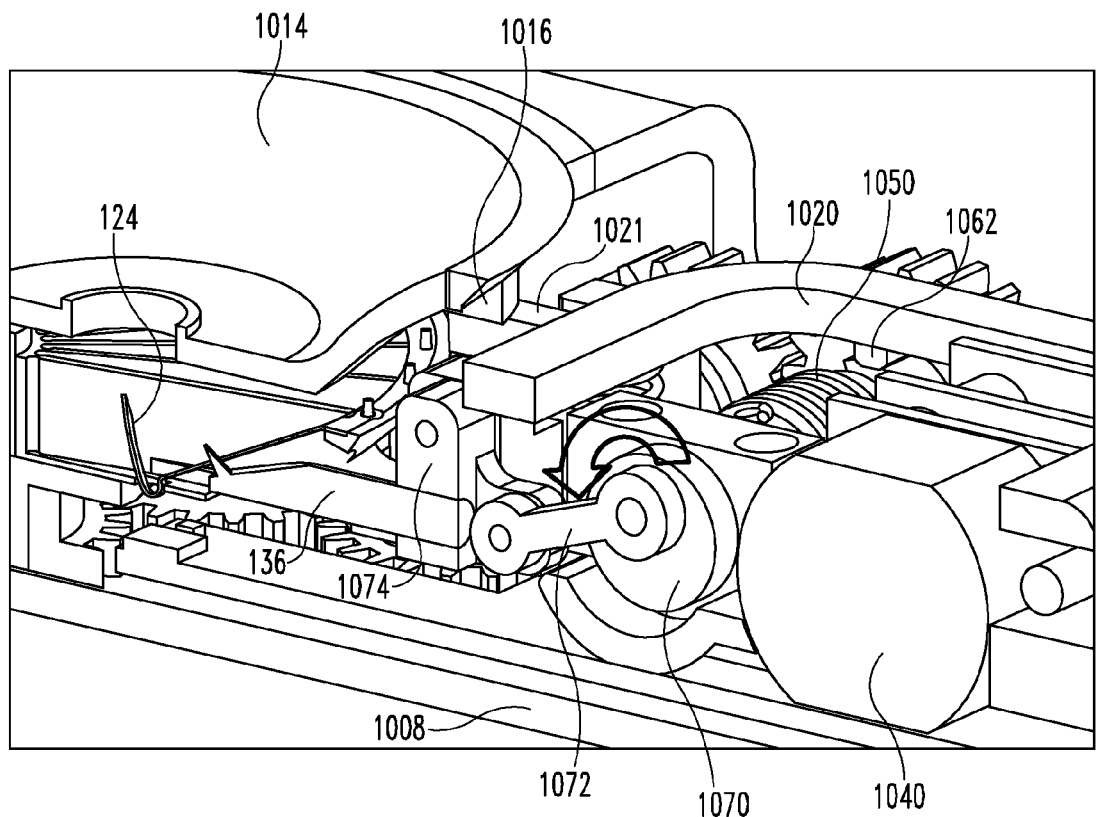
FIG. 67 is a partial top perspective view of the FIG. 59 mechanism.
Figure 68:
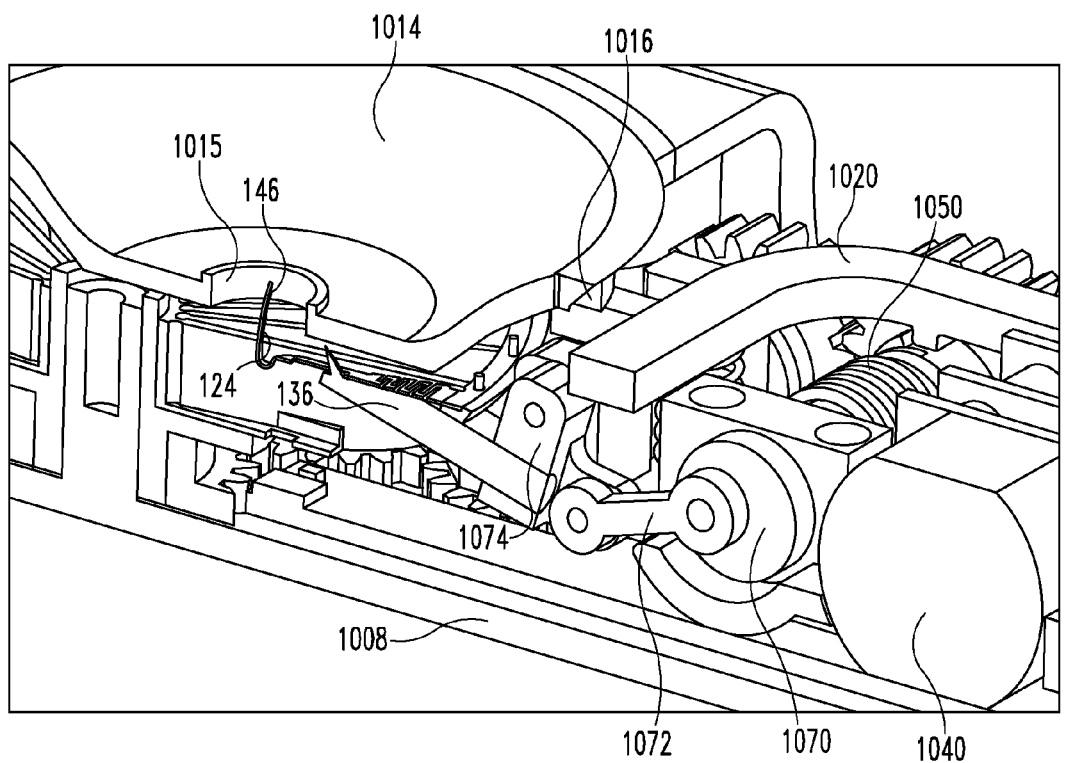
FIG. 68 is a partial top perspective view of the FIG. 59 mechanism.
Figure 69:
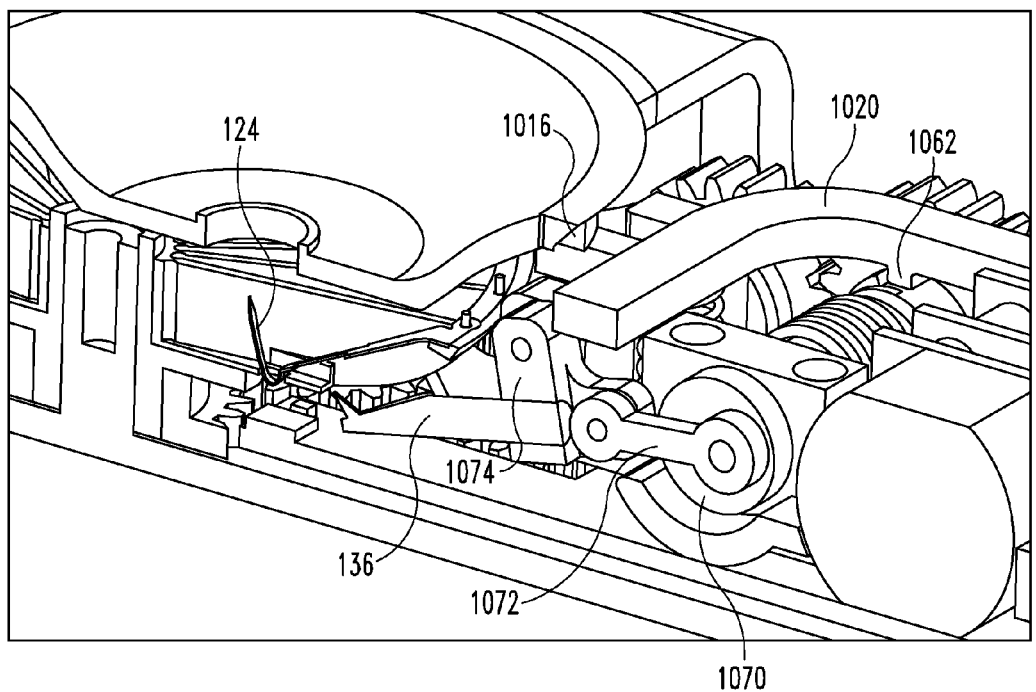
FIG. 69 is a partial top perspective view of the FIG. 59 mechanism.
Figure 70:
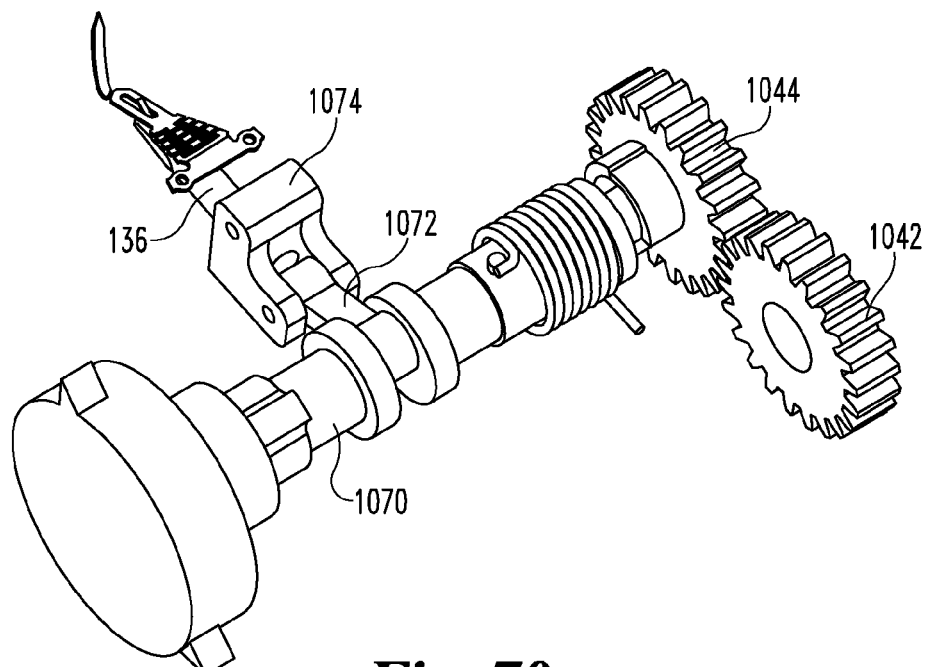
FIG. 70 is a perspective view of crank shaft, crank, tip up link, dampener, spring motor, fourth gear, and priming gear.

FIGS. 67, 68, and 69 illustrate actuation of the lancet 124 by the portable meter system 1000. Crank shaft 1070, crank arm 1072, tip up link 1074, driver 136, and lancet 124 are in an initial position as shown in FIG. 67. In FIG. 67, crank arm 1072 is in a 0 degree position or a pre-incision forming position. A user places a finger against the opening 1015 and presses the pressure cup 1014 towards the base 1008. The pressure cup 1014 is configured to allow movement of the pressure cup 1014 to transfer force from the finger pressure to actuate the lancet 124 as follows. Pressure cup 1014 presses against the release arm 1020 to transfer the force from the pair of trigger contact tabs 1016 to the pair of tabs 1021 to move release arm 1020 towards the base 1008. As release arm 1020 moves, trigger 1062 engages a latch and releases spring motor 1050 to drive the crank shaft 1070 and crank arm 1072.

As shown in FIG. 68, the crank shaft 1070 rotates crank arm 1072 in a counterclockwise direction approximately 90 degrees from the initial position of the crank arm 1072. Crank arm 1072 correspondingly rotates or pivots tip up link 1074 in a clockwise direction. Crank arm 1072 is now at a 90 degree position or an incision forming position. As tip up link 1074 rotates, driver 136 also rotates in a clockwise direction to rotate the lancet tip 146 through the opening 1015 to form an incision in skin and collect a body fluid sample. The lancet tip 146 is lifted into a finger of a user in a few milliseconds. In one embodiment, the lancet tip 146 could be lifted into a finger in about three to five milliseconds. The movement of the crank shaft 1070 results in a "fast-in" position wherein the lancet 124 forms an incision in tissue quickly as compared to the withdrawal of the lancet 124 as described next.

As shown in FIG. 69, the crank shaft 1070 continues to rotate crank arm 1072 in a counterclockwise direction approximately 180 degrees from the incision forming position of the crank arm 1072. Dampener stop tab 1200 engages the frame 1100 to slowly return the lancet 124 to its final position wherein the lancet tip 146 contacts a test section 128. This results in a "slow-out" position wherein the lancet 124 returns to its final position slowly as compared to the lancet forming an incision. In one embodiment, the time required for the lancet tip 146 to form an incision is ten to one hundred times faster than the time required for the lancet tip 146 to return to its final position. Crank arm 1072 is now at a 270 degree position from the initial position of crank arm 1072. At this position, the body fluid sample is transferred from the lancet tip 146 to a corresponding one of the plurality of test sections 128. Tip up link 1074 is rotated in a counterclockwise direction to lower the driver 136 below the lancet frame 130 to clear the lancet frame 130 for rotation to an unused lancet 124 and a subsequent testing event.

The crank shaft 1070 continues to rotate crank arm 1072 in a counterclockwise direction approximately 90 degrees from the body fluid transferring position to the initial position for a subsequent lancing, sampling, and testing event.

A portable meter system 2000 according to one embodiment is illustrated in FIGS. 71, 72, 73, 74, 75, 76, 77, 78, 79, 80, 81, 82, 83, 84, and 85. Common features from portable meter system 2000 and portable meter system 1000 illustrated in FIGS. 54, 55, 56, 57, 58, 59, 60, 61, 62, 63, 64, 65, 66, 67, 68, 69, and 70 will not be discussed for the sake of brevity. Looking at FIGS. 71 and 73, the meter system 2000 includes a housing 2002 that houses the lancet frame 130, lancet wheel 122, and test ring 126. Schematically only lancet frame 130 is shown in the meter system 2000 for clarity although the meter system 2000 will be described with reference to the lancet wheel 122 and test ring 126. Although the portable meter system 2000 will be described with reference to lancet frame 130, lancet wheel 122, and test ring 126, the meter system 2000 can be adapted to the above listed cartridges and/or lancet frames, lancet wheels, and test rings. Meter system 2000 includes an electronic triggering system and a penetration depth control adjustment system whereas meter system 100 does not include these features.

Figure 71:
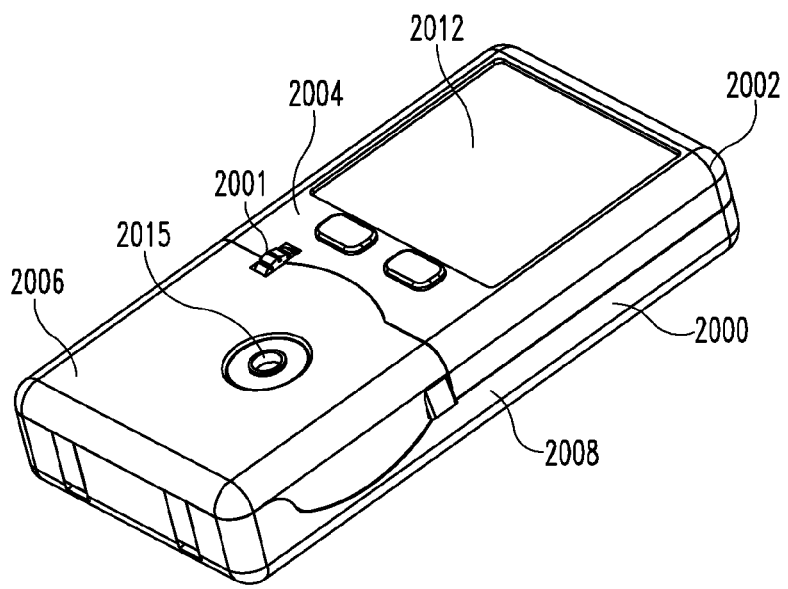
FIG. 71 is a perspective view of a portable meter system according to one embodiment.

The housing 2002 includes a front cover 2004, a door 2006, and a base 2008 as illustrated in FIG. 71. The front cover 2004 has a display 2012 for displaying test results as well as other information. It should be appreciated that the meter system 2000 can include other output devices, like a speaker, for example. The door 2006 includes an opening 2015 positioned over the lancet frame 130, lancet wheel 122, and test ring 126. Upon actuation, lancet tip 146 exits opening 2015 to form an incision in skin. Meter system 2000 does not include a pressure cup in which to trigger a lancing, sampling, and testing event. Instead meter system 2000 includes an electric force sensor (not shown) that senses or detects the presence of a finger or other body part positioned over the opening 2015. After the finger force is detected on the opening 2015, a motor 2040 starts again and fires the lancet 124 to complete a lancing, sampling, and testing event, as described in more detail below.

Figure 72:
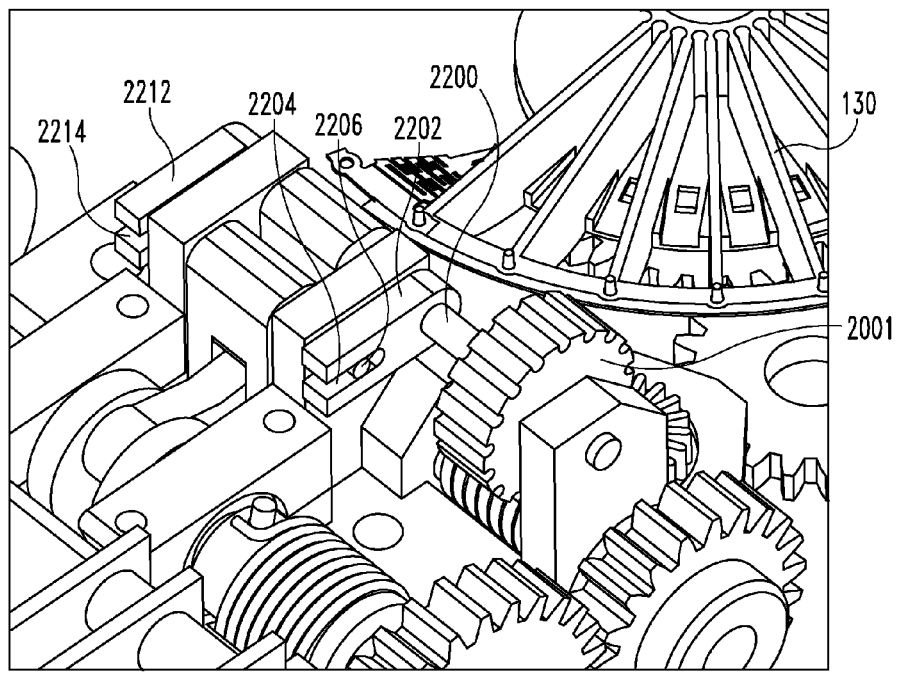
FIG. 72 is a partial top perspective view of the FIG. 71 mechanism with the top and bottom covers removed in an initial position.
Figure 73:
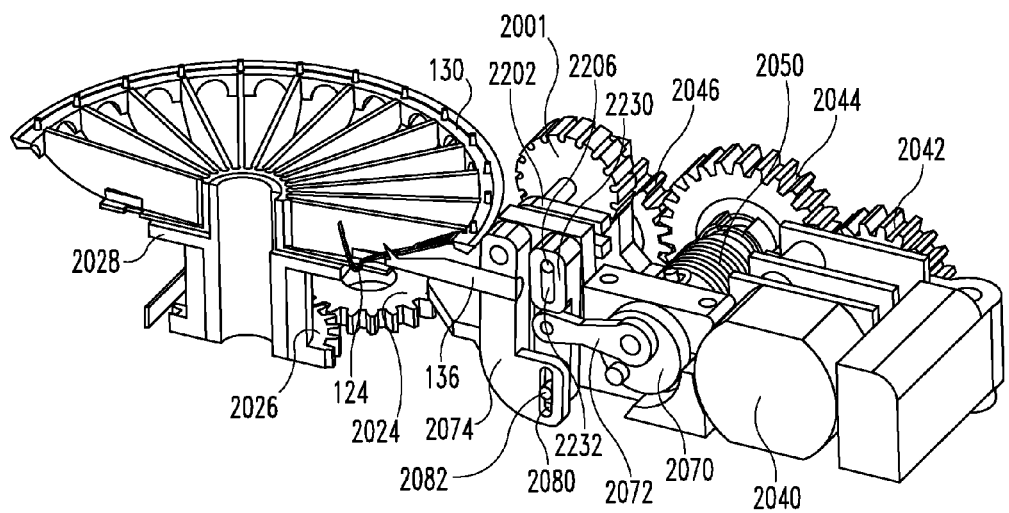
FIG. 73 is a partial top perspective view of the FIG. 71 mechanism with the top and bottom covers removed in an initial position of a shallow penetration depth setting.

Portable meter system 2000 includes a wheel 2001 for adjusting the penetration depth of each of the plurality of lancets 124 for a lancing event. Wheel 2001 is rotated to adjust the penetration depth of the active one of lancets 124 to either a shallow depth setting or a deep depth setting as described in more detail below. Initially, wheel 2001 is mounted on a first end of a shaft 2200 such that one of the lancets 124 is in a shallow depth setting as shown in FIG. 73. Mounted along a midpoint of shaft 2200 is a first lever 2202 that defines a first slot 2204 as illustrated in FIG. 72. Mounted on an opposite end of shaft 2200 is a second lever 2212 that is similar to first lever 2202. Second lever 2212 defines a second slot 2214. A first end of a first pin 2206 is configured to fit in first slot 2204 and a second end of pin 2206 is configured to fit in the second slot 2214. The first pin 2206 rides along or slides in the first slot 2204 and the second slot 2214 as the first lever 2202 and the second lever 2212 are rotated corresponding to rotation of wheel 2001 from a shallow depth setting to a deep depth setting. The middle portion of first pin 2206 is configured to fit through a first opening 2232 defined in an intermediate arm 2230. The first lever 2202 and the second lever 2212 work together or as a pair to control the position of first pin 2206 which sets the depth setting to either "shallow" or "deep" penetration.

Figure 74:
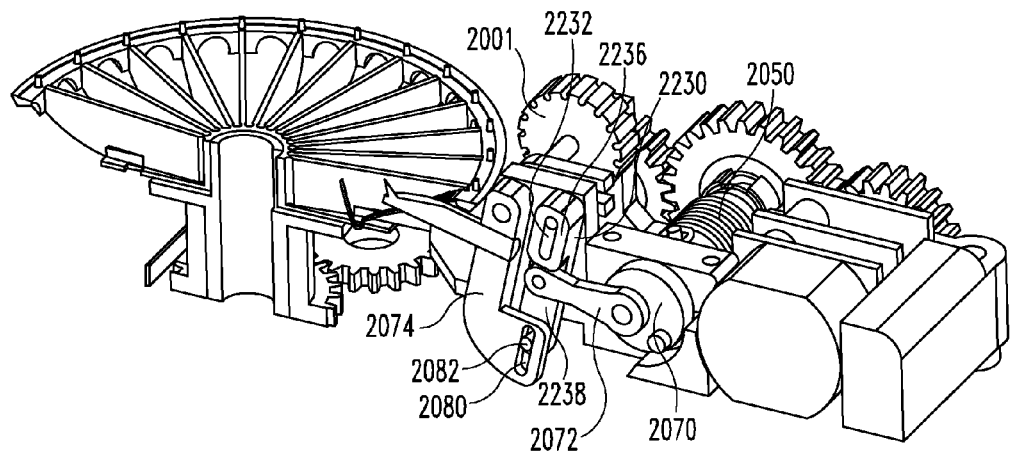
FIG. 74 is a partial top perspective view of the FIG. 71 mechanism with the top and bottom covers removed in a fully extended position of a shallow penetration depth setting.

As shown in FIG. 74, intermediate arm 2230 includes an upper half 2236 that defines the first opening 2232. Intermediate arm 2230 also includes a lower half 2238 that includes a second pin 2082 that fits in and slides in a slot 2080 of tip up link 2074 as described below.

A tip up link 2074 is mounted on the shaft 2200. Tip up link 2074 is attached to the driver 136 that engages each of the lancets 124. Tip up link 2074 defines a slot 2080 that is configured to receive the second pin 2082 of the intermediate arm 2230.

Figure 75:
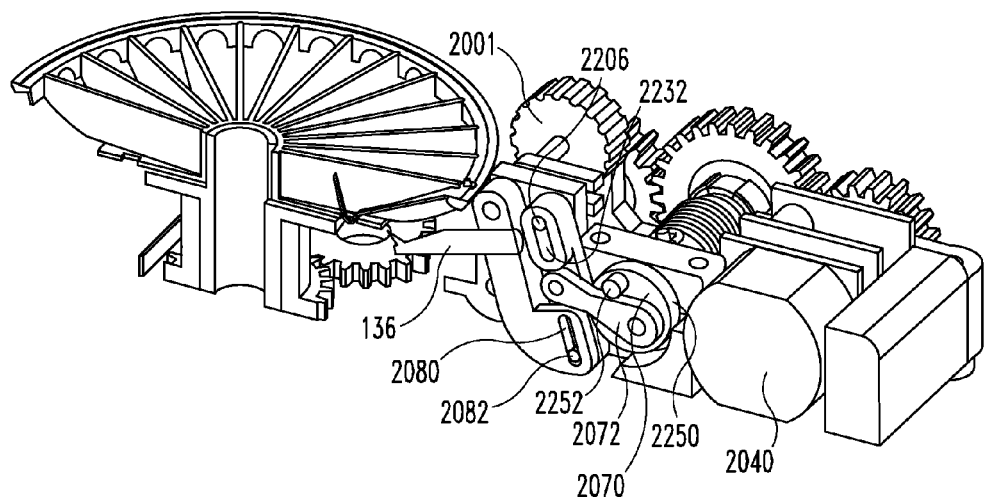
FIG. 75 is a partial top perspective view of the FIG. 71 mechanism with the top and bottom covers removed in a final position of a shallow penetration depth setting.
Figure 78:
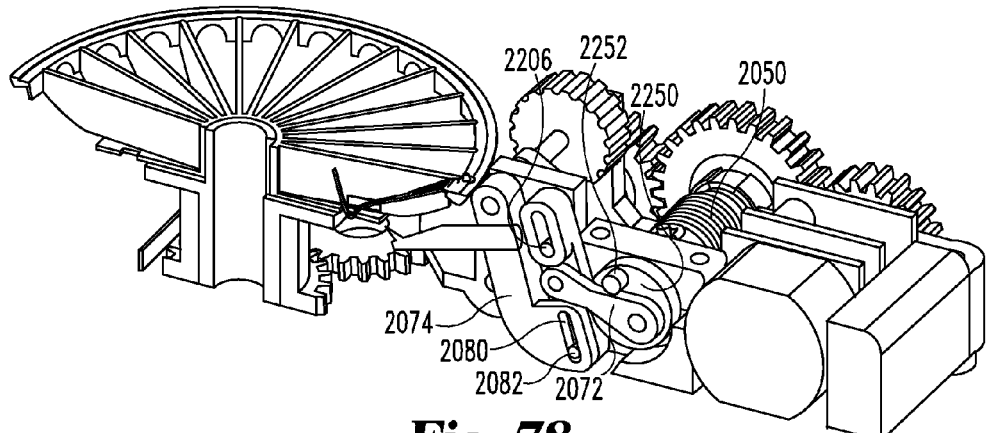
FIG. 78 is a partial top perspective view of the FIG. 71 mechanism with the top and bottom covers removed in a final position of a deep penetration depth setting.
Figure 79:
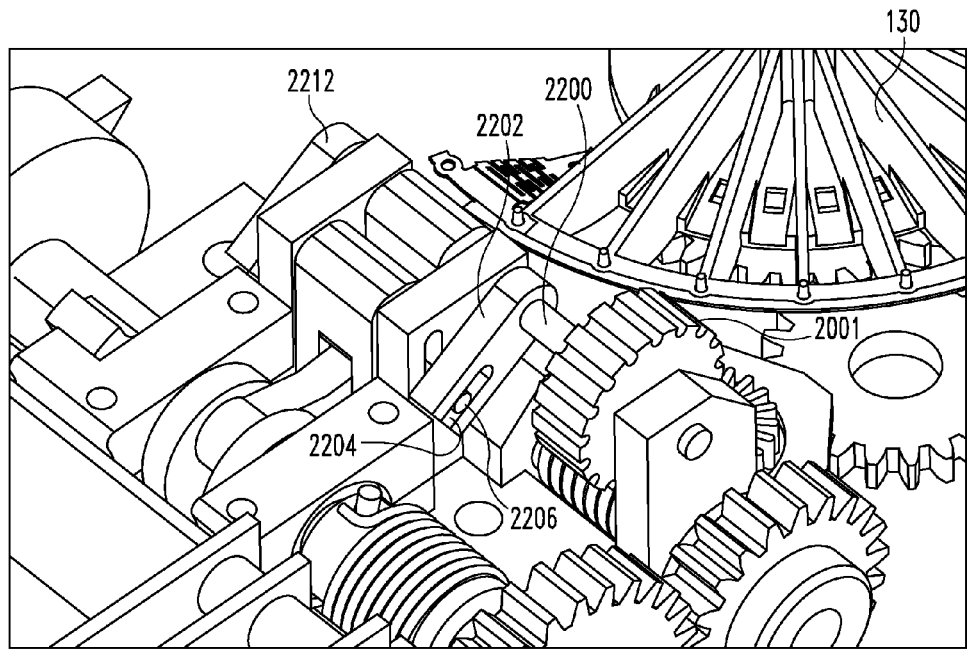
FIG. 79 is a partial top perspective view of the FIG. 76 mechanism.
Figure 80:
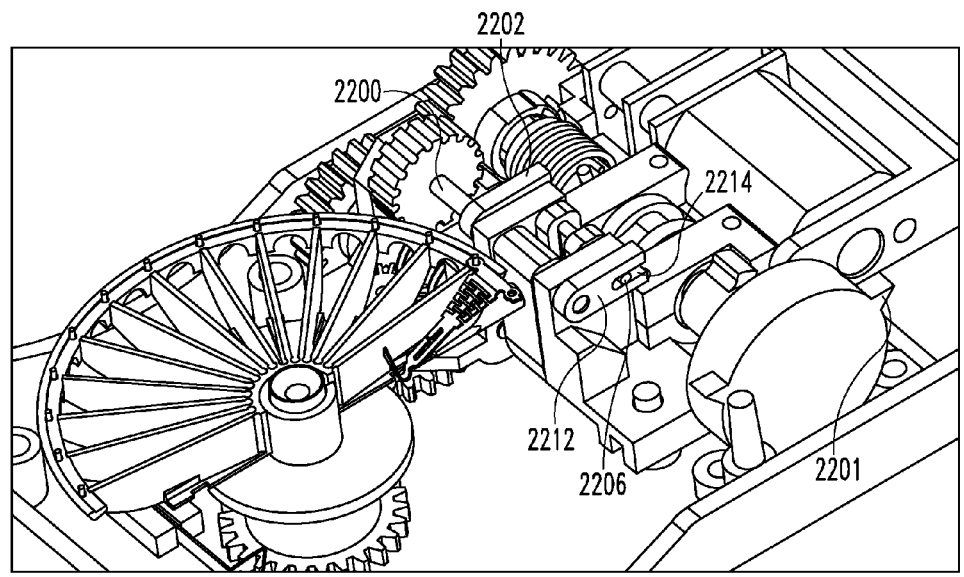
FIG. 80 is a partial top perspective view of the FIG. 73 mechanism with the bottom cover.
Figure 81:
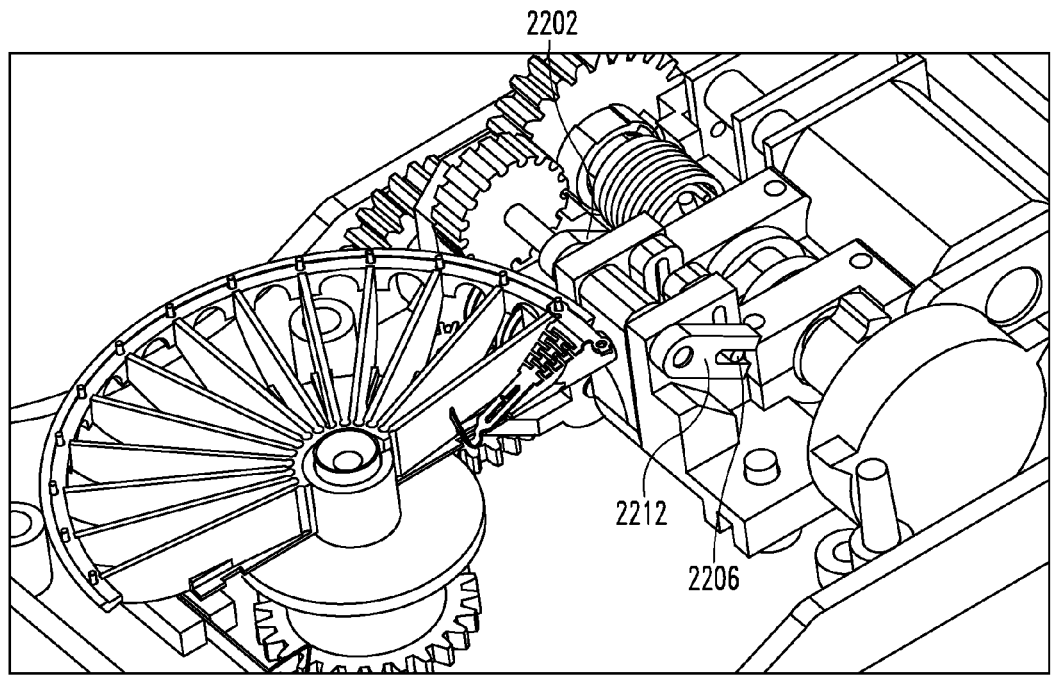
FIG. 81 is a partial top perspective view of the FIG. 76 mechanism with the bottom cover.
Figure 82:
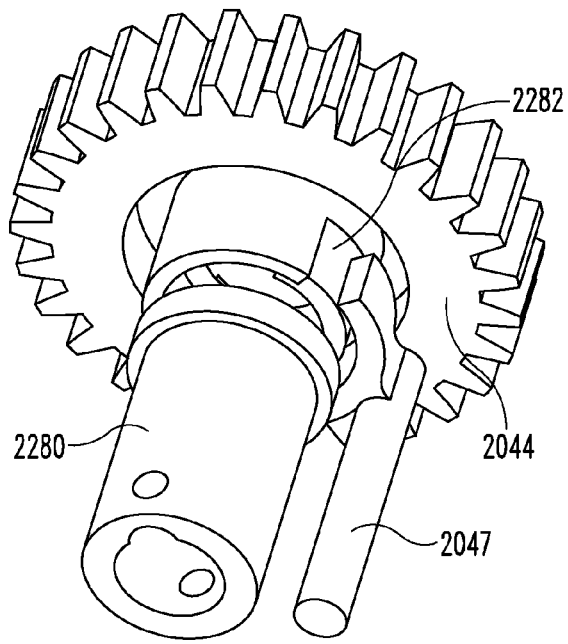
FIG. 82 is a perspective view of a trigger system.
Figure 83:
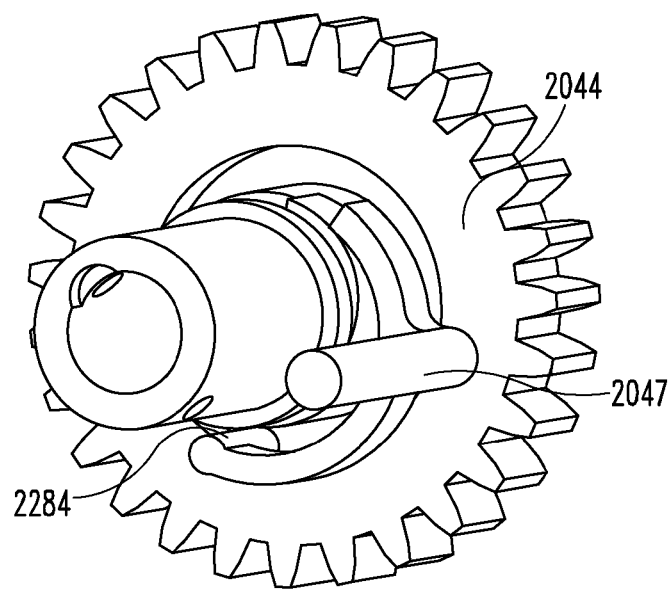
FIG. 83 is a perspective view of the FIG. 82 mechanism.
Figure 84:
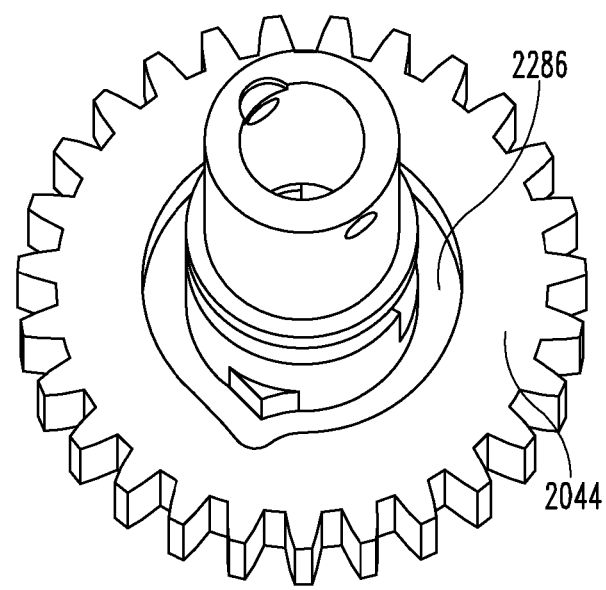
FIG. 84 is a perspective view of the FIG. 82 mechanism.
Figure 85:
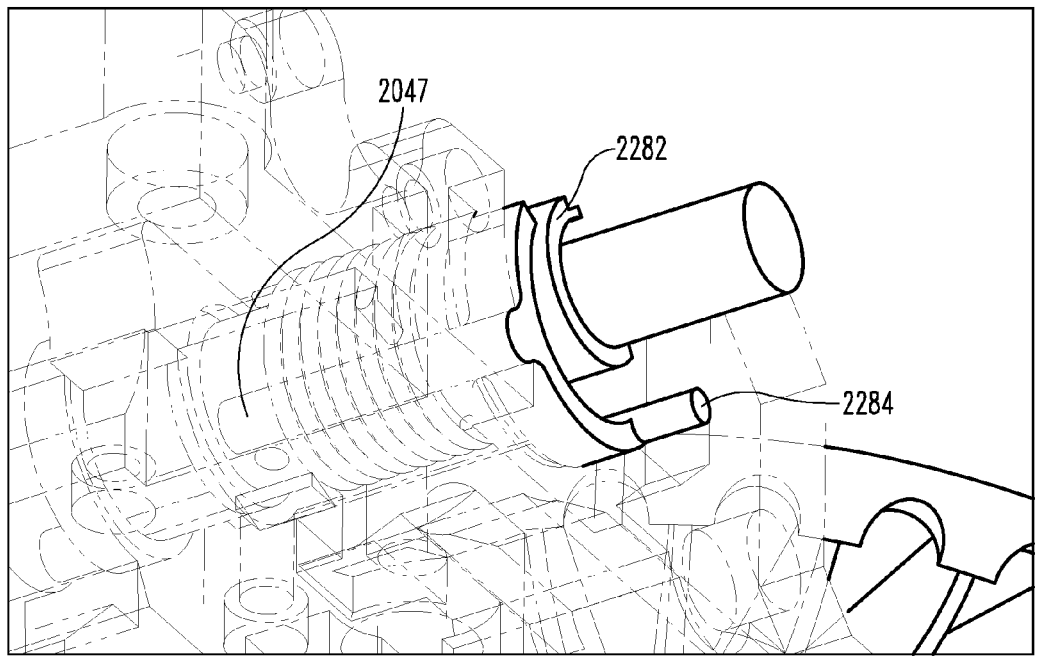
FIG. 85 is a perspective view of the FIG. 82 mechanism.

Meter system 2000 also has a different actuation system than portable meter system 1000. Meter system 2000 includes a crank shaft 2070 that is similar to crank shaft 2070. Crank shaft 2070 includes a disk 2250 with a stopper 2252 that is configured to contact a crank arm 2072 in the final position of a used lancet as illustrated in FIGS. 75 and 78. The crank arm 2072 is similar to the crank arm 1072 however a first end of crank arm 2072 is rotatably mounted on the disk 2250. A second end of the crank arm 2072 is pivotably attached to the intermediate arm 2230. The crank shaft 2070 has a dampener stop tab 2201, as illustrated in FIG. 80. The second pin 2082 of intermediate arm 2230 slides in slot 2080 of the tip up link 2074 to cause the tip up link 2074 and corresponding driver 136 to rotate. The interaction of crank shaft 2070, crank arm 2072, intermediate arm 2230, and tip up link 2074 will be described in more detail below.

Meter system 2000 has a priming gear 2044 that connects with a fourth gear 2042 and a fifth gear 2046 as shown in FIG. 73. Fourth gear 2042, priming gear 2044, and fifth gear 2046 are similar to fourth gear 1042, priming gear 1044, and fifth gear 1046 of meter system 1000.

Meter system 2000 includes an electronic triggering system as shown in FIGS. 82, 83, 84, and 85. A trigger cam 2280 having a catch 2282 is mounted to priming gear 2044. A catch-release pivot shaft 2047 rides inside the catch 2282. The catch-release pivot shaft 2047 has a guide or follower pin 2284. The follower pin 2284 travels along a cam groove 2286 in gear 2044.

The portable meter system 2000 includes a motor 2040 that drives the fourth gear 2042. Similar to motor 1040, motor 2040 has at least two functions depending on the rotational direction of the gears 2042, 2044, and 2046. When motor 2040 is turned "on", motor 2040 winds ¾ of a revolution and then motor 2040 stops. When the finger force is detected on the opening 2015, the motor 2040 starts again and fires the lancet 124.

Figure 76:
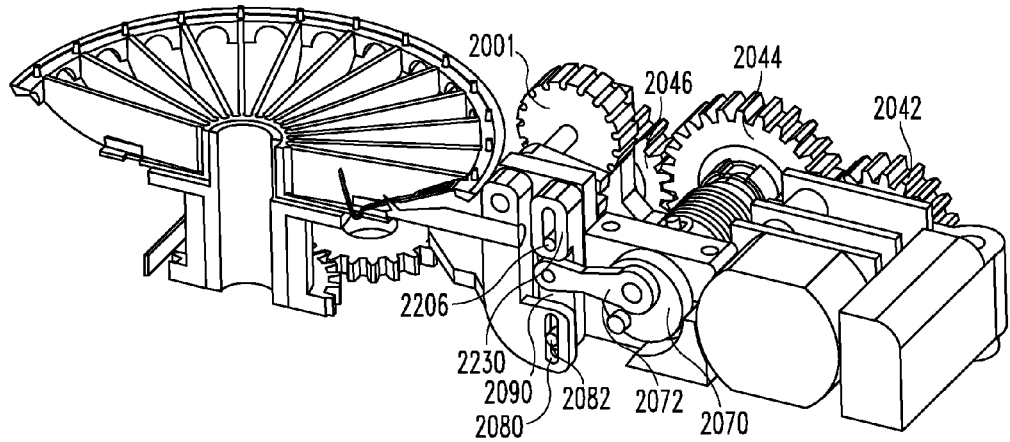
FIG. 76 is a partial top perspective view of the FIG. 71 mechanism with the top and bottom covers removed in an initial position of a deep penetration depth setting.

Meter system 2000 can also be adjusted for either a shallow penetration depth setting or a deep penetration depth setting of a lancet 124 as described next. As shown in FIG. 73, the pin 2206 positioned in the first slot 2204, the first opening 2232, and the second slot 2214 (not illustrated) is in an initial position of a shallow penetration depth setting. If a deep penetration depth of an active one of the lancets 124 is desired as shown in FIG. 76, then wheel 2001 is rotated which causes the attached shaft 2200 to rotate and the first lever 2202 and second lever 2212 (not illustrated) to pivot which in turn causes the pin 2206 in the first slot 2204, the first opening 2232, and the second slot 2214 (not illustrated) to move down or towards the crank arm 2072. After the wheel 2001 is rotated to a deep penetration depth setting, the pin 2206 is positioned to cause the tip up link 2074 and driver 136 to rotate a greater distance and thereby force the active one of the lancets 124 to move a greater distance and form a deeper incision.

FIGS. 73, 74, and 75 illustrate actuation of the active one of lancets 124 by the portable meter system 2000 with the meter system 2000 in a shallow penetration depth setting with first pin 2206 positioned at the top of first opening 2232 of intermediate arm 2230. Crank shaft 2070, crank arm 2072, intermediate arm 2230, tip up link 2074, driver 136, and lancet 124 are in an initial position as shown in FIG. 73. In FIG. 73, crank arm 2072 is in a 0 degree position or a pre-incision forming position. A user turns "on" motor 2040 to cause motor 2040 to wind three-fourths of a revolution and then stop. A user places a finger against the opening 2015. The electric sensor senses the finger force and the motor 2040 starts again. The spring motor 2050 is wound one revolution from the interaction of the motor 2040, fourth gear 2042, and priming gear 2044. Catch-release pivot shaft 2047 is then activated to release spring motor 2050 to drive the crank shaft 2070 and crank arm 2072.

As shown in FIG. 74, the crank shaft 2070 rotates crank arm 2072 in a counterclockwise direction approximately 90 degrees from the initial position of the crank arm 2072. Crank arm 2072 correspondingly rotates or pivots intermediate arm 2230 and tip up link 2074 in a clockwise direction. The second pin 2082 of intermediate arm 2230 is in the top position of slot 2080 of the tip up link 2074 to cause the tip up link 2074 and corresponding driver 136 to rotate the driver 136 towards the opening 2015. Crank arm 2072 is now at a 90 degree position or an incision forming position. As tip up link 2074 rotates, driver 136 also rotates in a clockwise direction to rotate the lancet tip 146 through the opening 2015 to form an incision in skin and collect a body fluid sample. The lancet tip 146 is lifted into a finger of a user in a few milliseconds. In one embodiment, the lancet tip 146 could be lifted into a finger in about three to five milliseconds. The movement of the crank shaft 2070 results in a "fast-in" position similar to the crank shaft 1070 of meter system 1000.

As shown in FIG. 75, the crank shaft 2070 continues to rotate crank arm 2072 in a counterclockwise direction approximately 180 degrees from the incision forming position of the crank arm 2072. Stopper 2252 contacts the crank arm 2072 and dampener stop tab 2200 engages a frame 2100 (not illustrated) to slowly return the lancet 124 to its final position wherein the lancet 124 contacts a test section 124. This results in a "slow-out" position similar to meter system 1000. In one embodiment, the time required for the lancet tip 146 to form an incision is twice as fast as the time required for the lancet tip 146 to return to its final position. Crank arm 2072 is now at a 270 degree position from the initial position of crank arm 2072. At this final position, the body fluid sample is transferred from the lancet tip 146 to a corresponding one of the plurality of test sections 128. As shown in FIG. 75, the second pin 2082 of intermediate arm 2230 is in the bottom of slot 2080 of the tip up link 2074 to cause the tip up link 2074 and corresponding driver 136 to rotate the driver 136 below the lancet frame 130 such that the driver 136 has cleared the lancet frame 130 for rotation of the lancet frame 130 to an unused lancet 124 and a subsequent testing event.

The crank shaft 2070 reverses its direction to rotate crank arm 2072 in a clockwise direction approximately 270 degrees from the body fluid transferring position to the initial position for a subsequent lancing, sampling, and testing event.

Figure 77:
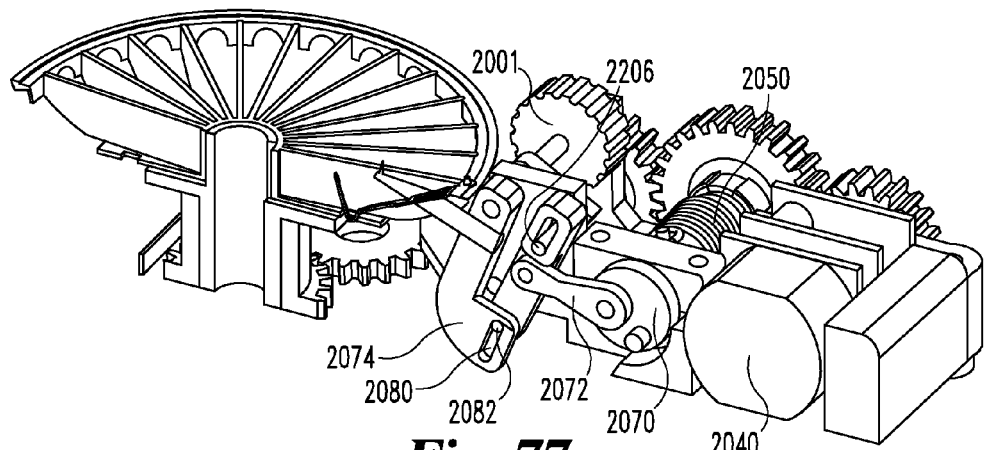
FIG. 77 is a partial top perspective view of the FIG. 71 mechanism with the top and bottom covers removed in a fully extended position of a deep penetration depth setting.

FIGS. 76, 77, and 78 illustrate actuation of the lancet 124 by the portable meter system 2000 with the meter system 2000 in a deep penetration depth setting. The wheel 2001 is rotated to lower the first pin 2206 to the bottom of first opening 2232 of intermediate arm 2230 and force the tip up link 2074 and driver 136 to rotate further than the shallow depth setting to cause a deeper penetration depth of the active one of the lancets 124. Crank shaft 2070, crank arm 2072, intermediate arm 2230, tip up link 2074, driver 136, and lancet 124 operate as described previously with respect to FIGS. 73, 74, and 75.

Another embodiment concerns keeping the sampling member off the test element in a common space until use, where only the sampling member is actuated. Accordingly with regard to a device it is proposed that the test member is fixed in a retaining chamber of the container, and the sampling member is configured in the same retaining chamber such that it is separated at a distance from the test member in an initial state and is in contact with the test member to transfer body fluid in a transfer state after the skin-piercing. In this manner it is possible to avoid a contamination of the sampling member especially with loose chemistry particles of the test element before the skin contact. Further, the fixed connection of the test member in the container facilitates manufacture of the disposable and allows a simplified sample transfer, while ensuring a safe disposal of the used and potentially bio-hazardous material. Accordingly, the sampling member is actuated to carry out a piercing movement outwards and backwards into the container, and the test member is arranged stationary inside the container.

One embodiment stipulates that the sampling member is separated from the test member by means of a spacer which can be put out of function during the skin-piercing. In order to provide a free space between the sampling member and the test member in the initial state, the spacer extends over a distance in direction of a piercing movement of the sampling member.

Advantageously, the spacer is removable by an actuator configured to actuate piercing movement of the sampling member. In this respect it is beneficial if the spacer is formed, preferably with a predetermined breaking point, at a wall of the container defining the retaining chamber, and is cut off the wall to achieve the transfer phase. Alternatively, it is possible that the spacer is connected to the sampling member, and a stopper of the container is removable such the spacer is inoperable in the transfer state.

Another improvement is achieved in that the sampling member is urged against the test member by means of a resilient element, thus ensuring an automatic sample transfer. In this configuration, the sampling member is deflected against a restoring force of the resilient element during the skin-piercing. This can be realized by a sampling member that has a flexible bending link forming the resilient element. In addition it is advantageous when the sampling member is formed as a hooked needle, and a spring-arm of the hooked needle is pre-tensioned against the test member.

For the application it is also advantageous the sampling member has a tip to pierce the skin and a capillary structure to uptake body fluid, wherein the capillary structure is in fluidic connection with the test element during the transfer phase. A preferred embodiment provides that the sampling member comprises a pointed piercing arm, and a laterally open channel is extending along the piercing arm preferably having a bent section that can be contacted with the test member.

In order to precisely define the actuation, the sampling member may comprise an engagement slot to receive an actuator rod for driving a piercing movement.

For the application it is also advantageous when the test member is formed as a reagent pad having a reactive layer which is sensitive to an analyte in the body fluid, and the flat-material pad is attached to a wall of the container defining the retaining chamber. In this configuration it is possible that the test member is configured to be mounted in the container as a unit separate from the sampling member.

Another improvement is achieved in that the container is sealed against the environment by a sealing foil, and at least a piercing part of the sampling member is penetrated through the sealing foil to allow the skin-piercing. The container can include a wall structure which defines the retaining chamber and comprises a desiccant material to keep the test chemistry dry.

A further advantage in usability is achieved when the container is formed as a magazine to contain a plurality of sampling members and test members preferably arranged in pairs in respective retaining chambers. To achieve a compact design, it is advantageous when the container comprises a disk-like configuration and contains a plurality of sampling members formed as a lancet wheel, and when the sampling members are actuated through a side face of the disk.

It is advantageous for a mass production when the lancet wheel is formed in one piece preferably by etching or cutting a metallic sheet material. It is further beneficial when the container includes a hub to engage a rotary drive for successive rotary positioning of the sampling members with respect to a sampling port of the apparatus constructed to receive the body part.

One embodiment also concerns a process for analyzing body fluid especially for blood sugar tests in which a container is inserted into a measuring apparatus, a sampling member provided in the container is actuated to pierce skin of a body part and sample body fluid, and body fluid obtained by the skin-piercing is transferred to a test member, wherein the test member is stationarily maintained in a retaining chamber of the container, and the sampling member is separately held at a distance from the test member in an initial state and is brought in contact with the test member to transfer body fluid in a transfer state after the skin-piercing.

Figure 86:
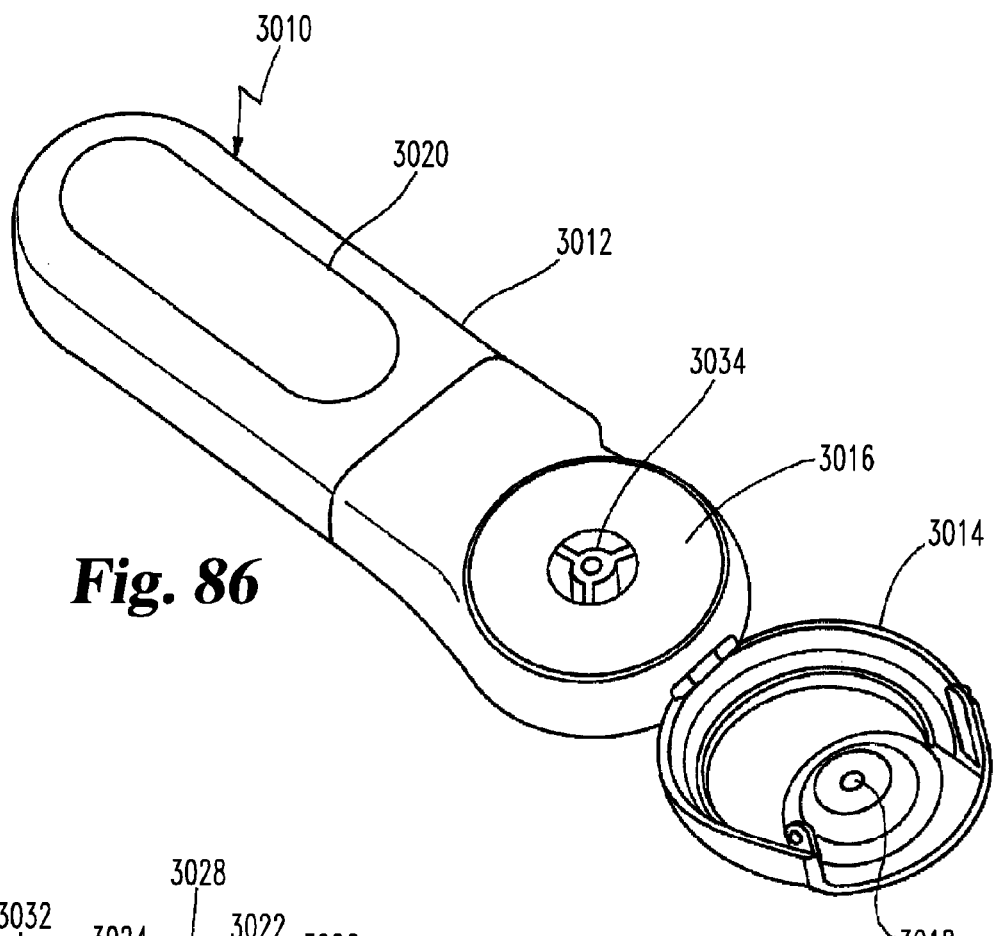
FIG. 86 is a top perspective view of a hand held measuring apparatus for blood glucose tests with an inserted disk-like cartridge.

The apparatus 3010 shown in FIG. 86 allows self-withdrawal of a blood sample by a user for analytical purposes and in particular for blood sugar monitoring. It comprises a housing 3012 with a lid 3014 to allow the change of a disposable test container or cartridge 3016. In the closed state, a body part and in particular a fingertip can be pressed against a port 3018 of the lid 3014 in order to take a blood sample by skin-piercing. The apparatus 3010 further comprises drive and processing units for an automatic measurement operation (not shown). The measurement result can be indicated on a display 3020.

Figure 87:
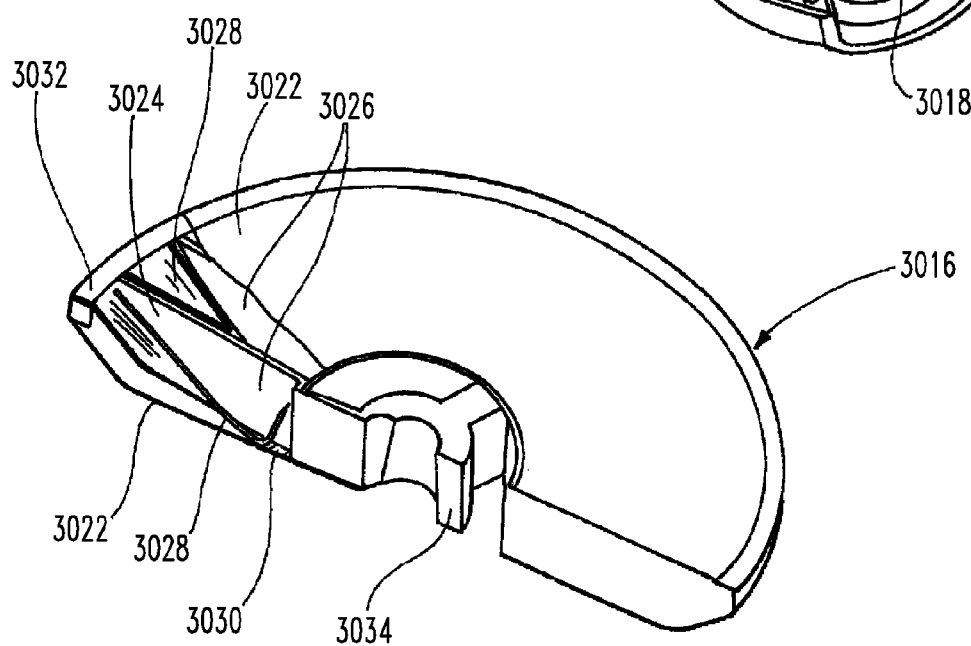
FIG. 87 is a cross-sectional view of the FIG. 86 cartridge with a portion of a sealing foil removed.

As shown in FIG. 87, the cartridge 3016 comprises a disk-like configuration where the side faces are sealed against the environment by foils 3022. The inner space between the foils is divided in sectors by a wall structure 3024. Thereby, a magazine with a plurality of retaining chambers 3026 is defined to accommodate in each chamber a sampling member 3028 and a test member 3030 in pair-wise configuration. The wall structure 3024 can be formed as a single frame by injection molding with a desiccant material co-molded to keep the chambers 3026 free from moisture. It is further conceivable to photo-etch or cut and then pre-form the plurality of sampling members 3028 as a one piece lancet wheel 3032 that can be inserted into the frame 3026. In order to successively position the sampling members 3028 with respect to the port 3018, the frame 3026 includes a hub 3034 for engaging a rotary drive of the apparatus 3010.

Figure 88:
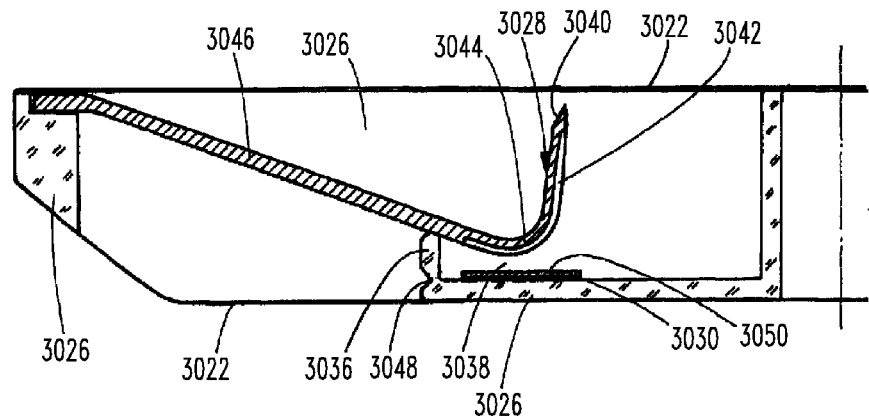
FIG. 88 is a cross-sectional view of the FIG. 86 mechanism.

FIG. 88 shows an initial configuration of a retaining chamber 3026 with the sampling member 3028 being held at a distance with respect to the test member 3030 by means of a spacer 3036. Due to the free space 3038 kept by the spacer 3036, the sampling member 3028 is held off the chemistry film of the test member 3030 until the test is performed.

The sampling member 3028 is formed as a hooked needle, which is accessible for actuation and allows piercing by break-through of the foils 3022. For collecting a small amount of blood from a body part, the sampling member 3028 comprises a pointed tip 3040 and a capillary channel 3042. The channel 3042 is laterally open along its length and extends into a curved section 3044 facing the test member 3030. The sampling member 3028 is linked to the periphery of the frame 3026 via a flexible spring-arm 3046. The spring-arm 3046 is under pretension, such that the section 3044 including the proximal part of the channel 3042 is urged against the removable spacer 3036 and the test member 3030, respectively.

In order to allow a blood transfer from the channel 3042 onto the test member 3030, the spacer 3036 can be removed during the skin-piercing procedure. This is facilitated by means of a breaking point 3048 at the basis of the spacer 3036. Alternatively, it is possible that the spacer 3036 is connected to the sampling member and abuts a removable counterpart, e.g. the sealing foil 3022.

The test member 3030 is formed as a reagent pad having a reactive layer 3050. The reagent pad can be mounted as a unitary ring which is fixed to the bottom of the frame 3026. The reactive layer 3050 comprises a dried enzyme chemistry which is sensitive to blood glucose, such that a colour change occurs which can be optically detected through the transparent frame 3026. The detection of blood glucose in particular by means of contact-free optical methods is known in the prior art and is therefore not elucidated in more detail here.

Figure 89:
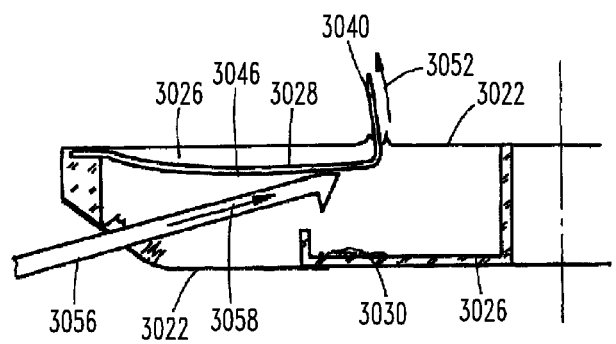
FIG. 89 is a view of the FIG. 88 mechanism with the sampling member in a fully actuated position.
Figure 90:
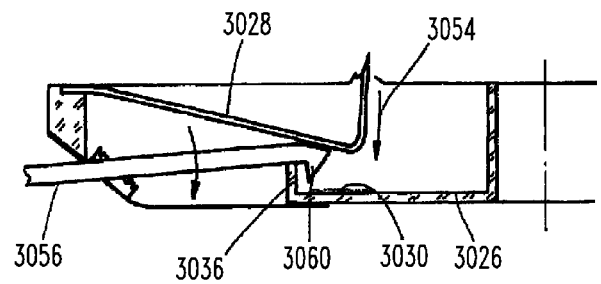
FIG. 90 is a view of the FIG. 88 mechanism with the sampling member in a partially retracted position.
Figure 91:
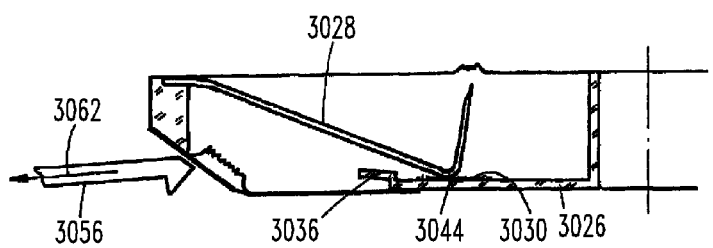
FIG. 91 is a view of the FIG. 88 mechanism with the sampling member in a fully retracted position and a transfer initiating position.

FIGS. 89, 90, and 91 illustrate the sampling and transfer procedure, where the sampling member 3028 is actuated to carry out a piercing movement outwards and backwards (arrows 3052, 3054) into the respective retaining chamber 3026 of the cartridge 3016, while the test member is kept stationary.

In the forward movement 3052, the sampling member 3028 is deflected against the restoring force of the spring-arm 3046 by means of an actuator rod 3056. The rod 3056 is driven in direction of arrow 3058 by a drive unit of the apparatus, thereby penetrating the bottom foil 3022 and sliding along the spring-arm 3046. It is also conceivable that the rod 3056 is provided with an engaging piece for a form-locking engagement with the sampling member (not shown). While the actuator rod 3056 is accessing the spring-arm 3046, the needle tip 3040 is breaking through the upper foil 3022 and pierces the skin of the fingertip applied on the port 3018. During the skin-piercing, blood and/or interstitial liquid is received in the channel 3042 preferably by capillary action.

During the following resilient retraction 3054 of the sampling member, the actuator rod 3056 engages the spacer 3036 with a hook piece 3060 (FIG. 90). Subsequently, the rod 3056 is pulled back in direction of arrow 3062, whereby the spacer 3036 is torn off the frame 3026 (FIG. 91). This allows contact of the curved section 3044 of the sampling member 3028 with the test element 3030, thereby initiating a transfer phase in which the sampled liquid is automatically transferred to the test element for an immediate analysis.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A disposable device for analyzing body fluid, comprising:
    a container which can be inserted into a measuring apparatus, the container having a disk-like configuration and containing a plurality of sampling members formed as a lancet wheel, each of the sampling members having a proximal body portion and a distal skin piercing tip extending at an angle from the proximal body portion to form a contact portion between the proximal body portion and the distal skin piercing tip, the proximal body portion attached to a rim of the lancet wheel, the distal skin piercing tip configured to pierce skin of a body part, and the contact portion disposed at a bend between the proximal body portion and the distal skin piercing tip configured for transfer of a body fluid sample;
    a plurality of test members corresponding to the plurality of sampling members for receiving body fluid obtained by the skin-piercing, wherein the plurality of test members are fixed in a plurality of retaining chambers of the container; and
    wherein each of the sampling members is configured to move from an initial state wherein the sampling member does not contact the test member to a skin-piercing state wherein the sampling member rotates away from the test member to form an incision in skin, and further wherein each of the sampling members is configured to move from the skin-piercing state to a transfer state wherein the sampling member rotates towards the test member so that the contact portion is in fluidic connection with the test member to transfer body fluid after the skin-piercing.

2. The device according to claim 1, wherein the sampling member is actuated to carry out a piercing movement outwards and backwards into the container, and the test member is arranged stationary inside the container.

3. The device according to claim 1, wherein the sampling member is separated from the test member by means of a spacer in the initial state and the sampling member is configured to move away from the spacer and the test member during the skin-piercing.

4. The device according to claim 3, wherein the spacer extends over a distance in direction of a piercing movement of the sampling member in order to provide a free space between the sampling member and the test member.

5. The device according to claim 3, wherein the spacer is removable by an actuator configured to actuate piercing movement of the sampling member.

6. The device according to claim 3, wherein the spacer is formed with a predetermined breaking point, at a wall of the container defining the retaining chamber, and that the spacer is cut off the wall to achieve the transfer state.

7. The device according to claim 3, wherein the spacer is connected to the container, and the spacer is removable in the transfer state.

8. The device according to claim 1, wherein the sampling member is urged against the test member by means of a resilient element.

9. The device according to claim 8, wherein the sampling member is deflected against a restoring force of the resilient element during the skin-piercing.

10. The device according to claim 9, wherein the sampling member has a flexible bending link forming the resilient element.

11. The device according to claim 1, wherein the sampling member is formed as a hooked needle and a spring-arm of the hooked needle is pre-tensioned against the test member.

12. The device according to claim 1, in which the sampling member has a capillary structure to uptake body fluid, wherein the capillary structure is in fluidic connection with the test member during the transfer state.

13. The device according to claim 1, wherein the sampling member comprises a piercing arm that includes the skin piercing tip, and a laterally open channel is extending along the piercing arm to the contact portion that can be contacted with the test member to transfer body fluid.

14. The device according to claim 1, wherein the sampling member has an engagement slot to receive an actuator rod for driving a piercing movement.

15. The device according to claim 1, wherein the test member is formed as a reagent pad having a reactive layer which is sensitive to an analyte in the body fluid, and the reagent pad is attached to a wall of the container defining the retaining chamber.

16. The device according to claim 1, wherein the test member is configured to be mounted in the container as a unit separate from the sampling member.

17. The device according to claim 1, wherein the container is sealed against the environment by a sealing foil, and at least a piercing part of the sampling member is penetrated through the sealing foil to allow the skin-piercing.

18. The device according to claim 1, wherein the container includes a wall structure which defines the retaining chamber and comprises a desiccant material.

19. The device according to claim 1, wherein the container is formed as a magazine to contain a plurality of sampling members and test members arranged in pairs in respective retaining chambers.

20. The device according to claim 1, wherein the sampling members are actuated through a side face of the disk.

21. The device according to claim 20, wherein the lancet wheel is formed in one piece by etching or cutting a metallic sheet material.

22. The device according to claim 1, wherein the container includes a hub to engage a rotary drive for successive rotary positioning of the sampling members with respect to a sampling port of the apparatus constructed to receive the body part.

23. An apparatus, comprising:
an integrated cartridge having drop-in assembly of components, including
a test ring component having a plurality of test sections;
a lancet wheel component having a lancet rim with a plurality of lancets extending radially inward from the lancet rim, each of the lancets having a leg portion and a lancet tip extending substantially transverse to the leg portion to form a curved contact portion therebetween wherein the curved contact portion is in fluidic connection with the lancet tip, wherein the curved contact portion is configured to contact one of the plurality of test sections to deposit a body fluid sample on the test section; and
a frame component having an egg crate shape with a plurality of chambers to facilitate drop-in assembly of the lancet wheel component onto the frame component.

24. The apparatus of claim 23, further comprising:
the test ring component having a continuous strip of chemistry that spans a circumference of the test ring component, the test ring component being sectionable into the plurality of the test sections; and
wherein the plurality of chambers are configured to section the test ring component into the plurality of the test sections and each of the lancets is positioned next to one test section.

25. The apparatus of claim 24, wherein the leg portion is resilient to move between a first position wherein the lancet tip forms an incision and a second position wherein the curved contact portion contacts the test section.

26. The apparatus of claim 25, further comprising:
wherein the frame component defines a plurality of windows sized to receive the contact portion of the lancet; and
a plurality of cover barriers positioned between the lancet rim and the test ring component to cover the plurality of windows, each of the cover barriers defining a slot sized to receive the contact portion of the lancet, the plurality of cover barriers movable between a first position wherein the cover barriers cover the windows and a second position wherein the slots align over the windows to expose the test section under the cover barriers and allow the curved contact portion of the lancet to contact the test section.

27. The apparatus of claim 24, further comprising:
a first sterility sheet configured to cover the plurality of chambers and the plurality of lancet tips;
wherein the frame component includes a plurality of openings sized to receive a driver; and
a second sterility sheet configured to cover the plurality of openings and the plurality of chambers, wherein the test ring component, the first sterility sheet, and the second sterility sheet maintain the sterility of unused lancets and the humidity of unused test sections.

28. The apparatus of claim 23, wherein the lancet tip is configured to form an incision in skin and the lancet tip includes a capillary groove configured to collect the body fluid sample via capillary action.

29. The apparatus of claim 23, further comprising:
a meter, the meter having the integrated cartridge stored in the meter; and
a driver configured to engage the leg portion of the lancet to rotate the lancet to form an incision in skin with the lancet tip.

30. The apparatus of claim 23, further comprising:
a plurality of wedges made of a desiccant material, wherein one of the wedges is positioned in each chamber of the frame component.

31. The apparatus of claim 23, further comprising:
the test ring component having a continuous strip of chemistry that spans a circumference of the test ring component, the test ring component being sectionable into the plurality of test sections,
wherein the plurality of chambers are configured to section the test ring component into the plurality of test sections and each of the lancets is positioned next to one test section, and
a test ring frame defining a plurality of windows configured to receive the test ring component and to facilitate viewing of the plurality of test sections through the plurality of windows.

32. The apparatus of claim 31, further comprising:
wherein the test ring frame defines a plurality of tester openings sized to receive a lancet tip of the lancet,
a first sterility sheet configured to cover the plurality of tester openings and the plurality of lancet tips; and
a second sterility sheet configured to cover the plurality of chambers of the frame component, wherein the test ring component, the first sterility sheet, and the second sterility sheet maintain the sterility of unused lancets and the humidity of unused test sections.

33. The apparatus of claim 24, wherein the leg portion is resilient to move between a first position wherein the lancet tip forms an incision and a second position wherein the curved contact portion contacts the test section.

34. The apparatus of claim 23, wherein the frame component includes a plurality of slats, and
a pair of the plurality of slats are positioned in each of the plurality of chambers to contact and to restrain the lancet prior to a lancing event and after the lancing event.

35. A method, comprising:
assembling an integrated disposable cartridge, wherein said assembling includes dropping a lancet wheel into a circular frame, the lancet wheel having a rim with a plurality of radially inwardly extending lancets, each of the lancets having a leg portion and a lancet tip extending at an angle from the leg portion to form a contact portion between the leg portion and the lancet tip, wherein the contact portion is in fluidic connection with the lancet tip and is configured to contact a test section to deposit a body fluid sample on the test section, the frame having a plurality of spokes defining a plurality of chambers;

positioning each of the lancets in one of the chambers;

attaching a test ring having a continuous strip of chemistry onto the frame; and sectioning the test ring into a plurality of test sections by the plurality of spokes, each of the test sections positioned under one of the lancets such that each of the lancets is configured to rotate away from the test section to form an incision.

36. The method of claim 35, wherein said assembling further includes:

positioning a plurality of movable cover barriers between the plurality of lancets and the plurality of test sections to eliminate contact between the lancet and the test section until the lancet and the corresponding cover barrier are actuated, wherein each of the cover barriers defines a window to expose a portion of the test section for contact by the lancet.

37. The method of claim 35, further comprising:

forming an incision in tissue with one of the lancet tips wherein the leg portion is in a first position that is substantially parallel to the corresponding test section; and transferring a body fluid sample from the contact portion to the test section wherein the leg portion is in a second position closer to the corresponding test section.

38. The method of claim 35, further comprising:

loading the integrated disposable cartridge into a meter configured to actuate the plurality of lancets.

39. The method of claim 35, further comprising:

dropping a desiccant wheel into the circular frame, the desiccant wheel having a rim with a plurality of wedges, and positioning each of the wedges in one of the chambers.

40. A method, comprising:

providing an integrated disposable cartridge including a frame, a lancet wheel having a plurality of lancets extending radially inward from a rim, and a test ring having a plurality of test sections, each of the plurality of lancets has a lancet tip that extends at an angle from a leg portion to define a contact portion between the lancet tip and the leg portion, the lancet tip having a capillary groove that extends to the contact portion, wherein the contact portions are configured to contact the plurality of test sections;

forming an incision in tissue with one of the lancets by rotating the lancet away from the plurality of test sections;

collecting a body fluid sample with the capillary groove on the lancet;

withdrawing the lancet from the incision in tissue by rotating the lancet towards the plurality of test sections; and transferring the body fluid sample from the capillary groove on the lancet to one of the test sections by contacting the test section with the contact portion of the lancet to release the body fluid sample.

41. The method of claim 40, further comprising:

wherein the rotating the lancet away from the plurality of test sections includes moving a driver towards the lancet in a horizontal direction relative to the frame to contact the lancet; and wherein the rotating the lancet towards the plurality of test sections includes moving the driver away from the lancet in a horizontal direction relative to the frame.

42. The method of claim 40, further comprising:

indexing the frame to an unused lancet after transferring the body fluid sample in the capillary groove to the test section.

43. The method of claim 40, further comprising:

forming a second incision in skin with the lancet to obtain an adequate amount of body fluid sample.

44. An apparatus, comprising:

an integrated cartridge having drop-in assembly of components, including a lancet wheel component having a lancet rim with a plurality of lancets extending radially inward from the lancet rim, each of the lancets having means for forming an incision in skin and means for transferring a body fluid sample to a test element, a frame component having an egg crate shape with a plurality of chambers to facilitate drop-in assembly of the lancet wheel component onto the frame component, a test ring component having a continuous strip of chemistry that spans a circumference of the test ring component, the test ring component being sectionable into a plurality of test elements, and wherein the plurality of chambers are configured to section the test ring component into the plurality of test elements and each of the lancets is positioned next to one test element such that the means for transferring the body fluid sample is in fluidic contact with the one test element to deposit the body fluid sample.

45. The apparatus of claim 44, wherein the means for transferring the body fluid sample includes the lancet having a contact portion to contact the test element and deposit the body fluid sample on the test element.

46. The apparatus of claim 44, wherein the means for transferring the body fluid sample includes the lancet having a lancet tip to contact the test element and deposit the body fluid sample on the test element.

47. The apparatus of claim 44, wherein the frame component includes a plurality of ledges and each of the plurality of ledges defines a notch configured to receive a lancet tip.

48. The apparatus of claim 44, wherein the frame component includes a plurality of slats and a pair of the plurality of slats are positioned in each of the plurality of chambers to contact and to restrain one of the plurality of lancets.

49. An apparatus, comprising:

an integrated cartridge having drop-in assembly of components, including a lancet wheel component having a plurality of lancets, each of the lancets having a leg portion and a lancet tip extending substantially transverse to the leg portion to form a contact portion therebetween, and a frame component having a plurality of chambers to facilitate drop-in assembly of the lancet wheel component onto the frame component;

a test ring component having a continuous strip of chemistry that spans a circumference of the test ring component, the test ring being sectionable into a plurality of test sections, wherein the plurality of chambers are configured to section the test ring component into the plurality of test sections and each of the lancets is positioned next to one test section; and wherein the leg portion is resilient to move between a first position wherein the lancet tip forms an incision and a second position wherein the contact portion is in fluidic connection with the test section to deposit a body fluid sample.

* * * * *